US007576319B2

(12) United States Patent
Miller et al.

(10) Patent No.: US 7,576,319 B2
(45) Date of Patent: Aug. 18, 2009

(54) SYSTEMS FOR DIFFERENTIAL ION MOBILITY ANALYSIS

(75) Inventors: Raanan A. Miller, Chestnut Hill, MA (US); Erkinjon G. Nazarov, Lexington, MA (US); Angela Zapata, Arlington, MA (US); Cristina E. Davis, Cambridge, MA (US); Gary A. Eiceman, Las Cruces, NM (US); Anthony D. Bashall, Concord, MA (US)

(73) Assignees: Sionex Corporation, Bedford, MA (US); The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 12/012,326

(22) Filed: Feb. 1, 2008

(65) Prior Publication Data

US 2008/0128609 A1 Jun. 5, 2008

Related U.S. Application Data

(63) Continuation of application No. 11/807,498, filed on May 29, 2007, now Pat. No. 7,355,170, which is a continuation of application No. 11/305,085, filed on Dec. 16, 2005, now Pat. No. 7,241,989, which is a continuation of application No. 10/797,466, filed on Mar. 10, 2004, now Pat. No. 7,057,168, which is a continuation-in-part of application No. 10/697,708, filed on Oct. 30, 2003, now abandoned, said application No. 10/797,466 is a continuation-in-part of application No. 10/794,776, filed on Mar. 5, 2004, now abandoned, said application No. 10/797,466 and a continuation-in-part of application No. 10/462,206, filed on Jun. 13, 2003, now Pat. No. 7,005,632, is a continuation-in-part of application No. 10/321,822, filed on Dec. 16, 2002, now Pat. No. 6,806,463, and a continuation-in-part of application No. 10/187,464, filed on Jun. 28, 2002, now Pat. No. 7,045,776, and a continuation-in-part of application No. 10/123,030, filed on Apr. 12, 2002, now Pat. No. 6,690,004, said application No. 10/797,466 and a continuation-in-part of application No. 10/321,822, is a continuation-in-part of application No. 09/358,312, filed on Jul. 21, 1999, now Pat. No. 6,495,823.

(60) Provisional application No. 60/422,534, filed on Oct. 31, 2002, provisional application No. 60/453,448, filed on Mar. 10, 2003, provisional application No. 60/453,451, filed on Mar. 10, 2003, provisional application No. 60/530,815, filed on Dec. 18, 2003, provisional application No. 60/389,400, filed on Jun. 15, 2002, provisional application No. 60/398,616, filed on Jul. 25, 2002, provisional application No. 60/418,671, filed on Oct. 15, 2002, provisional application No. 60/453,287, filed on Mar. 10, 2003, provisional application No. 60/468,306, filed on May 6, 2003, provisional application No. 60/549,004, filed on Mar. 1, 2004.

(51) Int. Cl.
*H01J 49/26* (2006.01)
*B01D 59/44* (2006.01)

(52) U.S. Cl. .................. 250/282; 250/281; 250/286; 250/287

(58) Field of Classification Search ......... 250/281–288, 250/290, 292–294
See application file for complete search history.

(56) References Cited

U.S. PATENT DOCUMENTS 2,615,135 A  10/1952  Glenn, Jr.

(Continued)

FOREIGN PATENT DOCUMENTS

SU  966583  10/1982

(Continued)

OTHER PUBLICATIONS

Barnett, D.A. et al., "Isotope Separation Using High-Field Asymmetric Waveform Ion Mobility Spectrometry," Nuclear Instruments & Methods in Physics Research (2000), pp. 179-185, 450(1).

(Continued)

*Primary Examiner*—Bernard E Souw
(74) *Attorney, Agent, or Firm*—Ropes & Gray LLP

(57) ABSTRACT

Disclosed herein are systems, methods and apparatus, for detection and identification of chemical warfare agents (CWAs) using a differential mobility spectrometer.

28 Claims, 42 Drawing Sheets

U.S. PATENT DOCUMENTS

| | | |
|---|---|---|
| 3,511,986 A | 5/1970 | Llewellyn |
| 3,621,240 A | 11/1971 | Cohen et al. |
| 3,931,589 A | 1/1976 | Aisenberg et al. |
| 4,025,818 A | 5/1977 | Giguere et al. |
| 4,201,921 A | 5/1980 | McCorkle |
| 5,218,203 A | 6/1993 | Eisele et al. |
| 5,420,424 A | 5/1995 | Carnahan et al. |
| 5,455,417 A | 10/1995 | Sacristan |
| 5,479,815 A | 1/1996 | White et al. |
| 5,508,204 A | 4/1996 | Norman |
| 5,536,939 A | 7/1996 | Freidhoff et al. |
| 5,654,544 A | 8/1997 | Dresch |
| 5,723,861 A | 3/1998 | Carnahan et al. |
| 5,763,876 A | 6/1998 | Perinarides et al. |
| 5,789,745 A | 8/1998 | Martin et al. |
| 5,801,297 A | 9/1998 | Mifsud et al. |
| 5,801,379 A | 9/1998 | Kouznetsov |
| 5,834,771 A | 11/1998 | Yoon et al. |
| 5,838,003 A | 11/1998 | Bertsch et al. |
| 5,869,344 A | 2/1999 | Linforth et al. |
| 5,965,882 A | 10/1999 | Mergerie et al. |
| 6,049,052 A | 4/2000 | Chutjian et al. |
| 6,066,848 A | 5/2000 | Kassel et al. |
| 6,124,592 A | 9/2000 | Spangler |
| 6,180,414 B1 | 1/2001 | Katzman |
| 6,323,482 B1 | 11/2001 | Clemmer et al. |
| 6,495,823 B1 | 12/2002 | Miller et al. |
| 6,504,149 B2 | 1/2003 | Guevremont et al. |
| 6,512,224 B1 | 1/2003 | Miller et al. |
| 6,540,691 B1 | 4/2003 | Phillips |
| 6,618,712 B1 | 9/2003 | Parker et al. |
| 6,621,077 B1 | 9/2003 | Guevremont et al. |
| 6,639,212 B1 | 10/2003 | Guevremont |
| 6,653,627 B2 | 11/2003 | Guevremont |
| 6,680,203 B2 | 1/2004 | Dasseux et al. |
| 6,690,004 B2 | 2/2004 | Miller et al. |
| 6,703,609 B2 * | 3/2004 | Guevremont et al. ....... 250/287 |
| 6,713,758 B2 | 3/2004 | Guevremont |
| 6,753,522 B2 | 6/2004 | Guevremont |
| 6,770,875 B1 | 8/2004 | Guevremont |
| 6,774,360 B2 | 8/2004 | Guevremont |
| 6,787,765 B2 | 9/2004 | Guevremont |
| 6,799,355 B2 | 10/2004 | Guevremont |
| 6,806,466 B2 | 10/2004 | Guevremont |
| 6,895,804 B2 | 5/2005 | Lovell et al. |
| 7,057,168 B2 * | 6/2006 | Miller et al. ................ 250/287 |
| 7,211,790 B2 | 5/2007 | Ogata et al. |
| 7,241,989 B2 * | 7/2007 | Miller et al. ................ 250/282 |
| 7,355,170 B2 * | 4/2008 | Miller et al. ................ 250/287 |
| 2001/0030285 A1 | 10/2001 | Miller et al. |
| 2002/0070338 A1 | 6/2002 | Loboda |
| 2002/0134932 A1 | 9/2002 | Guevremont et al. |
| 2003/0020012 A1 | 1/2003 | Guevremont et al. |
| 2003/0038235 A1 * | 2/2003 | Guevremont et al. ....... 250/287 |
| 2003/0052263 A1 | 3/2003 | Kaufman et al. |
| 2003/0089847 A1 | 5/2003 | Guevremont et al. |
| 2003/0132380 A1 | 7/2003 | Miller et al. |
| 2004/0004185 A9 * | 1/2004 | Guevremont et al. ....... 250/287 |
| 2004/0094704 A1 | 5/2004 | Miller et al. |
| 2008/0128609 A1 * | 6/2008 | Miller et al. ................ 250/282 |

FOREIGN PATENT DOCUMENTS

| | | |
|---|---|---|
| SU | 1337934 | 9/1987 |
| SU | 1627984 | 2/1991 |
| SU | 1412447 | 6/1998 |
| SU | 1485808 | 10/1998 |
| WO | WO 97/38302 | 10/1997 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/00819 | 2/2001 |
| WO | WO 01/22049 | 3/2001 |
| WO | WO 01/35441 | 5/2001 |
| WO | WO 01/69217 | 9/2001 |
| WO | WO 01/69220 | 9/2001 |
| WO | WO 01/69647 | 9/2001 |
| WO | WO 02/071053 | 9/2002 |
| WO | WO 02/083276 | 10/2002 |
| WO | WO 03/005016 | 1/2003 |
| WO | WO 03/015120 | 2/2003 |

OTHER PUBLICATIONS

Basile, F., A Gas Sample Pre-concentration Device Based on Solid Phase Microextraction (SPME) and Temperature Programmed Desorption (TPD), Instrumentation Sci. Tech., 21(2): 155-164 (2003).

Beverly, M.B. et al., "A Rapid Approach for the Detectino of Dipicolinic acid in Bacterial Spores Using Pyrolysis/Mass Spectrometry," Rapid Communications in Mass Spectrometry, Vo. 10, 455-458 (1996).

Buryakov, I.A. et al., "A New Method of Separation of Multi-Atomic Ions by Mobility at Atmospheric Pressure Using a High-Frequency Amplitude-Asymmetric Strong Electric Field," International Journal of Mass Spectometry and Ion Processes (1993), pp. 143-148, 128.

Buryakov, I.A. et al., "Separation Ions According to Mobility in a Strong AC Electric Field," Sov. Tech. Phs. Lett. (1991), pp. 446-447, 17(6).

Buryakov, I.A. et al., Device and Method For Gas Electrophoresis, Chemical Analysis fo Environment, edit. Prof. V.V. Malakhov, Novosibirsk; Nauka (1991), pp. 113-127.

Carnahan, B. et al., "Field Ion Spectrometry—A New Analytical Technology for Trace Gas Analysis," ISA, (1996), pp. 87-96, 51(1).

Carnahan, B. et al., "Field Ion Spectrometry—A New Technology for Cocaine and Heroin Detection," SPIE, (1997), pp. 106-119, 2937.

Demirev, P.A., et al., "Microorganism Identification by Mass Spectrometry and Protein Database Searchs," Analytical Chem., 71(14): 2732-2738 (1999).

Demirev, P.A., et al., "Tandem Mass Spectromety of Intact Proteins for Characterization of Biomarkers From *Bacillus cereus* T Spores," Analytical Chem., 73(23): 5725-5731 (2001).

Dworzanski, J.P. et al., "Field-Portable, Automated Pyrolysis-GC/IMS System for Rapid Biomarker Detection in Aerosols: A Feasibility Study," Field Analytical Chemistry and Technology, vol. 1, No. 5, 295-305, (1997).

Eiceman, G.A., et al., "Miniature radio-frequency mobility analyzer as a gas chromatographic detector for oxygen-containing volatile organic compounds, pheromones, and other insect attractants," J. Chromatography, 917: 205-217 (2001).

Elhanany, E., et al., "detection of Specific *Bacillus anathracis* Spore Biomarkers by Matrix-Assisted Laser Desorption/Ionization Time-of-Flight Mass Spectromety," Rapid Commun. Mass Spectrom., 15(22): 2110-2116 (2001).

Fox, A., et al, "Determination of Carbohydrate Profiles of *Bacillus anthracis* and *Bacillus cereus* Including Identification of O-Methyl Methylpentoses Using Gas Chromatography-Mass Spectrometry," J Clin. Microbiol., 31(4): 887-894 (1993).

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R., and Purves, R.W., "Atmospheric Pressure Ion Focusing in a High-Field Asymmetric Waveform Ion Mobility Spectrometer," Review of Scientific Instruments, 70(2): 1370-1383 (1999).

Guevremont, R., and Purves, R.W., "High field Asymmetric Waveform Ion Mobility Spectrometry-Mass Spectrometry: An Investigation of Leucine Enkephalin Ions Produced by Electrospray Ionization," J. Am. Soc. Mass Spectrom., 10: 492-501 (1999).

Handy, R., et al., "Determination of nanomlar levels of perchlorate in water by ESI-FAIMS-MS," J. Anal At. Spectrom., 15: 907-911 (2000).

Hathout, Y., et al., "Identification of Bacillus Spores by Matrix-Assisted Laser Desorption Ionization-Mass Spectrometry," Appl. Environ Microbiol., 65(10): 4313-4319 (1999).

Javahery, G. et al., A Segmented Radiofrequency-Only Quadrupole Collision Cell for Measurements of Ion Collision Cross Section on a Triple Quadrupole Mass Spectrometer, J. Am. Soc. Mass. Spectrom., (1997), pp. 697-702, 8.

Krishnamurthy, T., et al., "Liquid Chromatography/Microspray Mass Spectrometry for Bacterial Investigations," Rapid Commun. Mass Spectrom., 13: 39-49 (1999).

Krylov, E.V., "A Method of Reducing Diffusion Losses in a Drift Spectrometer," Technical Physics, (1999), pp. 113-116, 4d(1).

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

Krylov, E.V., "Pulses of Special Shapes Formed on a Capacitive Load," Instruments and Experimental Techniques, (1997), pp. 628, 40(5).

Miller, R.A., et al. "A novel micromachined high-fielded asymmetric wave-ion mobility spectrometer," Sensors and Actuators B 67 (2000), pp. 300-306.

Miller, R.A., et al., "A MEMS Radio-Frequency Ion Mobility Spectrometer for Chemical Agent Detection," Porceedings of the 200 SolidState Sensors and Actuators Workshop, (Hilton Head, SC: Jun. 2000).

Miller, R.A., et al., "A MEMS radio-frequency ion mobility spectrometer for chemical vapor detection," Sensors and Actuators, A91: 301-12 (2001).

Mowry, C., et al., "Rapid Detection of Bacteria with Miniaturized Pyrolysis-Gas Chromatographic Analysis," Proc. Of SPIE, 475: 83-90 (2001).

Phillips, M., "Breath tests in medicine," Scientific American, 267(1): 74-79 (1992).

Phillips, M., "Method for the Collection and Assay of Volatile Organic Compounds in Breath," Analytical Biochemistry, 247: 272-278 (1997).

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E., et al., "Qualitative Evaluation of Field Ion Spectrometry for Chemical Warfare Agent Detection," Proceedings of the ASMS Conference on Mass Spectrometry and Allied Topics, (Jun. 1997), pp. 473A-473B.

Schneider, A. et al., High Sensitivity GC-FIS for Simultaneous Detection of Chemical Warfare Agents, Mine Safety Appliances Co., Pittsburgh, PA, USA, (2000), AT-Process, pp. 124-136, 5(3,4), CODEN: APJCFR ISSN: 1077-419X.

Shute, L.A., et al., "Curie-point Pyrolysis Mass Spectrometry Applied to Characterization and Identification of Selected Bacillus Species," J. Gen. Microbiol., 130(Part 2): 343-355 (1984).

Snyder, A.P., "Detection of the Picolinic Acid Biomarker in Bacillus Spores Using a Potentially Field-Portable Pyrolysis—Gas Chromatography—Ion mobility Spectrometry System," Field Analytical Chemistry and Technology, vol. 1, pp. 49-58 (1996).

Thornton, S.N. et al., "Feasibility of Detecting Dipicolinic Acid in Bacillus Spores Using a Handheld IMS Device with Pyrolysis GC," Proceedings of the 1994 ERDEC Scientific Conference on Chemical and Biological Defense Research, Nov. 1994, Aberdeen Proving Grounds, MD, 1996, pp. 601-607.

Thornton, S.N. et al., "Pyrolysis-Gas Chromatography/Ion Mobility Spectrometry Detection of the Dipicolinic Acid Biomarker in Bacillus Subtillis Spores During Field Bioaerosol Releases," Field analytical Methods for Hazardous Wastes and Toxic Chemicals: Proceedings of a Specialty Conference, Jan. 1997, Las Vegas, NV.

Vaidyanathan, S., et al., "Flow-Injection Electrospray Ionization Mass Spectrometry of Crude Cell Extracts for High-Throughput Bacterial Identification," J. Am. Soc. Mass Spectrom., 13: 118-128 (2002).

Verenchikov, A.N., et al., "Analysis of Ionic Composition of Solutions Using an Ion Gas Analyzer," Chemical Analysis of Environment, edit. Prof. V. V Malakhov., (Novosibirsk, Nauka: 1991), pp. 127-133.

Wang, Z., et al., "Mass Spectrometric Methods for Generation of Protein Mass Database Used for Bacterial Identification," Analytical Chem., 74(13): 3174-3182 (2002).

Krylova, N. et al., "Effect of Moisture on the Field Dependence of Mobility for Gas-Phase Ions of Organophosphorus compounds at Atmospheric Pressure with Field Asymmetric Ion Mobility Spectrometry," J. Phys. Chem. A, vol. 107, 3648-3654: Apr. 16, 2003.

Riegner et al., "Qualitative Evaluation of Field Ion Spectrometry for Chemical Warfare Agent Detection," Proceedings of the ASMS Conference on Mass Spectrometry and Allied Topics, pp. 473A-473B (Jun. 1997).

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05; (May, 1999).

* cited by examiner

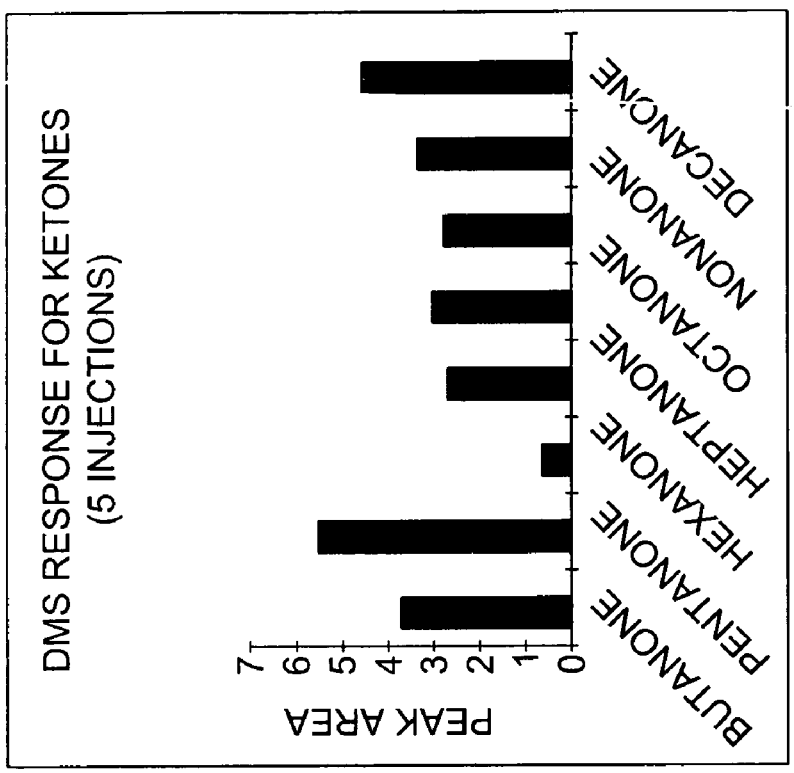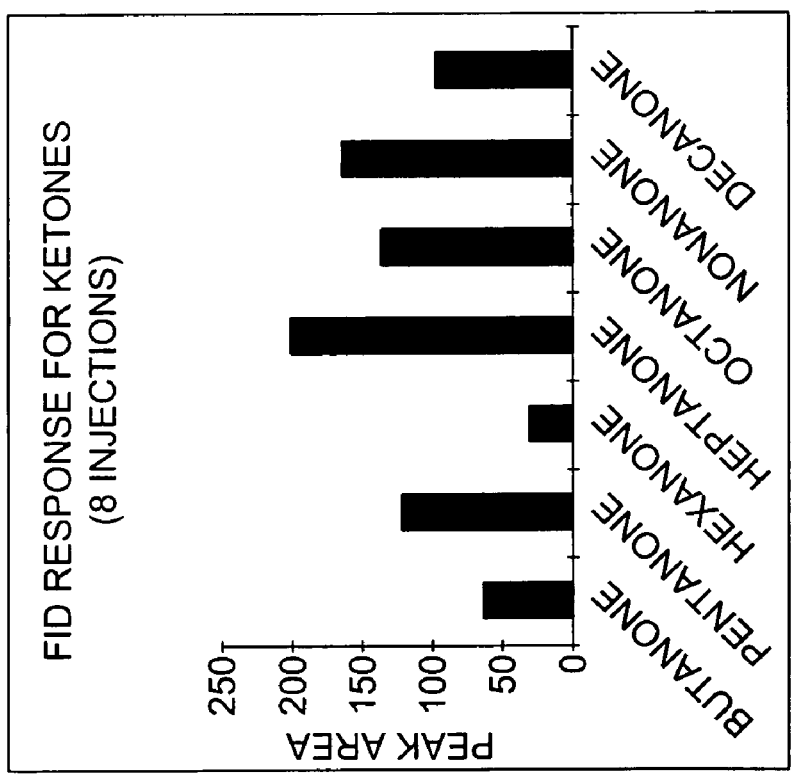
FIG. 20

SYSTEMS FOR DIFFERENTIAL ION MOBILITY ANALYSIS

REFERENCE TO RELATED APPLICATIONS

This application is a continuation of U.S. application Ser. No. 11/807,498, filed on May 29, 2007, which is a continuation of U.S. application Ser. No. 11/305,085, filed on Dec. 16, 2005, which is a continuation of U.S. application Ser. No. 10/797,466, filed on Mar. 10, 2004, which is a continuation-in-part of U.S. application Ser. No. 10/697,708, filed on Oct. 30, 2003, which claims the benefit of Provisional Application No. 60/422,534, filed Oct. 31, 2002. The U.S. application Ser. No. 10/797,466 is a continuation-in-part of U.S. application Ser. No. 10/794,776, filed Mar. 5, 2004, which claims the benefit of Provisional Application No. 60/453,448, filed Mar. 10, 2003. The U.S. application Ser. No. 10/797,466 claims the benefit of U.S. Provisional Application No. 60/453,451, filed on Mar. 10, 2003 and U.S. Provisional Application No. 60/530,815, filed on Dec. 18, 2003. The U.S. application Ser. No. 10/797,466 is a continuation-in-part of U.S. application Ser. No. 10/462,206, filed Jun. 13, 2003, which is a continuation-in-part of U.S. patent application Ser. No. 10/321,822 filed Dec. 16, 2002, a continuation-in-part of U.S. patent application Ser. No. 10/123,030 filed Apr. 12, 2002, and a continuation-in-part of U.S. patent application Ser. No. 10/187,464 filed Jun. 28, 2002, and claims the benefit of U.S. Provisional Application No. 60/389,400 filed Jun. 15, 2002, claims the benefit of U.S. Provisional Application No. 60/398,616 filed Jul. 25, 2002, and claims the benefit of U.S. Provisional Application No. 60/418,671 filed Oct. 15, 2002. The U.S. application Ser. No. 10/797,466 claims the benefit of U.S. Provisional Application No. 60/453,287, filed Mar. 10, 2003, claims the benefit of U.S. Provisional Application No. 60/468,306, filed May 6, 2003, and claims the benefit of U.S. Provisional Application No. 60/549,004, filed Mar. 1, 2004. The U.S. application Ser. No. 10/797,466 is a continuation-in-part of U.S. application Ser. No. 10/321,822, filed Dec. 16, 2002, which is a continuation-in-part of U.S. application Ser. No. 09/358,312, filed Jul. 21, 1999 (U.S. Pat. No. 6,495,823).

This application is related to U.S. application Ser. No. 10/187,464, filed Jun. 28, 2002, which is a continuation-in-part of U.S. application Ser. No. 09/896,536 filed Jun. 30, 2001 entitled "Apparatus For Simultaneous Identification Of Multiple Chemical Compounds;" and claims the benefit of U.S. Provisional Application No. 60/340,894 filed Oct. 30, 2001 entitled "Compound Identification By Mobility Dependence On Electric Field," U.S. Provisional Application No. 60/334,804, filed Oct. 31, 2001 entitled "System For Ion Mobility And Polarity Discrimination And Identification Of Chemical Compounds"; U.S. Provisional Application No. 60/340,904, filed Dec. 12, 2001 entitled "System For Ion Mobility And Polarity Discrimination And Identification Of Chemical Compounds;" U.S. Provisional Application No. 60/342,588 filed Dec. 20, 2001 entitled "Field Dependence Of Mobilities For Gas Phase Protonated Monomers And Proton Bound Dimers Of Ketones By Planar Field Asymmetric Waveform Ion Mobility Spectrometer (PFAIMS);" and U.S. Provisional Application No. 60/351,043 filed Jan. 23, 2002 entitled "Method And Apparatus For FAIMS Detection Of SF6". The entire teachings of the above disclosures are incorporated herein by reference.

BACKGROUND OF THE INVENTION

Spectrometers are used in chemical analysis for identification of compounds in a sample. In some cases a quick indication of presence of particular compounds in a sample is needed, while at other times the goal is complete identification of all compounds in a chemical mixture. Accordingly, samples may be taken directly from the environment and analyzed or may be prepared by processing and/or separating the constituents before spectrometric analysis.

Spectrometers based on ion mobility have been used to detect various chemical and biological compounds. Such spectrometers include ion-mobility spectrometry (IMS) and differential ion mobility spectrometers (DMS) which are also known as field asymmetric waveform ion mobility spectrometers (FAIMS)

Commercially available IMS systems are based on time-of-flight (TOF-IMS), i.e., they measure the time it takes ions to travel from a shutter-gate to a detector through an inert atmosphere (1 to 760 Torr.). The drift time is dependent on the mobility of ions in a low electric field based on size, mass and charge, and is characteristic of the ion species detected. TOF-IMS has been used for detection of many compounds including narcotics, explosives, and chemical warfare agents, and at least one TOF-IMS system has been adapted for use in a field-portable device for detection of bacterial spores in the environment.

DMS devices offer an alternative to the low field TOF-IMS ion mobility process. In DMS, ion filtering is achieved based on accentuating differences in mobility of ionized molecules in a high field. The high field mobility differences are used for "signature" identification of chemical species in an ionized sample. DMS filtering is an efficient process, combining controlled neutralization of unselected ion species while passing selected ion species for detection.

There is a strong and continuing interest in improved approaches to sample characterization, particularly as may be provided in compact and portable devices.

SUMMARY OF THE INVENTION

Practices of the present invention are directed to methods and devices for detection and identification of analytes in samples using the mobility-based signature that is produced when a volatilized sample is passed through a differential ion mobility spectrometry (DMS) device. Any volatized or volatilizable sample can be analyzed including organic, chemical, agricultural or biological samples. In one embodiment, the present invention includes using DMS to generate separation data and at least one other processing step that yields its own separation data. This additional separation step may be before or after DMS filtering. Analytes are reliably identified based on this combination of data.

In one embodiment, the samples subjected to the analysis by the methods and devices of the present invention are either normally existent in the volatile state or require volatilization. Analytes in a sample can be volatilized with or without fragmentation. Analyte volatilization and fragmentation can be achieved by any of the techniques known in the art including pyrolysis, thermodesorption, laser ionization, microwave heating or chemical transformation. Either prior to or following the volatilization, analytes in a sample can be additionally separated using any of the techniques known in the art such as gas chromatography.

Each analyte is detected by its ion-mobility based signature. This signature is expressed as stored spectrometric data uniquely identifying the species being analyzed. The combination and relative abundances of various analytes in a sample forms a pattern that can be used to identify the entire sample by use of the stored reference data. Preferably the ion-mobility based signature is based on the differential mobility of that species as experienced in the compensated DMS filter field.

Analysis of physiological samples can identify diseases, monitor patient's condition or provide forensic information; analysis of environmental samples can detect chemical or biological contamination, including agents of chemical and biological warfare, or determine geochemical composition of soil and sediments; analysis of food quality samples can detect bacterial and chemical contamination as well as early signs of decomposition; analysis of chemical samples can be used to monitor small and industrial scale processes as well as safety conditions; analysis of biological samples can be used to identify microorganisms in pure or mixed cultures as well as assess efficiency of medication or other antibiotic compounds; analysis of industrial samples can be used to monitor the quality of the material; analysis of agricultural samples can detect pesticides, herbicides as well as analyze soil and determine quality of crops.

Accordingly, one embodiment of the invention is directed to a method of detection and identification of analytes in a sample by an ion mobility based device, comprising (a) obtaining a volatilized sample comprising markers that are detectable by an aspect of ion mobility (preferably by DMS); and (b) directing at least a portion of the volatilized sample to a DMS detection device to obtain a mobility-based signature of at least one marker, wherein the mobility-based signature correlates with an analyte in the sample, thereby detecting and identifying at least one analyte in the sample.

In another embodiment, the present invention is a method of detection and identification of analytes in a sample, comprising (a) volatilizing at least a portion of the sample to produce a volatilized sample that includes markers detectable by an aspect of ion mobility; and (b) directing at least a portion of the volatilized sample to a DMS device, to obtain a mobility-based signature of at least one marker, wherein the mobility-based signature correlates with an analyte in the sample, thereby detecting and identifying at least one analyte in the sample.

In another embodiment, the present invention is a device for analysis of samples (e.g., biological, chemical, organic, agricultural) using an aspect of ion mobility, comprising (a) a volatilization part; and (b) a differential ion mobility spectrometry (DMS) device connected to said volatilization part.

In another embodiment, the present invention is directed to a field asymmetric ion mobility detection system, comprising an input part and an output part, the input part including a volatilization part; at least a pair of spaced insulated substrates cooperating to define between them an enclosed flow path for the flow of ions from the input part to the output part; at least two electrodes opposite each other and defined in the flow path, the at least two electrodes including at least one filter electrode associated with each substrate to form an ion filter section; and an electronics part configured to apply controlling signals to the electrodes, and the electronics part applying an asymmetric periodic signal across the filter electrodes for filtering the flow of ions in the flow path, the filter being compensated to pass desired ion species out of the filter section.

In one embodiment, the present invention is a method of detection and identification of analytes in a sample by an ion mobility-based device, comprising directing a portion of a sample into a first separation device thereby obtaining a first profile; directing a portion of a sample into a second separation device thereby obtaining a second profile, wherein at least one of the first and the second separation devices is a DMS device; and (c) combining the first and the second profiles thereby identifying at least one analyte in a sample.

The instant invention advantageously employs differential mobility spectrometry in a number of heretofore undisclosed industrial, clinical, diagnostic and environmental applications. The methods and devices of the present invention enable rapid detection and identification of compounds. Such detection and identification can be made rapidly and with a high level of confidence. Practices of the invention are sensitive to parts per billion and even parts per trillion levels. Furthermore, unlike the devices of prior art, embodiments of the invention can simultaneously filter and detect both positive and negative ions of an ion species. Systems of the invention may be used alone or in combination with other analytical equipment with increased likelihood of accurate identification of chemical compounds, even at trace levels, and even for complex mixtures that heretofore have been difficult to resolve. As a result, an inexpensive, fast and accurate chemical marker (including biomarker) analysis system which can even be provided in a compact and field-portable package.

BRIEF DESCRIPTION OF THE DRAWINGS

The patent or application file contains at least one drawing executed in color. Copies of this patent or patent application publication with color drawings will be provided by the Office upon request and payment of the necessary fee, as needed.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 20 shows comparison of prior art FID and a DMS embodiment of the invention for reproducibility for a homologous alcohol mixture.

FIG. 21 shows the results from py-GC-DMS characterization of positive ions for *E. coli* (A), *M. luteus* (B), and *B. megaterium* (C).

FIG. 22 shows the results from py-GC-DMS characterization of negative ions for *E. coli* (A), *M. luteus* (B), and *B. megaterium* (C).

FIG. 23 the profiles from py-GC-DMS analyses of *E. coli*, Lipid A and mixtures of Lipid A and *E. coli.*

FIG. 24 shows the compensation voltage versus retention time for the 50 peaks of highest intensity in py-GC DMS analyses of *E. coli* (grey signals) and *M. luteus* (black signals) for positive polarity ions.

FIG. 25 shows the compensation voltage versus retention time for the 30 peaks of highest intensity in py-GC-DMS analyses of *E. coli* (grey signals) and *M. luteus* (black signals) for negative polarity ions.

FIG. 26 shows the effect of separation voltage on py-GC/DMS characterization of *B. megaterium* in positive polarity.

FIG. 27 shows the effect of temperature on py-GC/DMS characterization of *B. megaterium* in positive polarity.

FIG. 28 shows the Peak area versus number of bacteria for *B. megaterium* (A), *M. luteus* (B), and *E. coli* (C).

FIG. 29 shows overlapping prior art TOF-IMS spectra for m-Xylene and p-Xylene isomers.

FIG. 30 shows resolved DMS spectra for m-Xylene and p-Xylene.

FIG. 31 shows positive ion spectra for different concentrations of methyl salycilate.

FIG. 32 shows concentration dependence of the invention to methyl salycilate for both positive and negative ion spectra.

FIG. 33 shows total ion chromatograms from GC-MS analysis of emissions of organic compounds trapped on SPME fibers by sampling plumes from combustion of several materials.

FIG. 34 shows mass spectra from direct characterization of grass, cotton and cigarette smoke using atmospheric pressure chemical ionization mass spectrometry.

FIG. 35 shows plots of total intensity of product ions versus retention time from GC-DMS characterization of emissions of organic compounds trapped on SPME fibers in plumes from combustion of cotton, paper and grass.

FIG. 36 shows plots of total intensity of product ions versus retention time from GC-DMS characterization of emissions of organic compounds trapped on SPME fibers in plumes from combustion of cigarette and engine exhausts. Plots can be compared directly to FIG. 35.

FIG. 37 shows topographic plots from GC-DMS characterization of emissions of organic compounds trapped on SPME fibers in plumes from combustion of cotton and paper.

FIG. 38 shows topographic plots from GC-DMS characterization of emissions of organic compounds trapped on SPME fibers in plumes from combustion of grass and gasoline.

FIG. 39 shows plots of ion chromatograms extracted from analyses by GC-DMS of emissions from combustion of cotton (top frame) and paper (bottom frame. Ion chromatograms were extracted from plots in FIG. 37.

FIG. 40 shows plots of ion chromatograms extracted from analyses by GC-DMS of emissions from combustion of grass (top frame) and from engine exhausts (bottom frame), as extracted from plots in FIG. 38.

FIG. 41 shows resolution of a nerve gas and an interferant simulants at different radio frequency field strengths by a DMS device of the present invention.

FIG. 42A and FIG. 42B show DMS spectra of both positive and negative ion peaks, or modes, for a nerve agent stimulant GA.

FIG. 43 shows the effect of reduced pressure on resolution of various peaks by a DMS device of the invention. Resolution increases when pressure is decreased.

FIG. 44 demonstrates a practice of the invention for a series of warfare agent simulants selectively mixed with 1% headspace of aqueous fire fighting foam. As can be seen, good peak resolution can be achieved in practice of the invention.

DETAILED DESCRIPTION OF THE INVENTION

The present invention is directed to methods and devices for detection and identification of analytes in chemical, biological, agricultural or organic samples using characteristic mobility-based behavior of the volatilized sample as it is passed through a differential ion mobility spectrometry (DMS) device of the invention. This characteristic behavior is also referred to herein as a signature, by means of which ion species can be separated, detected and identified in practice of the invention. In preferred practices, this signature is ion-mobility based and detected in gas-phase DMS.

Preferably each analyte is detected at least by its ion-mobility based signature. DMS species identification is done by making a species detection and comparing this data to stored data which uniquely identify a species based upon aspects of ion mobility, i.e., differential mobility. Briefly, the data may include field conditions (e.g., wavelength, frequency, intensity, among others), compensation voltage (a DC offset, or variations in the RF signal, such as changes in duty cycle, among others) and also may include flow characteristics (such as flow rate or field gradient, among others) and temperature. DMS produces a signature representing differences in ion mobility between high field and low field conditions. In one embodiment, a signature used in the methods of the present invention is the combination of the compensation voltage and a field strength that results in a known spectral output associated with the species being analyzed. In a further practice of the invention, time of flight ion mobility is used to further characterize aspects of a detected ion species to further assist species identification.

Principles of Differential Ion Mobility Spectrometry

Differential ion mobility spectrometry is a technique for ion separation, detection and identification. An asymmetric varying high RF field is established between filter electrodes over a flow path. Ions in the flow path are driven by the field transversely and eventually are neutralized as they contact the electrodes. However compensation is applied to return an ion species of interest to the center of the flow and to pass through the ion filter unneutralized. This process is species-dependent.

Figure 1:
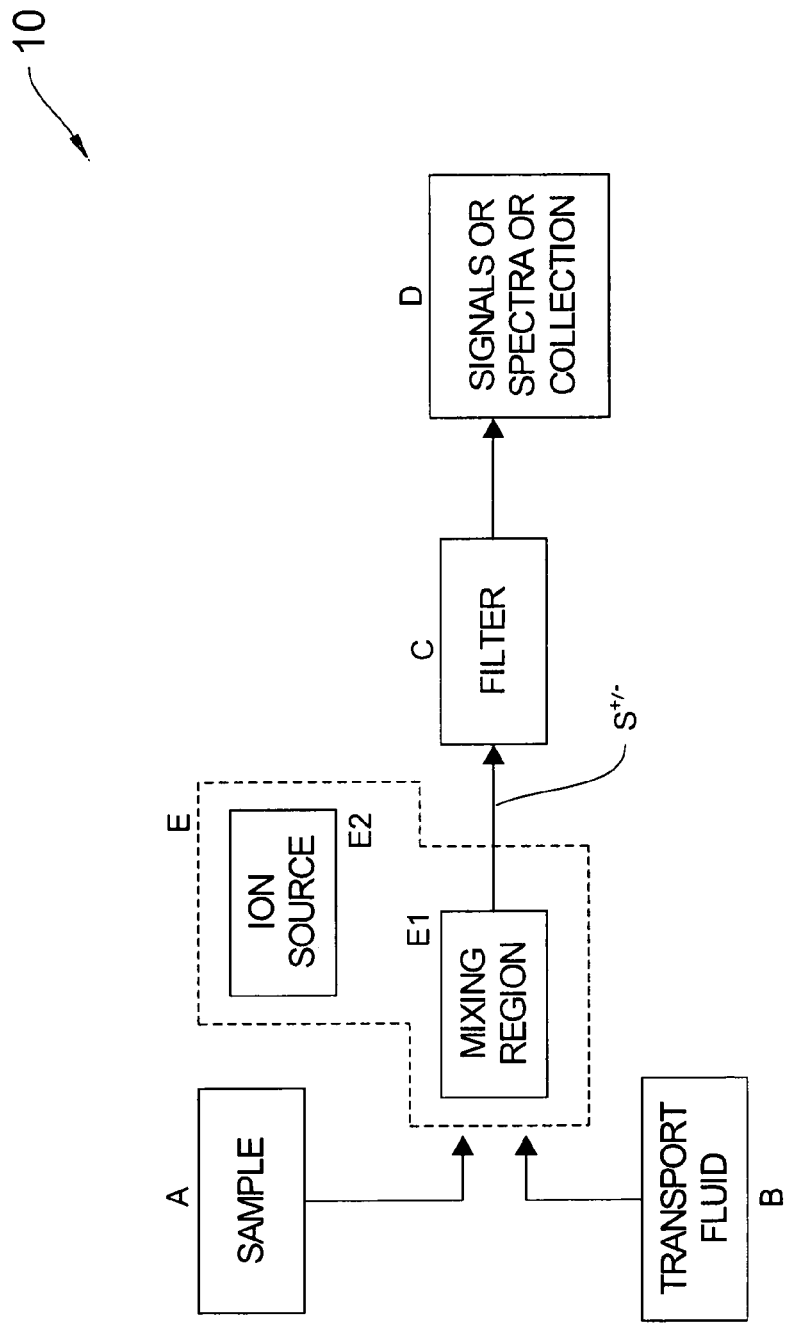
FIG. 1 is a schematic flow diagram of an embodiment of the invention.

If ions derived from two compounds respond differently to the applied high strength electric field, the ratio of high to low field mobility may be different for each compound. Consequently, the magnitude of the compensation necessary to counteract the drift of the ions toward either plate is also different for each ion species. Thus, when a mixture including several species of ions is being analyzed by DMS, ideally only one species of ion is selectively transmitted to the detector for a given combination of compensation and RF field. The remaining ions in the sample drift toward the filter electrodes and are neutralized upon contact.

The present invention may be practiced with various configurations. Preferred embodiments feature compact and field-portable, wide-spectrum, dual mode, DMS systems, such as taught in U.S. application Ser. No. 10/123,030, U.S. provisional application No. 60/389,400, as well as the device described in U.S. Pat. Nos. 6,495,823 and 6,512,224 and in copending U.S. application Ser. No. 10/187,464, filed Jun. 28, 2002, and U.S. application Ser. No. 10/462,206, filed Jun. 13, 2003. The entire teachings of the above-referenced disclosures are incorporated herein by reference.

Application of the Methods of the Invention

The methods of the present invention can be used to analyze any volatile or volatilizable sample. As used herein, the term "volatile" means evaporating readily at normal temperatures and pressures. The term "volatilizable" means capable of being converted into gas by use of any of the volatilization methods known in the art. As used herein, the term "volatilization" refers to a process of conversion of solid or liquid to a gas.

In some embodiments, purification, fractionation and/or separation of a sample is desired prior to collection of volatile components or volatilization of a sample or a part thereof. Samples can be optionally purified or separated before beginning the DMS analysis by any of the standard techniques known in the art such as HPLC, turbulent flow chromatography, liquid chromatography, reverse phase chromatography, affinity chromatography, supercritical fluid chromatography, gas chromatography (GC), electrophoresis (including but not limited to capillary electrophoresis, polyacrylamide gel electrophoresis, agarose gel electrophoresis), solid phase extraction, and liquid phase extraction, preferably using different solvents (e.g., chloroform/methanol for lipids, water for polar molecules). The capillary of the ion source could be filled with silica beads (derivatized or not) or other material to perform chromatography and/or separation. Volatile or volatilized components can further be separated into fractions by any technique known in the art, for example, gas chromatography (GC), desorption/absorption, effusion, condensation, filtration, ion exchange, or the like.

In one embodiment, the sample contains volatile components. A volatile sample can be collected from the source by collecting headspace or any other technique known in the art such as filtration, distillation, sublimation, vacuum distillation, etc.

Volatile or volatilized components can be directly subjected to DMS analysis or further separated using any of the techniques as described herein. In one embodiment, the volatile components are filtered through a membrane to reduce moisture content and other impurities that may affect signal-to-noise ratio. One skilled in the art can determine the material of a membrane based on the properties of the analytes to be separated (for example, polarity). Membrane materials can include, for example, polymers such as Teflon or dimethyl silicon.

In other embodiments, samples do not contain volatile components or may contain a combination of volatile and nonvolatile components. Where analysis of non-volatile components of a sample is desired, these samples can be subjected to gas-phase DMS analysis as long as they are volatilizable. For example, samples of body tissues, pathogens, building materials or samples of soil may not be volatile, but are volatilizable. Likewise, breath can contain both volatile components and non-volatile but volatilizable components. These components can be separated as described herein and the volatilizable components subjected to volatilization and analysis by DMS.

The whole sample or any fraction thereof can be subjected to volatilization. Volatilization can be performed in the presence or absence of an oxygen environment. In one embodiment, volatilization produces a complex mixture of chemicals referred to herein as "markers". Markers can include whole molecules or fragments thereof. The composition and relative abundance of the markers in a volatilized sample uniquely identifies the sample. Such sample may be organic or inorganic, chemical, biological or otherwise.

Any of the techniques known in the art can be used for volatilization. Preferably, sufficient energy is applied to a sample to break intra- or inter-molecular chemical bonds of the analytes in the sample. Non-limiting examples include pyrolysis, thermal desorption, including temperature-programmed desorption and thermally assisted solid phase micro-extraction (SPME), laser ionization, including matrix assisted laser desorption ionization (MALDI), microwave excitation (heating with microwaves), and chemical transformation (e.g., hydrolysis, photolysis, oxidation, etc.).

A particularly useful method of volatilization is pyrolysis. The term pyrolysis (PY) refers to a procedure in which a material is heated, usually in the absence of oxygen, thereby causing the material to break down into simpler compounds. Pyrolysis provides a volatilization technique for various types of sample analysis, especially for samples that are not easily volatilized. Pyrolyzing a sample produces a complex mixture of volatile, semi-volatile and non-volatile organic chemicals (herein referred to as pyrolysate). Vapors generated during pyrolysis can be swept directly into a detection device. The composition and relative abundance of various components in the pyrolysate is a unique characteristic of a given sample. Accordingly, the sample can be characterized by analyzing pyrolysis products using DMS to produce a "fingerprint," i.e., signature, that can uniquely identify the sample.

Another method for volatilization of a sample is thermal desorption, which is a widely used technique for extracting and isolating volatile and semi-volatile compounds from various matrices. For thermal desorption, samples, usually solids, are heated and analytes are volatilized. Typically, a carrier gas or vacuum system transports the volatilized components to a detection device. Based on the operating temperature of the desorber, thermal desorption processes can be categorized into two groups: high temperature thermal desorption (HTTD) (320 to 560° C. or 600 to 1000° F.) and low temperature thermal desorption (LTTD) (90 to 320° C. or 200 to 600° F.). It is the technique of choice for air monitoring (indoor, outdoor, workplace, automobile interior, breath, etc.) and is a tool for the analysis of soil, polymers, packaging materials, foods, flavors, cosmetics, tobacco, building materials, pharmaceuticals, and consumer products. Almost any sample containing volatile organic compounds can be analyzed using some variation of this technique.

Temperature programmed desorption (TPD) is a variation of thermal desorption whereby the temperature of a desorber is increased in a pre-programmed manner to maximize the temporal resolution of the analytes and contaminants (noise) in a sample. TPD is often advantageously coupled to solid phase micro-extraction (SPME). SPME is a technique of pre-concentration of analytes whereby the analytes of interest are extracted from a sample by absorption into solid phase material, usually fibers. Absorption of the analytes by the fibers is based on the affinity and solubility of the analytes in the solid phase material of the fibers. Solid phase materials can include various polymers, for example, polyacrylate, polydimethylsiloxane, divinylbenzene and mixtures thereof. Analytes can be extracted from either gas or liquid phases. Alternatively, a solid sample can be subjected to thermal desorption and the volatile analytes released during this process can be absorbed by SPME fibers, thus pre-concentrating the analytes of interest. Following the extraction, the compounds are thermally desorbed by a pre-programmed temperature ramping and directed for analysis and detection. An example of a suitable TPD/SPME device is disclosed in Basile, F., *Instrumentation Sci. Tech.* 31(2): 155-164 (2003), the entire teachings of which are herein incorporated by reference.

MALDI is a method that allows for vaporization and ionization of non-volatile samples from a solid-state phase directly into the gas phase at atmospheric pressure of in vacuum. Briefly, the technique involves mixing the analyte of interest with a large molar excess of a matrix compound, usually a weak organic acid. This mixture is placed on a vacuum probe and inserted into a detection device for laser desorption analysis. During laser desorption, the matrix that also contains the analytes is irradiated with lasers in order to transfer the content into the gas phase. The matrix strongly adsorbs the laser light at a wavelength at which the analyte is only weakly absorbing. As a result, the matrix reduces intermolecular contacts beyond analyte-matrix interactions thereby reducing the desorption energy. The results are high ion yields of the intact analyte and giving rise to sub-picomole sensitivity. Principles of MALDI are well-known in the art. MALDI devices suitable for use with the present invention are described, for example, in U.S. Pat. Nos. 6,414,306 and 6,175,112, the entire teachings of which are herein incorporated by reference.

The whole sample or any analyte in a sample can be subjected to volatilization. In one embodiment, the markers produced by volatilization of a sample are separated using any of the standard separation techniques used in the art, for example, gas chromatography. Following chromatographic separation, any or all fractions can be subjected to DMS-based detection.

Various illustrative applications of the methods of the present invention are described in detail below under separate headings. Generally, samples can be derived from any source and can include physiological, environmental, biological, chemical, agricultural and industrial sources.

Physiological samples such as breath or tissue samples or physiological fluids (including blood, urine, synovial fluid, saliva, etc.) can be used to diagnose and monitor patient conditions, including point of care patient monitoring, and provide forensic information.

Environmental samples such as air, soil, sediments, petroleum, natural gas or water can be used to detect chemical or biological contamination, including that by heavy metals, and in monitoring of remediation sites, berms, incinerator wastes and water treatment facilities. Methods of the present invention can be used for detecting agents of chemical and biological warfare in a sample.

Food quality samples, such as foodstuff, air samples from refrigerators or containers, and swabs of food-contacting surfaces, can be used to detect bacterial and chemical contamination of as well as early signs of decomposition during shipping, in monitoring shelf life and/or package tampering.

Chemical samples, such as samples of reaction mixtures, can be used to monitor small and industrial scale processes, including the extent of reactions and detection and separation of stereoisomers, as well as to monitor safety conditions.

Biological samples, such as samples of pathogens, can be used to identify microorganisms in pure or mixed cultures as well as assess efficiency of medication or other antibiotic compounds. Industrial samples, such as samples of medicaments, sample of cosmetic products, samples of building materials, samples of crop plants, fabric, synthetic polymers and organic materials, can be used to monitor the quality and integrity of the material.

In one embodiment, the sample includes whole microorganisms, non-microbiotic pathogens or other biological materials. In one embodiment of the invention, a sample can include protozoan, fungal, bacterial or viral infectious agents, antibodies and other proteins, nucleic acids, peptides, peptidomemetics, peptide-nucleic acids, oligonucleotides, aptamers, lipids, polysaccharides, liposaccharides, lipoproteins, glycoproteins, and small molecules. In preferred embodiments, the sample contains infectious agents and microorganisms such as protozoa, fingi, bacteria and virus.

The practice of the method of the present invention includes subjecting volatile or volatilized markers and/or other sample components to DMS analysis, which can optionally be combined with ion mobility spectrometry (IMS). IMS is well known in the art.

In alternative embodiments, IMS can be used prior to, following or in parallel with the DMS analysis. The use of IMS can aid and/or supplement DMS analysis in some cases. For example, an IMS device can be used as an ion filter to additionally separate and filter the analytes of the sample or the volatilized markers and/or analytes, thus raising sensitivity and signal-to-noise ratio of the DMS device and its detectors.

Further, a given sample can be subjected to an IMS analysis in parallel with a DMS analysis. In this embodiment, IMS spectra can be compared to those obtained by a DMS device. By comparing the two types of spectra, additional information useful in analysis and identification of the markers and analytes can be obtained.

In a further embodiment, the present invention is a method of sample identification, wherein a sample is analyzed and the analytes contained therein identified by a multi-stage process that includes differential mobility analysis. In one embodiment, a first stage of sample processing can include filtering a sample by particle size, a second stage can include volatilization and the next stage can include differential ion mobility. In another embodiment, the present invention is a method of analysis of complex mixtures that includes coupled Ion Mobility/Multiple Stage Mass Spectrometry.

Illustrative Embodiments of Clinical, Industrial, Research and Public Health Applications The present invention can be used in the identification of microorganisms, in clinical, research, industrial, and public health applications, including terrorism.

For example, the invention is useful in diagnosing bacterial, viral, fungal and protozoan diseases and infections affecting particular patients. Patients can be human, primates, companion animals (dogs, cats, birds, fish etc.), livestock (cows, sheep, fish, fowl and poultry, etc.). In a preferred embodiment, the present invention can be used for pathogen identification in mixed cultures, without the need for isolating and culturing of the microorganisms. Briefly, a sample of infected tissue, a physiological fluid from a patient or a sample of a pathogen culture is volatilized. The pathogen culture can be mixed, i.e., contain more than one type of microorganisms. The volatilized sample, optionally separated by a suitable separation technique known in the art, such as gas chromatography, is directed to a DMS detection device of the present invention. Because the volatilized sample comprises markers unique to the pathogens in the sample, the pathogens are identified. In an alternative embodiment, volatile compounds emitted by the organisms (methane, ammonia, ethylene, plant alkaloids as well as oxygen, carbon dioxide, products of amino acid decarboxylation, protein and lipids decomposition) can be detected to assess cell growth and death as well as other physiological changes.

In one embodiment, the methods of the present invention are used in the rapid identification of antibiotic resistant strains of organisms such as *Staphylococcus aureus* and *Mycobacterium tuberculosis*, and may optionally be used to determine to which antibiotics or combinations of antibiotics the particular strain of bacterium infecting the patient is susceptible. Additionally, the invention is useful in distinguishing between diseases with similar clinical manifestations but different causative agents, with possible differences in the preferred course of treatment.

In another embodiment, the invention can be used in the identification of pathogenic and non-pathogenic fungi, as well as determining which agents are effective against fungal infections. Both the systemic disease caused by primary pathogens such as *Histoplasma capsulatum* and the opportunistic mycoses caused by *Candida albicans* or *Cryptococcus neoformans* can be detected using methods of the present invention. Assessment of the type of infectious agent can lead to better methods for treatment.

The invention is useful in the diagnosis of at least some of the protozoan parasites, and especially those, such as *N. fowleri*, which require culturing for definitive diagnosis. The invention is also useful in the determination of appropriate treatment of an infection by any parasite. For example, in some geographic areas, *Plasmodium falciparum*, the organism associated with the majority of the one to two million deaths annually from malaria, has developed resistance to chloroquine, the first-line agent used in treatment. As described herein with reference to bacteria, by detecting relative abundances of the pathogens in a time series of samples, the invention can be used to determine to which agents the parasites infecting an individual show susceptibility.

In another embodiment, the present invention can be used in the diagnosis of viral diseases, as well as the determination of agents to which particular viruses show susceptibility. Exemplary viruses which can be identified using the DMS analysis of the present invention, either by sampling patient tissues or bodily fluids or after replication in culture include: Herpesviruses, which infect vertebrates, including humans (Varicella-Zoster (chickenpox, shingles), Epstein-Barr and Cytomegalovirus (infectious mononucleosis), Herpes Simplex (herpes, Kaposi's sarcoma); Baculoviruses, which infect invertebrates (especially insects such as silk worms); iridovirus, which causes African swine fever; Poxviruses, which infect invertirates and veritebrates, including humans causing Variola (smallpox), Vaccinia, Monkeypox, Mousepox; adenovirus, which infect vertebrates, including humans and causes colds; caulimoviruses, which infect plants; papillomavirus, which causes warts and other tumors; bacteriophages; hepadnavirus, which infect vertebrates, including humans (Hepatitis B); reoviruses, which infect invertebrates, plants, and vertebrates, including humans; flaviviruses, which infect vertebrates, including humans causing yellow fever; Dengue fever and hepatitis C; togaviruses, which infect plants and vertebrates causing rubella, St. Louis, Eastern/Western (equine) encephalitis; picornaviruses, which infect vertebrates, including humans causing polio, colds and hepatitis A; potyviruses, which infect plants; various oncornaviruses, which infect vertebrates, including humans, causing cancer (Avian Leucosis Virus; Murine Leukemia Virus; Rous Sarcoma Virus; human T-cell Leukemia Virus (HTLV); Lentiviruses, which infect vertebrates, including humans, causing HIV (AIDS) and feline immunodeficiency; orthomyxoviridae, which infect vertebrates, including humans, causing influenza; filoviridae, which infect vertebrates, including humans causing Ebola fever, Marburg fever; paramyxoviruses, which infect vertebrates, including humans (Morbilivirus (measles), parainfluinza virus, Rubulavirus (mumps), Respiratory Syncytial Virus (colds, croup); rhabdoviridae, which infect invertebrates, plants, or vertebrates, including humans (Rabies, Vesicular Stomatitis); arenaviruses, which infect vertebrates, including humans (Lymphocytic ChorioMeningitis); bunyaviruses, which infect plants and vertebrates, including humans (La Cross Virus (encephalitis), Sin Nombre Virus (hantavirus pulmonary syndrome), other hemorrhagic fevers).

The methods of present invention can further be used in determination and diagnosis of animal and human disease such as Creutzfeld-Jacob disease, scrapie and mad cow disease, where the infectious agent is a conformer of a wild-type analog.

The present invention can be used for public health monitoring. The presence of coliforms, such as *E. coli*, in waters off beaches is often used as a marker for the presence of untreated sewage. The invention can be used in testing of water samples to determine whether coliforms are present, without first having to isolate and culture the various microorganisms in the sample. Volatilization of a mixed bacterial sample produces markers unique for each microorganism in a sample. In another example, the invention can be used to determine the presence of *Cryptosporidium* or *Vibrio cholerae* in water supplies. The invention can be used for testing of municipal water supplies and other waters for the presence of these and other pathogens.

The invention can further be used in the determination of which chemical agents are effective against the particular organism or strain of organism infecting a particular patient. Briefly, a time series of samples of infected tissue, a physiological fluid or samples of a mixed pathogen culture from a patient being administered a specific chemical agent are analyzed using aspects of ion mobility as described herein. The methods of the present invention can identify which of the pathogens responds to the selected treatment. Thus, the invention can be employed in screening novel chemical compositions as antibiotics for their potential efficacy as agents to kill or inhibit the growth of microorganisms. In general, screening typically involves dividing cultures of the organism into multiple aliquots. The agents being tested are then introduced into a first group of the aliquots, while a second aliquot is reserved as a control to which no agent is added. The relative amounts of the organisms in the first test group are then compared to the amounts of the organisms grown in the presence of the agents in the second, control group so that the relative effectiveness of the agents being tested can be determined. Large numbers of aliquots can be cultured and tested in parallel, permitting the testing of large numbers of potential agents to be tested at once. Due to high sensitivity of the methods of the invention, this embodiment can be particularly beneficial where large scale culturing of microorganisms is to be avoided.

The general format of microorganism assays employed by the methods of the present invention will now be described. For ease of description, the methods described below will be directed toward bacteria, although fungi, protozoa and viruses can be employed with modifications familiar to persons of skill in the art.

A specimen to be subjected to analysis, for example blood, urine, mouth or vaginal swab, personal odor, or a sample of food or of water believed to contain a pathogen (e.g. virus, bacteria, fingi or protozoa) is obtained. If not already in the form of an aqueous suspension, the specimen is usually suspended in an aqueous medium prior to being subjected to the process of this invention. The size of the sample is not critical, provided a sufficient number of microorganisms are obtained to permit the intended procedures to be performed. Further, the numbers of bacteria present in the aqueous suspension are not critical, provided a sufficient number of bacteria are present for the procedure of this invention to detect differences between test and control samples. The time required to perform the analysis, however, can be reduced as the concentration of microorganisms increases.

If the specimen has too low a cell concentration, it may be concentrated by known techniques, such as centrifugation or by culturing. The specimen is cultured by incubating under conditions suitable for sustaining bacterial growth. The period of incubation is that period sufficient to obtain detectable growth, which will differ depending upon factors such as bacterial species and concentration of organisms in the sample.

After the optional incubation of the test and control specimens for a period of time, the specimens are volatilized and quantitatively and qualitatively analyzed using ion mobility detection devices of the present invention.

One skilled in the art will readily determine the necessary culturing conditions. The choice of a particular method of culturing the microorganism or microorganisms of interest is determined by a person skilled in the art.

Analysis of Physiological Fluids and Other Biological Samples

Analysis of physiological fluids and other biological samples by the methods of the present invention can be done by employing any of the volatilization procedures described herein. In one embodiment, the volatile components of a sample are analyzed by collecting the volatile analytes at a headspace of a liquid or solid sample. In another embodiment, a liquid or solid sample can be volatilized as described herein.

Samples can be obtained from a variety of sources. As will be appreciated by those in the art, the sources comprise any number of things, including, but not limited to, cells (including both primary cells and cultured cell lines), tissues and bodily fluids (including, but not limited to, blood, urine, serum, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (e.g., a normal joint or a joint affected by disease such as rheumatoid arthritis, osteoarthritis, gout or septic arthritis) of virtually any organism. Samples can be obtained, for example, from plants (e.g., crops), invertebrates (e.g., silk worms), non-mammalian vertebrates (e.g., poultry, fish, exotic birds, fowl), non-human mammals (e.g., livestock, companion animals, primates) and humans. Samples can also be collected from extracelluIlar fluids, extracellular supernatants from cell cultures, inclusion bodies in bacteria, cellular compartments, cellular periplasm, mitochondria compartment, etc.

In a preferred embodiment, the preparation of samples for the DMS-based analysis can be achieved by any method known to those of skill in the art. Sample preparation can include a desalting step to increase the sensitivity and resolution. In addition, as will be appreciated by those in the art, the combination of preparative steps, solvents, purification and separation schemes, will all depend on the class(es) of molecules expected to be detected.

Samples can be prepared in a variety of ways. One skilled in the art will readily determine the manner of sample preparation, which depends, generally on the source and the type of analytes expected to be detected. For example, physiological fluid samples can be prepared by a protein precipitation followed by a desalting treatment. A solution of methanol and water (49:49:2 water:methanol:acetic acid v:v:v) is added to each of the samples and the samples are chilled. This precipitates the proteins to the bottom of the tube. Each tube is then centrifuged and the supernatant decanted. For the desalting step, small amount (approximately 100 mg) of DOWEX ion exchange resin is added to each vial and allowed to sit for approximately 10 minutes. The sample is then centrifuged and the supernatant removed. This solution is then introduced to the an ion-mobility detection device.

Any solvent known to those of skill in the art can be used in conjunction with an ion source in the practice of the present invention. Examples of suitable solvents are dimethylsulfoxide, acetonitrile, N,N-dimethyl formamide, propylene carbonate, methylene chloride, nitromethane, nitrobenzene, hexane, methanol and water. The solvent can comprise more than one solvent. In a preferred embodiment, the solvent is a solution of methanol and water (49:49:2, water:methanol: acetic acid v:v:v). Selection of a suitable solvent will depend on the type of molecules is expected to be detected. For example, a solution of methanol and water is used as a solvent when the detection of soluble molecules is to be achieved by the ion-mobility device, while hexane can be used when the detection of apolar molecules such as lipids is to be achieved. In one embodiment of the invention, the sample source (e.g., tissues, cells) is extracted in different solvents and each extraction subjected to analysis, so that a more complete analysis of the molecules present in the sample source can be accomplished.

Samples can optionally be purified, fractionated and/or separated using any of the standard technique known in the art as described herein.

In addition, it should be noted that purification and separation techniques may be simultaneously or sequentially run on samples, in different orders and in different combinations. Thus for example, a simple protein precipitation may be run on a portion of the sample, and then a HPLC step. Similarly, portions of samples (e.g., portions of the cellular populations) may be subjected to different techniques in the elucidation or identification of peaks.

While one skilled in the art will appreciate that the method of the present invention can be practiced on a sample obtained from any of the sources mentioned above, application of ion-mobility analysis to detection and identification of urine constituents will now be described in details.

Urinalysis

An embodiment of the present invention provides a method of urinalysis using aspects of DMS ion mobility of the urine constituents.

Urinalysis is an examination of the urine by physical or chemical means. Urinalysis comprises a battery of chemical and microscopic tests that help to screen for urinary tract infections, renal disease, and diseases of other organs that result in abnormal metabolites appearing in the urine.

The following is a non-limiting list of indicators present in ice can be detected: bilirubin (a degradation product of hemoglobin); glucose; hemoglobin (an indication of hemolysis); urine ketones (a by-product of fat metabolism and present in starvation and diabetes); nitrite (an indication of urinary tract infection); urine pH (the acidity or alkalinity of the urine); urine protein; urobilinogen (a degradation product of bilirubin). In addition, pathogens such as fingi (yeasts), protozoa, bacteria and virus can be detected.

The results of the analyses are used for diagnosing the patients. Specifically, in some situations, an alkaline urine is good. Kidney stones are less likely to form and some antibiotics are more effective in the alkaline urine. There may be times when the acidic urine may help prevent some kinds of kidney stones and may prevent growth of certain types of bacteria. When blood levels of glucose are very high, some of the glucose may show up in the urine. The glucose and the ketones tests are usually done together. Large amounts of ketones may be present in uncontrolled diabetes. Finding protein in the urine is probably the best test for screening for kidney disease, although there may be a number of causes for an increased protein level in the urine. Bilirubin in the urine is a sign of a liver or bile duct disease. Urobilinogen is found in small traces in the urine. Nitrites and white blood cells are an indication that a urinary tract infection is present. Any vitamin C that the body does not need is excreted in the urine. If there are measurable amounts of Vitamin C in the urine, it may interfere with the other urine tests.

Volatile components of a urine sample are collected by directing a headspace to a DMS detection device. In another embodiment, urine sample is subjected to gas-chromatographic separation prior to DMS analysis. In an exemplary procedure, a gas chromatograph is maintained at an initial temperature designated as $T_0$. At the onset of analysis, designated as time $t_0$, the sample is introduced to the inlet of the gas chromatograph column. The temperature of the gas chromatograph is then elevated or ramped at a constant rate to a temperature $T_r$, reached at time $t_r$ at which all analytes have completed elution from the column. The column is further heated to a final temperature $T_f$, slightly elevated above $T_r$, at time $t_1$, and is held at this temperature to clean out the column. At the end of this final period, designated as time $t_2$, the chromatograph is cooled back down to the initial temperature $T_0$ for subsequent analysis, which cooling down is completed at a time $t_3$.

In addition to the above, every person emits a particular chemical odor, which may be used as a signature. This odor signature can be detected by DMS practices of the invention. The odor signature can be used to identify an individual for security applications, to identify bodies, and for covert applications to determine if a terrorist has been residing in a particular location based on signatures from urine or other residual odors left at the location. Such signature detection, based on detection of volatile chemicals, may be practiced according to the present invention.

Breath Analysis

An embodiment of the present invention provides a method of breath analysis. The present invention provides a method and apparatus that can measure and analyze both volatile and relatively non-volatile components released. Alcohols, such as ethanol, can be detected in exhaled air. Furthermore, understanding the composition of breath analysis can be used to diagnose diseases and elucidate pharmacokinetic properties of various compounds.

Alveolar breath is a distinctive gas whose chemical composition differs markedly from inspired air. Volatile organic compounds (VOCs) are either subtracted from inspired air (by degradation and/or excretion in the body) or added to alveolar breath as products of metabolism. Normal human breath contained several hundred different VOCs in low concentrations. More than a thousand different VOCs have been observed in low concentrations in normal human breath. (Phillips M: Method for the collection and assay of volatile organic compounds in breath, *Analytical Biochemistry* 1997; 247:272-278, the relevant parts of which are incorporated herein by reference).

Alkanes in breath are markers of oxygen free radical (OFR) activity in vivo. OFR's degrade biological membranes by lipid peroxidation, converting polyunsaturated fatty acids to alkanes which are excreted through the lungs as volatile organic compounds (VOCs); (Kneepkens C. M. F., et al., The hydrocarbon breath test in the study of lipid peroxidation; principles and practice, *Clin. Invest. Med.* 1992; 15(2):163-186).

For example, increased pentane in the breath has been reported as a marker of oxidative stress in several diseases including breast cancer (Hietanen E., et al., Diet and oxidative stress in breast, colon and prostate cancer patients: a case control study, *European Journal of Clinical Nutrition* 1994; 48:575-586), heart transplant rejection (Sobotka P. A., et al., Breath pentane is a marker of acute cardiac allograft rejection. *J. Heart Lung Transplant* 1994; 13:224-9), acute myocardial infarction (Weitz Z. W., et al., High breath pentane concentrations during acute myocardial infarction. *Lancet* 1991; 337:933-35), schizophrenia (Kovaleva E. S, et al., Lipid peroxidation processes in patients with schizophrenia. *Zh Nevropatol Psikiatr* 1989: 89(5): 108-10), rheumatoid arthritis (Humad S., et al., Breath pentane excretion as a marker of disease activity in rheumatoid arthritis, *Free Rad Res Comms* 198; 5(2):101-106) and bronchial asthma (Olopade C. O., et al., Exhaled pentane levels in acute asthma, *Chest* 1997; 111(4):862-5). Analysis of breath alkanes could potentially provide a new and non-invasive method for early detection of some of these disorders (Phillips M: Breath tests in medicine, *Scientific American* 1992; 267(1):74-79).

Breast cancer can be detected by identifying metabolic products of the cytochrome P450-mediated pathways. The cytochrome P450 (CYP) system comprises a group of mixed function oxidase enzymes which metabolize drugs and other xenobiotics. This system also metabolizes alkanes to alcohols e.g. n-hexane to 2- and 3-hexanol. The cytochrome P450 system is reportedly expressed in cancers of breast as well as other tissues (Murray G. I., et al., Tumor-specific expression of cytochrome P450 CYP1B1. *Cancer Res* 1997; 57(14): 3026-31). Recent studies suggest that exhaled pentane can be used as an additional marker for breast cancer. Hietanen et al. studied 20 women with histologically proven breast cancer and a group of age and sex-matched controls (Hietanen E., et al., Diet and oxidative stress in breast, colon and prostate cancer patients: a case control study, *European Journal of Clinical Nutrition* 1994; 48:575-586). Mean breath pentane concentration in the cancer patients (2.6 ppb, SD=2.8) was significantly higher than in the controls (0.6 ppb, SD=1.1, p<0.01). They did not report concentrations of pentane in ambient air, nor the alveolar gradients of pentane.

The methods and devices of the present invention can be particularly useful in diagnosing ischemic heart disease. There is an increasing body of evidence that myocardial oxygen free radical activity is increased in ischemic heart disease. Oxidative stress also increases during surgical reperfusion of the heart, or after thrombolysis, and it is related to transient left ventricular dysfunction, or stunning (Ferrari R.; et al., Oxidative stress during myocardial ischemia and heart failure, *Eur Heart J* 1998; 19 Suppl B:B2-11). Pentane was significantly increased in 10 patients with acute myocardial infarction compared to 10 healthy controls (Weitz Z W, et al., High breath pentane concentrations during acute myocardial infarction. Lancet 1991; 337:933-35). However, a fundamental flaw in the conventional breath pentane assays is that the column employed in the gas chromatograph does not separate pentane from isoprene, the most abundant compound in breath. The devices employed by the methods of the present invention can separate pentane and isoprene from one another Methods of the present invention can be used as non-invasive techniques to diagnose organ rejection, including heart. There is a well-documented biochemical basis for breath testing that provides for the early detection of transplant rejection. Tissue damage arising from inflammation is accompanied by an accumulation of intracellular oxygen free radicals (OFR'S) which cause lipid peroxidation of lipid membranes (Kneepkens C. M. F., et al., The hydrocarbon breath test in the study of lipid peroxidation: principles and practice. *Clin Invest Med* 1992; 15(2):163-186. Kneepkens C. M. F., et al., The potential of the hydrocarbon breath test as a measure of lipid peroxidation. *Free Radic Biol Med* 1994; 17:127-60). This process is accompanied by the evolution of alkanes which are excreted in the breath. One of these alkanes, pentane, is the best documented marker of OFR activity. Methods of the present invention can be employed to detect breath pentane in transplant recipients.

End-stage renal disease (ESRD) is a fatal condition unless it is treated with either kidney transplantation or dialysis of blood or peritoneal fluid. Clinicians who come into contact with patients with chronic renal failure are familiar with the classic odor of uremic breath. It has been variously described as "fishy", "ammoniacal" and "fetid". This odor arises from presence of trimethylamine and dimethylamine in the blood, as well as increased concentrations of secondary and tertiary amines. Methods of the present invention can be used to detect these compounds, thus indicating the presence of ESRD.

Additionally, presence of methylated alkanes are common components of the breath in normal humans as well as in those suffering from lung cancer. Phillips M., et al., Variation in volatile organic compounds in the breath of normal humans. *Journal of Chromatography* B 629 (1-2): 75-88; 1999; Phillips M., et al., Volatile organic compounds in breath as markers of lung cancer: a cross-sectional study. *Lancet* 353:1930-33; 1999. These VOCs appeared to provide additional markers of oxidative stress. Methods and devices employed by the present invention can be used to create patient's methylated alkane profile and thus serve as additional tool in early lung cancer diagnosing.

Various personal odors may be detected in practice of the invention, such as breath or arm pit or the like. In another embodiment, the present invention is a breath test which can be used to determine the characteristic of metabolism of a drug in a subject. Specifically, the present invention can be used to determine this characteristic of metabolism by measuring the concentration of a metabolite in the exhaled breath of the subject after an appropriate amount of the drug has been administered to the subject. Hereinafter, the term "characteristic of metabolism" includes whether such metabolism occurs, the rate of metabolism and the extent of metabolism. However, for clarity the aforementioned and following descriptions specifically describe the measurement of the rate of metabolism. Generally, these tests involve the administration of a substrate to the subject and the measurement of one or more cleavage products produced when the substrate is chemically cleaved.

For example, detecting *Helicobacter pylori*, which produces a large quantity of the enzyme urease, can be accomplished by orally administering urea to a subject with subsequent monitoring of the exhaled dioxide and ammonia.

Breath tests can be used to measure physiological processes such as the rate of gastric emptying. For example, gastric emptying rates were measured for solids and liquids by using octanoate or acetate as the substrate (Duan, L.-P., et al., *Digestive Diseases and Sciences*, 1995, 40:2200-2206). The substrate can be administered to the subject and the exhaled breath of the subject was measured with an ion-mobility detection device.

The breath test of the present invention can be performed as follows. First the drug is administered to the subject. Next, the exhaled breath of the subject is analyzed after a suitable time period for a concentration of a metabolite of the drug, the concentration indicating the rate of metabolism of the drug in the subject. Such a breath test has a number of advantages over conventional methods for determining the concentration of a drug in the subject. Not only is a breath test non-invasive, it is also more rapid than analyzing blood samples and it can also be performed multiple times on the subject.

In one embodiment, the present invention provides a method and apparatus that can measure and analyze components released from food or other products during oral processing. An optional step of volatilization is employed should detection of non-volatile components is desired. This method can be used to measure components that are present in small concentrations, yet are important to the flavor of a product.

Illustrative embodiments of breath sample collection techniques will now be described. In one embodiment, the collection system included a mouthpiece and a tube for carrying the exhaled breath of the subject into a mixing chamber. A sample outlet and exit tube connected the mixing chamber to a measuring device, such as DMS detection device. In addition, heat can be applied to the system to prevent condensation of moisture from the breath sample on the system components. The mixing chamber can be provided to insure that the exhaled breath sample mixed with previous samples, and that a small quantity of the combined breath sample was drawn from the chamber into the measuring device.

In another embodiment, the collection system uses a pumping system to draw an air sample from the nose of a subject, through a nose-piece and past a membrane separator fitted to a DMS detection device.

In yet another embodiment, a carrier gas, e.g. $N_2$, and a breath sample can be injected into a separating column, e.g. GC, and then circulated toward an ion-mobility detection device.

In another embodiment, the collection system described in U.S. Pat. No. 5,479,815. In this system, the subject exhales a breath sample into one or more collection chambers that are preferably maintained in a temperature controlled cabinet to prevent condensation of portions of the sample. Either mouth-exhaled or nose-exhaled air can be collected. Where food flavorings are being detected, samples are preferably collected from the subject's mouth. Each breath sample can be purged from its collection chamber with a non-reactive gas flow into a trap containing an interface that separates and collects components from the breath sample. This interface preferably is an inert adsorbent material selected for its ability to. A substrate coated with an absorbent or other material capable of collecting components may also be used. The interface, in addition, preferably permits any moisture contained in the breath sample to pass through the trap, leaving only the collected components on the interface.

The adsorbent trap is then transferred to a thermal desorber or other device capable of releasing the adsorbed components from the interface surface into a measuring and analysis apparatus, such as an ion-mobility based detection device of the invention. In one embodiment, the components collected by an adsorptive trap are thermally desorbed from the trap and flushed into a gas chromatograph by a non-reactive gas flow prior to being identified by an ion-mobility detection device.

In another embodiment, the subject blows each breath sample first through a condensation trap and then into the collection chamber. The condensation trap captures relatively non-volatile flavor components that might not otherwise be recovered from the collection chamber or could not be readily desorbed from an adsorbent trap. The condensation trap preferably includes non-reactive glass tubing packed with a non-reactive and non-adsorbent substrate, such as glass wool. Other materials may be used provided that the materials withstand high temperatures and do not react with flavor compounds. The trap is maintained at a temperature that will encourage the condensation on the substrate of slightly volatile or relatively non-volatile flavor components in the subject's breath and permits the volatile components to pass through into the collection chamber.

The condensation trap is then heated to re-vaporize the condensed components, so that they may be purged into measuring and analysis devices such as a gas chromatograph and mass measuring device. Similarly, the flavor components that passed through the condensation trap into the collection chamber also may be flushed into an adsorbent trap so that they may be studied as discussed above.

Quality Control of Foodstuff and Food-Processing Surfaces

The present invention can be used in the detection of chemical contaminants and/or viable pathogens that may be present in processed foods, such as found in ground beef and other meats. The ability to rapidly confirm or disprove the presence of significant contamination may, for example, reduce or eliminate the need for destruction or recall of ground meats or other foods in cases where contamination was possible but not certain by demonstrating that the meats or other foods in question are not contaminated with viable bacteria at the time of testing.

The present invention can be used in food processing plants, hospitals, laboratories, and other facilities to determine whether surfaces are free of pathogens or whether additional or more stringent sterilization or containment procedures are required. This can be achieved by, for example, collecting a sample of dust or a cotton swab of a surface in question, followed by either re-suspending the sample material in a fluid or immediate volatilization. The volatilized sample is subjected to detection as described herein.

The present invention can further be used to identify contaminated food containers by collecting either a sample of a headspace or a swab of a surface.

In one embodiment, the present invention can be used for detection of substances in a foodstuff industry. Both odorous (relatively volatile) and non-odorous substances (relatively non-volatile) can be detected, the latter with an additional optional step of volatilization being required before the sample being directed into a DMS device.

The detection of odorous substances has many industrial applications, especially in processes in the foodstuff industry, in which one can, for example, determine the degree of freshness and the quality of the products, due to the odorous substances which they release. Gas chromatography, which consists in a method of separating the molecules of gas compositions, can be used as a way of pre-separating components of a sample prior to detection by DMS.

A method for detecting odorous or volatile substances or substances made volatile, comprises the steps of directing an air sample collected in the proximity of a food substance or a food-handling surface to DMS detection device.

This method can advantageously employ sample collection techniques described in U.S. Pat. No. 5,801,297. In particular, the transport of the odorous substances from a sample can be achieved by a variable controlled flow of gas. This allows for very rapid detection of odorous substances, in about a few seconds. The means used in order to achieve this variable controlled flow of gas are advantageously made up of at least a pump with variable flow rate. During the phase of separating and detecting the components of a sample, the gas flow rate can be diminished or increased according to whether the substances become more or less volatile throughout the duration of the measurement period.

Smart DMS Smoke Detector

The present invention can be used for identification of a fuel source by analyzing smoke. Where a gas chromatography device is used to pre-separate the smoke components, GC-DMS instrument operating at ambient pressure in air provides a compact and convenient fuel-specific smoke alarm at a reasonable cost. The specificity and sensitivity of the system earns the moniker of a "smart DMS smoke detector".

One embodiment of the present invention provides a smart smoke detector with high specificity by detection of volatile organic constituents (VOCs) in the smoke. Fires produce a large number of organic compounds in complex mixtures in the vapor phase as seen in fires from synthetic polymers, cigarettes, and cellulose-based materials such as wood or cotton. This approach provides sufficient analytical information for selective detection of fire components through measurement of the chemical composition of the emissions.

Illustrative Differential Ion Mobility Devices of the Present Invention

An illustrative practice of the invention is shown as system 10 in FIG. 1, in which a sample A and transport fluid B are delivered to a filter C (operating by aspects of ion mobility), wherein the ionized sample $S^{+/-}$ is filtered by ion species according to aspects of ion mobility. Thus a selected ionized species is outputted from the ion filter ("separator") and may be further processed in part D. This further processing may include being detected to indicate presence of a biological material in the sample, and/or may include being collected and used as a biological material extracted from the sample. The sample itself may be delivered already including ion species of interest.

The sample is ionized in ionization region E before it enters the filter part C. In one alternative embodiment, region E receives the sample and transport fluid where they are mixed together in mixing region E1 in presence of an ionization source E2, or are mixed with an additional ionized fluid flow from source E2, all to provide the ionized sample $S^{+/-}$ that is delivered from region E to filter C. Filter C is preferably a DMS filter.

In a preferred illustration of the invention, an analyte is detected based on differences in mobility of the ionized analyte in a DMS electric filter field. Preferably, this field analysis includes high field asymmetric waveform ion mobility spectrometry-type differential ion mobility, as described in U.S. Pat. No. 6,495,823 or U.S. Pat. No. 6,512,224, and generally described herein as DMS. These patents teach both gas transport of ion species and electric field ion transport of ion species, which may be practiced in embodiments of the present invention.

In one practice of the invention, a DMS filter (separator) is tuned to pass a specific analyte of interest, and the passed analyte is then collected or processed accordingly. In another practice, the filter field is scanned through a range that enables detection and identification of a range of ion species that are present in the sample, including positive and negative species. This spectrum can be detected for a full characterization of the detected sample.

Figure 2A:
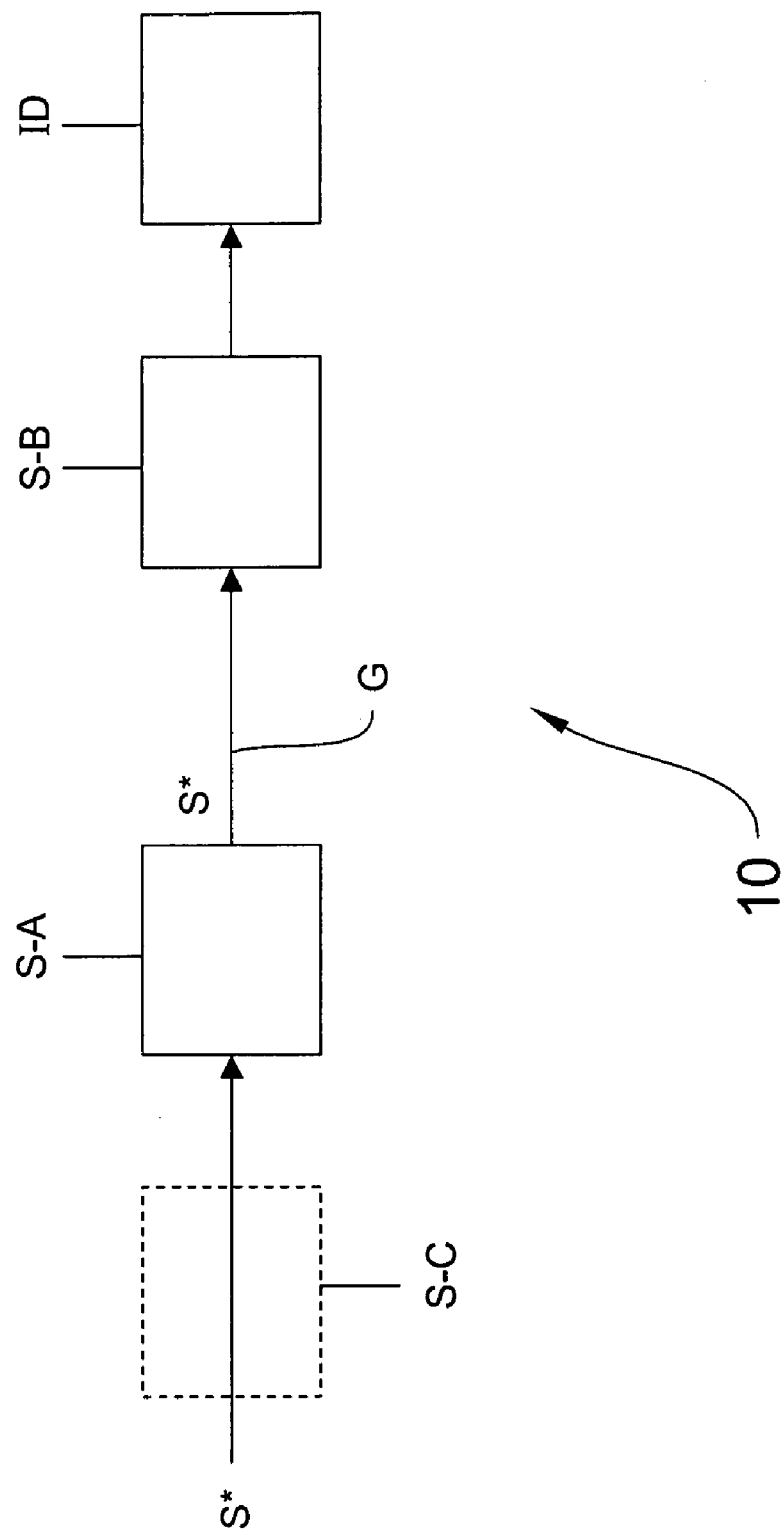
FIG. 2A is a schematic diagram of a separation system of the invention.

A further practice of the invention is shown in FIG. 2A wherein system 10 includes separation sections "S-A" and "S-B" followed by identification section "ID". In operation a complex sample S* can be separated in first section S-A and the separated sample flow S is then applied to the second section S-B for further separation/processing. The result of both separations and the related S-A and S-B data is correlated and enables reliable identification of separated components from the complex sample. The output of section S-B is evaluated in the identification section ID.

It will be understood that a preferred process of the invention includes using DMS to generate separation data and at least one other processing step that yields its own separation data. This additional separation step may be before or after DMS filtering. The combination of detection data leads to highly reliable identification of ion species present in a complex sample even at trace levels. In a preferred embodiment, the first separation section S-A includes a gas chromatograph (GC) and the second section is a DMS filter.

Accordingly, in one embodiment, the present invention is an apparatus and a method for detection and identification of analytes in a sample by aspects of ion-mobility based detection. In this embodiment, a portion of a sample is directed into a first separation device, thereby obtaining a first profile of a sample. A portion of a sample is also directed into a second separation device thereby obtaining a second profile of a sample. At least one of the first and the second separation devices is a DMS device. As used herein, a "profile" includes any data obtained by a separation device, such as, for example, any ion-mobility signature, such as DMS mobility, time of flight, mass spectra, chromatographic retention time and the like. One skilled in the art will determine specific data comprising a profile based on the nature of the sample to be analyzed and the separation device employed by a specific embodiment of the apparatus and a method of the present invention.

The first and the second profiles obtained above are combined, thereby allowing identification of at least one analyte in a sample. The combination of profiles can be done by way of comparison of the two profiles, whereby the presence of a particular analyte can be confirmed. The combination can further include adding the data obtained by a first separation device to the data obtained by the second separation device.

Figure 2B:
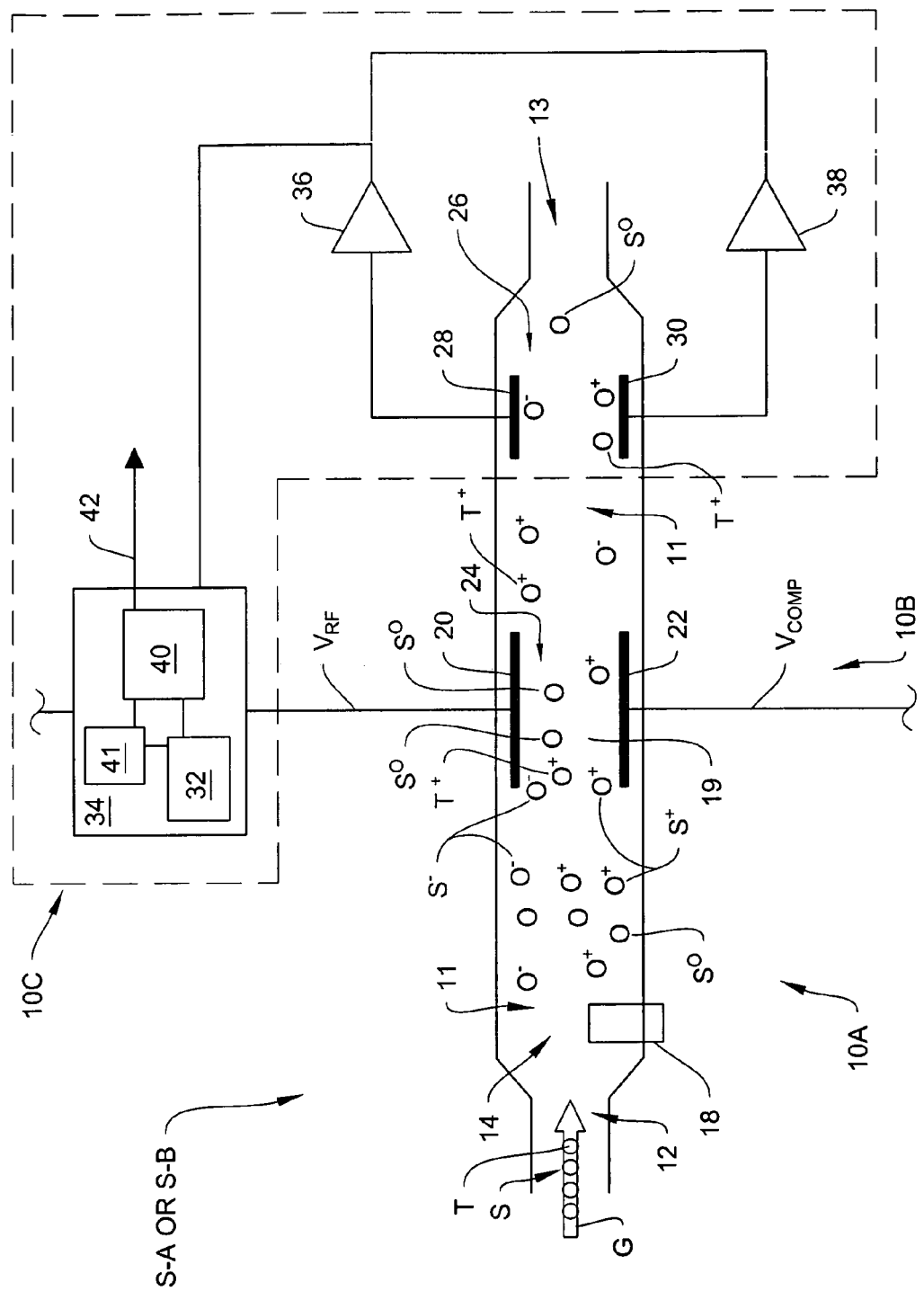
FIG. 2B is a schematic diagram of an analysis system of the present invention.

The DMS practice of the invention may include a DMS filter in either or both separators S-A or S-B. A preferred DMS system is shown in FIG. 2B, including a sample input section 10A, a DMS ion filter section 10B. The DMS output is evaluated in the detection and identification section 10C in FIG. 2B (which constitutes the identification section ID of FIG. 2A), which includes an intelligent controller/driver provided by command and control unit 34.

Typically, a memory or data store 33 is used to record separation or mobility signatures for known ion species and the apparatus is enabled with this data. The DMS detection data can be correlated with the field conditions data (e.g., RF characteristics, compensation, flow rate, temp., etc.) and forms a detection dataset for the detected ion. The detection dataset is compared to a signature dataset(s) for known ion species as stored in the data store. A match enables identification of the species of the detected ion. In one embodiment, the data store includes associated characteristic retention time data and data that relates to use of other separation techniques (such as a thermally controlled SPME prefilter).

The detection is both qualitative and quantitative. For example, upon detection of an ion associated with an anthrax molecule, a match with the stored data will enable identification of the detected species as "anthrax" and with an indication of detection level based on the intensity of detection. Such an indication may be issued as a warning to a display or other output device.

The DMS RF signal is generated and the compensation bias is applied to filter electrodes 20, 22 by drive circuits 32 within command and control unit 34. Preferably a detector 26 is provided, and preferably a charge detector (e.g., Faraday type detector), including detector electrodes 28, 30. As ions contact they detector electrodes they deposit their charges and these detection signals are then amplified by amplifiers 36, 38, all under direction and control of unit 34. Preferably a computer or microprocessor 40 correlates drive signals applied to the filter electrodes with detection signals from amplifiers 36, 38, and makes a comparison to stored data in data store 41, and then issues identification data 42 to a readout device, such as for indication of detection of the target molecule.

In one embodiment, a GC output of section S-A delivers sample S as an eluant that is carried by a drift or carrier gas G into flow channel 11 at inlet 12. The sample S flows toward a sample outlet 13 at the other end of flow channel 11. Sample S may include various molecules including trace level analyte T. The sample may be delivered directly from the GC (or in other embodiments may be delivered via a nebulizer, spray head, etc.), and flows into ionization region 14. Molecules in the sample are then ionized by ionization source 16.

The result of ionization is ionized analyte ions T+/− and other ions S+, S− with some neutral molecules S°, as may be derived from various chemical species that are in sample S. These ions may appear as monomers, dimers, clusters, etc.

The ions and neutral molecules is flowed into the ion filter section 10B for analysis. The carrier gas carries the ionized sample into the analytical gap 19 formed between electrodes 20, 22 of filter 24. In a preferred embodiment of the invention, filtering proceeds based upon differences in ion mobility in an asymmetric RF filter field alternating between high and low field values. This filtering reflects unique mobility characteristics of the ions as species; the process enables discrimination of species based upon mobility characteristics in the field which reflects ion size, shape, mass, charge, etc.

In accordance with an illustrative embodiment of the present invention, an asymmetric field voltage, Vrf, applied across the filter electrodes 20, 22 generates a field F (e.g., 10,000 V/cm) whose strength alternates between high value Vmax and low value Vmin. This variation in the field strength causes the ions to move transverse to the sample flow in the flow channel, with the transverse motion being representative of the characteristic field mobility of the ions.

The mobility in the high field condition differs from that of the low field condition, and this mobility difference produces a net transverse displacement of the ions as they travel longitudinally through the filter field between the electrodes, resulting in an ion trajectory over time. This trajectory will drive the ions into the filter electrodes, causing them to be neutralized, lacking a countervailing compensation.

A compensation, such as a DC compensation voltage Vcomp, is applied to the filter to differentially compensate this transverse motion. The compensation will compensate the transverse motion of a selected ion species and will cause it to return to the center of the flow path based on its compensated mobility characteristics. Thus this returned ion species is able to exit the filter without colliding with the filter electrodes and without being neutralized.

In this process other species will not be sufficiently compensated and will collide with the filter electrodes 20, 22 and will be neutralized. The neutralized ions T° are purged by the carrier gas, or by heating the flow path 11, for example.

A compound may be represented by either or both positive and negative ions ("modes") such as T+ and T−, as such modes may be generated by ionization of the analyte molecules T. In a preferred embodiment, both positive and negative modes of an ionized species can be simultaneously detected in detection and identification section 10C. In this case, detector 26 includes biased detector electrodes 28, 30 that are capable of simultaneous detection of modes simultaneously passed by the DMS filter.

The in-line configuration of the flow path enables both modes of a species generated during ionization to flow into the DMS filter 24. The DMS filter passes these modes during a mobility scan, where each is the passed species when the scanned field conditions are appropriate. Thus analyte T may produce ions T+ and T− which each will pass through the filter at the appropriate signature field conditions.

In practice of the invention, ion species are filtered based on mobility differences. Therefore in a preferred practice of the invention, all ions of an ion species will be passed on for detection, whether positive or negative ions, and which may be detected simultaneously. Accordingly the detector electrodes are biased so that one attracts the positive and the other attracts the negative ions. Thus, in an embodiment of such arrangement both "positive mode" and "negative mode" ions of a species are detected simultaneously. Having both modes from a single detection provides a more unique signature for the detected ion species and therefore increases the potential accuracy of species identification of the invention. The benefit of mode detections is further discussed below.

In a practice of an embodiment of the invention, the ions flow to the detector wherein electrode 28 may be biased positive and electrode 30 biased negative, and therefore electrode 28 steers the positive ions T+ toward electrode 30, and results in ions T+ depositing their charges on electrode 30. Meanwhile, electrode 30 acts as a steering electrode and steers the negative ions T− toward electrode 28, and results in ions T− depositing their charges on electrode 28. It is a feature of this embodiment that both + and − ion modes may be detected simultaneously. Single mode or dual mode detection data is combined with filter field parameter data and is then compared to stored data to make an identification of the detected analyte T, and this is combined with the separation data representing the first separation to enable highly reliable identification of the analyte of interest, even at trace levels.

Figure 2C:
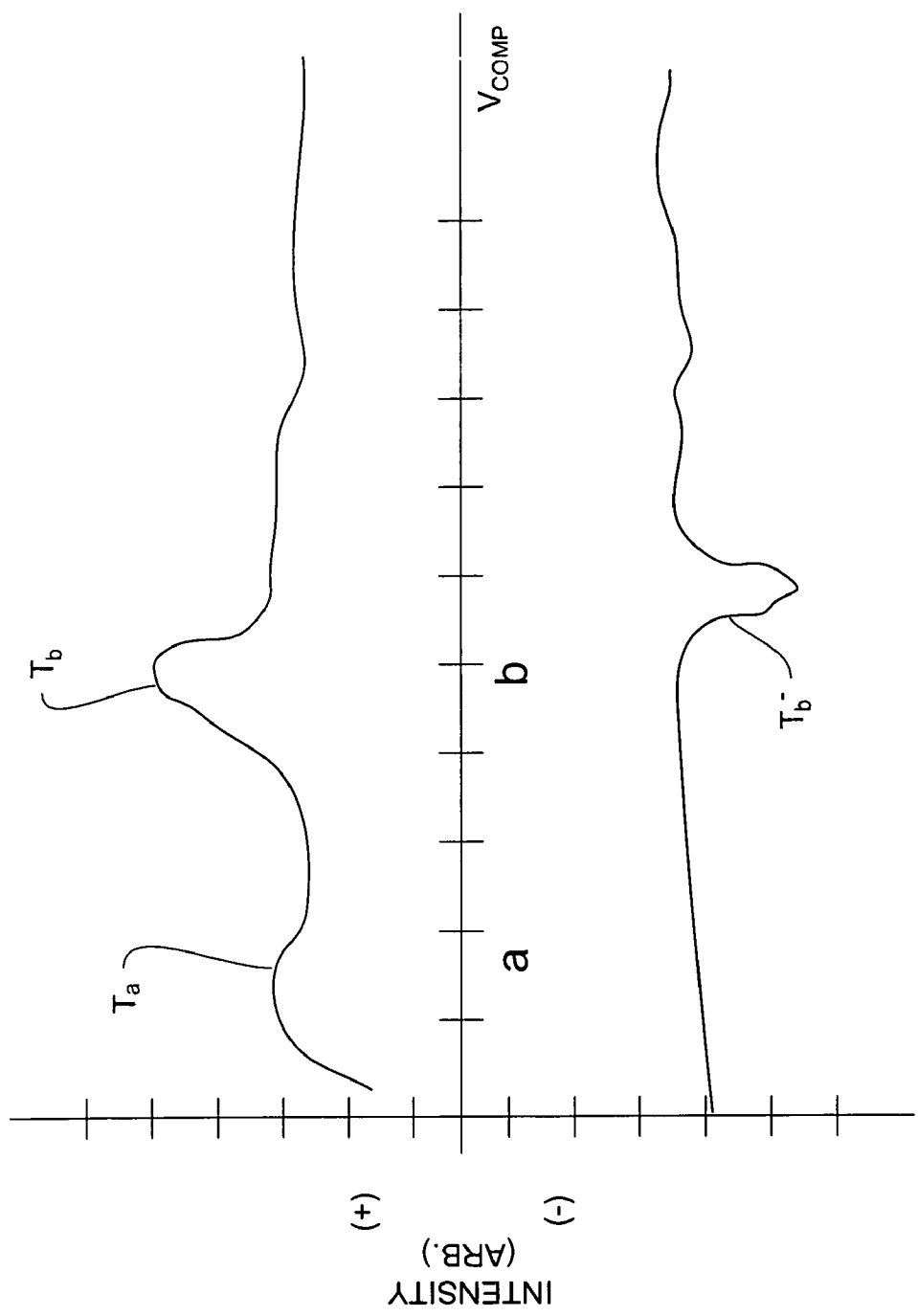
FIG. 2C shows a detection scan according to the invention.

In accordance with the present invention, discrimination of ions from each other according to mobility differences is achieved wherein the RF field and the selected compensation enables a particular ion species to pass though the filter. A plot of detection intensity versus compensation for a given field strength is shown in FIG. 2C, where peaks Ta, Tb indicate intensity of the detection signal at compensation levels a, b for the particular RF field. Peak "Ta+" represents the "analyte Ta" positive mode, and peak "Tb+" represents "analyte Tb" positive mode. Peak "Tb−" represents "analyte Tb" negative mode. The intensity of the peak may be correlated with detection quantity. Furthermore, the retention time associated with these peaks can be correlated with the peaks to improve reliability of species identification.

In a simplified aspect of the invention, a first separator S-A (e.g., a fast GC) is coupled with to a second separator S-B (e.g., DMS filter), as in the arrangement of FIGS. 2A and 2B. In a preferred embodiment, a pre-filtering step is provided by a front-end collector system S-C (shown in dotted outline) to enable a highly reliable, selective and sensitive advanced chemical detector system. In practice of the invention, various analytes that are difficult to discriminate and detect can be identified with confidence.

For example, the sample can be collected, such as by means of solid-phase micro-extraction (SPME) media, in pre-collector part S-C, and then delivered to a GC, in separator S-A, for further separation and followed by DMS separation in part S-B and species identification in part ID, according to the invention.

SPME uses a fiber or tube having coating material which preferentially adsorbs analytes from a sample matrix and delivers the analyte for further processing. SPME is routinely applied to gas-phase liquid-phase extractions, such as for extracting organic analytes from a sample and delivering same for chromatographic analysis. The preferred embodiment enables delivery of a volatilized or volatilized sample which can be processed in gas phase.

Figure 3:
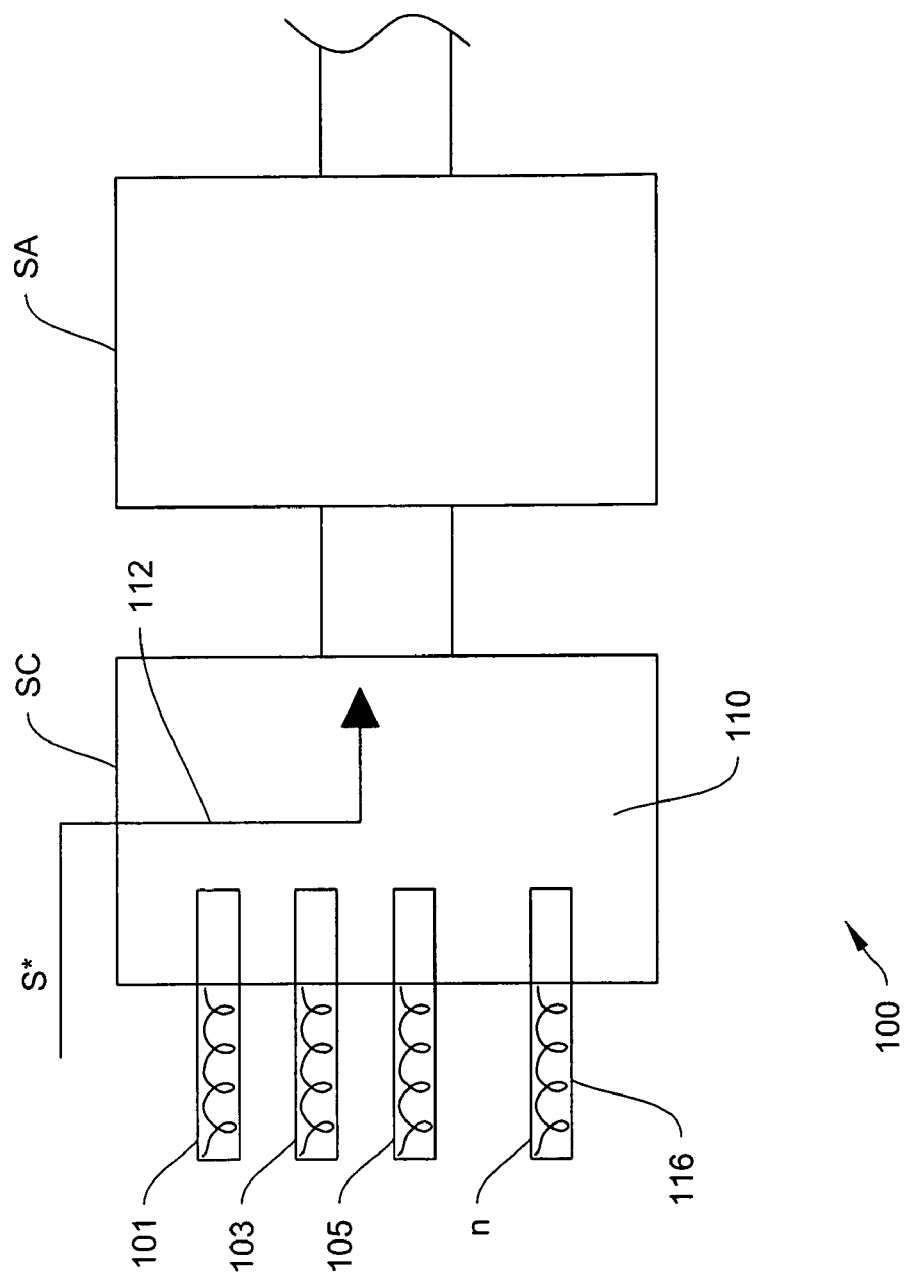
FIG. 3 is a schematic diagram of a separation system of FIG. 2A that includes an SPME pre-separator.

Embodiments of the present invention enable provision of intelligent monitors for a variety of application. For example, smart air monitors, smoke detectors and the like can be provides. Programmable control of the separation sections or selection of dedicated components enables tailoring a system to particular needs. An illustrative embodiment of this invention enables an advanced environmental detector of reasonably high analytical performance. In this embodiment, a SPME collector system 100, shown in FIG. 3, which provides a pre-filter front-end (see separation section S-C) and delivers sample S to the GC (separation section S-B) and then the DMS section S-B proceeds as described.

The SPME collector system 100 preferably has several SPME collectors 101, 102, 103 . . . n. which are selected for special characteristics. For example, all may be designed to selectively deliver a particular type of analyte or a range of analytes into collector 110.

The SPME fibers introduce the sample S into collector 110. In one embodiment, a drift gas 112 is introduced into collector 110 and carries the sample S introduced by the SPME fibers to the separator S-A (e.g., GC). Now further separation, filtering, detection and identification proceeds as earlier described.

This SPME sampling may include the step of heating the SPME fibers to purge VOCs, or to pyrolyze/volatilize a sample that then is delivered into collector 110 and then for further processing such as by GC-DMS. The heating may be provided by heaters 116 associated with the SPME absorber fibers 101, 103, 105, etc. The system is controlled by controller 34.

The heaters may be switched on and off and in this manner can control sample delivery within a desired range of chemical compounds according to the characteristics of the switched SPME fibers. For example, upon detection signal, one or a series of the fibers 101-n can be heated to change the sample absorption profile and delivery characteristics. Heaters 116 can also be used to heat the fibers for purging of same or even for pyrolysis of the samples. Such heating can be ramped to create a desired profile.

In one embodiment, the present invention provides detection of smoke and intelligent discrimination of components in the smoke. The chemical composition of smoke from sources of interest exhibit measurable chemical differences that can be analyzed by the SPME-GC-DMS system. A remarkable level of reproducibility for complex chemical process (i.e., combustion of natural materials) was obtained using simple sampling methods. In a further embodiment, monitoring changing vapor composition with time of burn and detailed identification of volatile products from combustion is used in an augmented method of the invention.

It will be appreciated that the present invention is not limited to detection/discrimination of smoke. More broadly, the present invention enables analysis of compounds by including differential ion mobility analysis in compensated high field asymmetric waveform ion mobility RF fields in a compact package that can be manufactured using high volume techniques that result in low per costs and yet produces results comparable to expensive analytical equipment. Systems according to the invention can be light-weight and yet provide the ability to provide highly effective analytical equipment whether in the field or in the laboratory.

Devices of the invention are able to rapidly produce accurate, real-time or near real-time, in-situ, orthogonal data for identification of a wide range of chemical compounds. Devices of the invention, such as devices according to FIG. 2A through 2C and FIG. 3, enable distributed installation of detection systems such as can serve heating and air conditioning systems (HVAC), where air quality monitoring and/or flow control and mixing of interior and outside air is of interest. Such HVAC system can be controlled by a central controller (e.g., controller 34), to meet user needs automatically or on demand.

DMS devices of the invention may incorporate various electrode configurations, including coaxially or non-coaxially cylindrical, curved, curvilinear, arcuate, radial, plate, parallel, planar or flat. These configurations may be focusing or non-focusing as practiced in DMS devices. A preferred practice of the present invention is generally referred to as "plate-type", and it will be understood embodiments may use facing electrode portions, segments, sections, or plates. In one embodiment, non-uniform focusing fields are generated between the DMS filter electrodes; such embodiment may include a curved flow path including flat, non-flat or curved DMS electrodes.

Figure 4A:
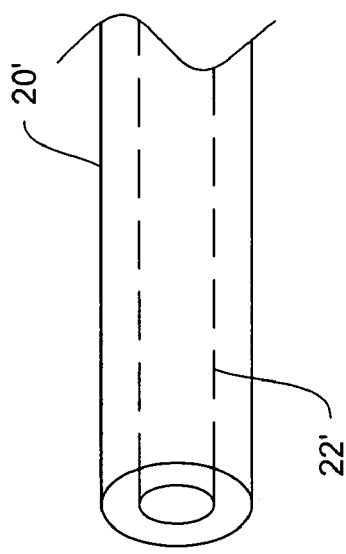
FIG. 4A is a schematic diagram of an embodiment of the present invention with a cylindrical arrangement of the electrodes of a DMS system.
Figure 4B:
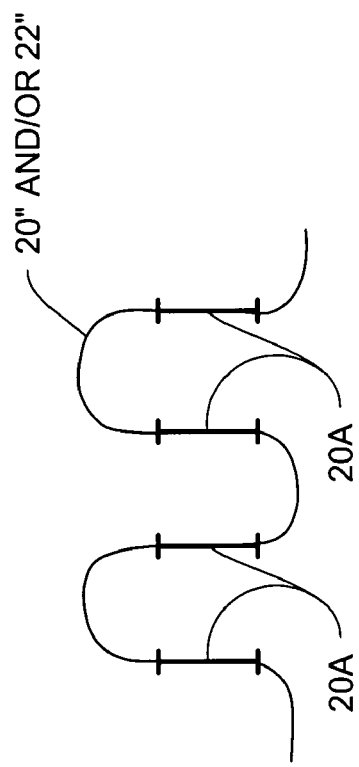
FIG. 4B shows one embodiment of DMS electrodes where the electrodes are curved or curvilinear.

Turning now to FIG. 4A and FIG. 4B, alternative embodiments of electrodes 20 and 22 are shown. As shown in FIG. 4A, filter electrodes, labeled 20' and 22', can be coaxially cylindrical. In another embodiment, shown in FIG. 4B, either one or both electrodes, labeled 20" and/or 22", can be curved or curvilinear. In particular, segments 20A can be curved, thereby producing a focusing effect known in the art, or straight, thereby producing a field substantially similar to that produced by the electrodes 20 and 22 as shown in FIG. 2B. In the embodiment where segments 20A are straight, their length can be variable.

Device for Detection of Analytes in a Volatilized Sample

In one embodiment, the present invention is an apparatus for detection and identification of analytes in a volatilized sample using the mobility-based signature obtained by a differential ion mobility spectrometry (DMS) device.

Figure 5:
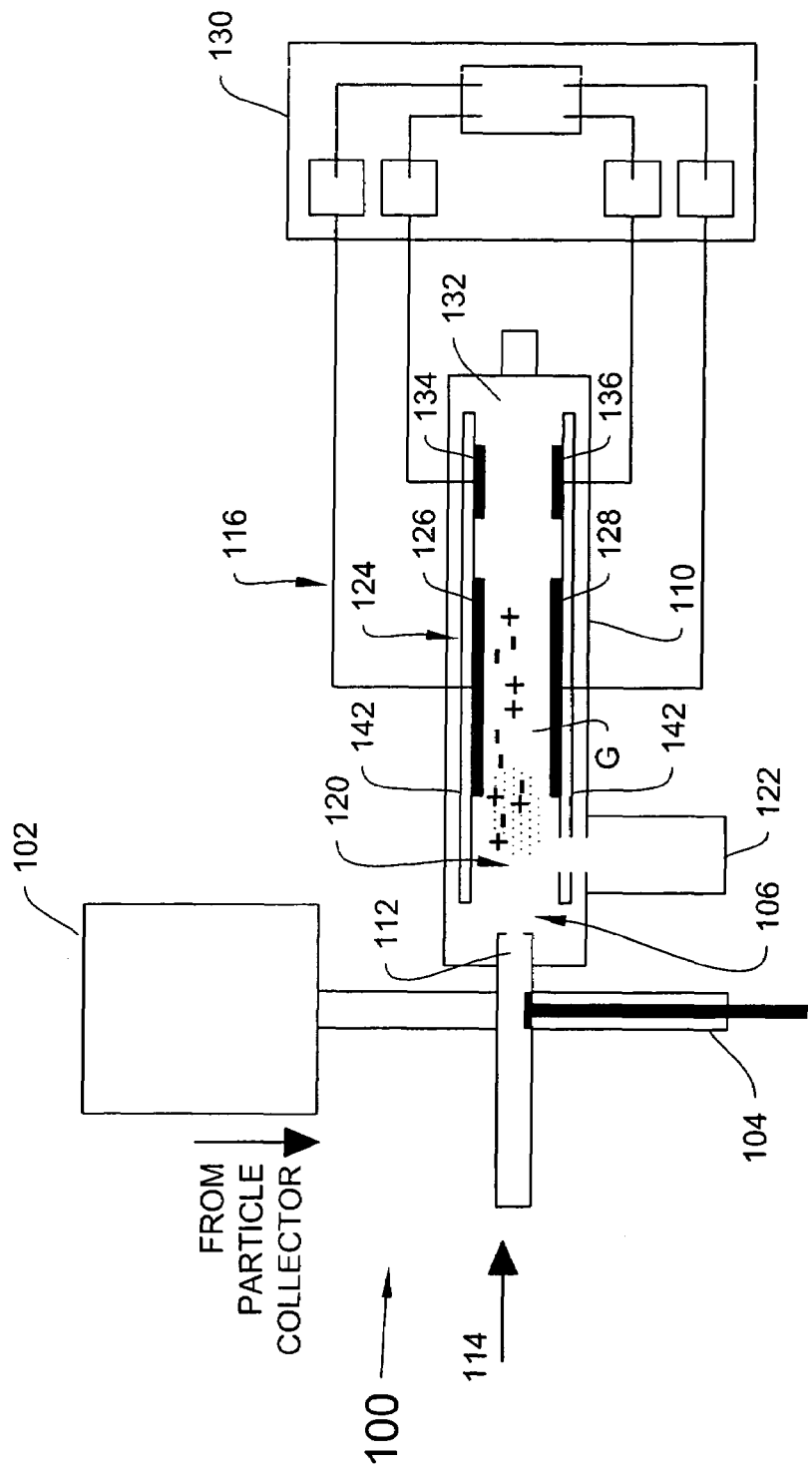
FIG. 5 is a schematic of an embodiment of the invention with a pyrolysis front-end.

Referring to FIG. 5, an illustrative pyrolysis-based DMS system device of the invention will now be described. It is understood that any of the volatilization techniques described herein can be adapted for use with the instant invention.

In this embodiment, system 100 includes a sampler or other particle collector 102 which delivers liquid or solid sample to a pyrolyzer 104 (such as a commercially available pyrolyzer from CDS Analytical) which has an output coupled to the flow path 106 of the DMS analyzer 110. The flow path structure (sometime referred to as a drift tube) has an inlet 112 for receipt of the pyrolyzed sample output from the pyrolyzer carried by carrier gas 114. The pyrolysate in transferred from the pyrolyzer to the DMS through a sealed and heated interface. During sample loading on the probe, the pyrolysis chamber is purged while a stream of clean N2 is diverted into the DMS. During pyrolysis, the flows are diverted through a valve into the analyzer to assist introduction of the pyrolate.

In one example, the pyrolyzer heated samples from room temperature to 1400 C at rates from 10-20° C./msec. The controlled temperature ramping enables selective desorption of compounds from the probe, therefore enhancing resolution and signal-to-noise of the apparatus. A drying function evaporates and vents the solvent out a purge vent resulting in sample concentration and prevention of the solvent from entering the DMS analyzer 110. A probe cleaning function, flash-heats and desorbs left-over sample between analyses.

The pyrolate is carried by the carrier gas into the ionization chamber 120 where source 122 ionizes the sample. The ions ("+", "−") are carried by the carrier gas into the filter 124 between filter electrodes 126, 128. In a preferred practice of the invention, an asymmetric high-low varying RF field is generated between the filter electrodes, with applied DC compensation, under control of controller/driver 130. Ion species are passed to the detector 132 based on compensated field conditions and mobility difference for the species. As the compensation is scanned, a spectrum can be recorded for the sample. Detector 132 includes electrodes 134, 136, which enable detection of positive and negative modes for each species.

In a preferred embodiment, electrodes 124, 134 are formed on a substrate 140 and face electrodes 126, 136 formed on substrate 142. Preferably the substrates are insulating. The substrates are mated to fix the distance between the electrodes and defining the analytical gap G between the electrodes (preferably ~0.5 mm). The asymmetric field is generated between these electrodes transverse to the analytical gap and the ions are flowed in the gap through the field.

Additional Illustrative Embodiment of DMS Practices of the Present Invention

Figure 6:
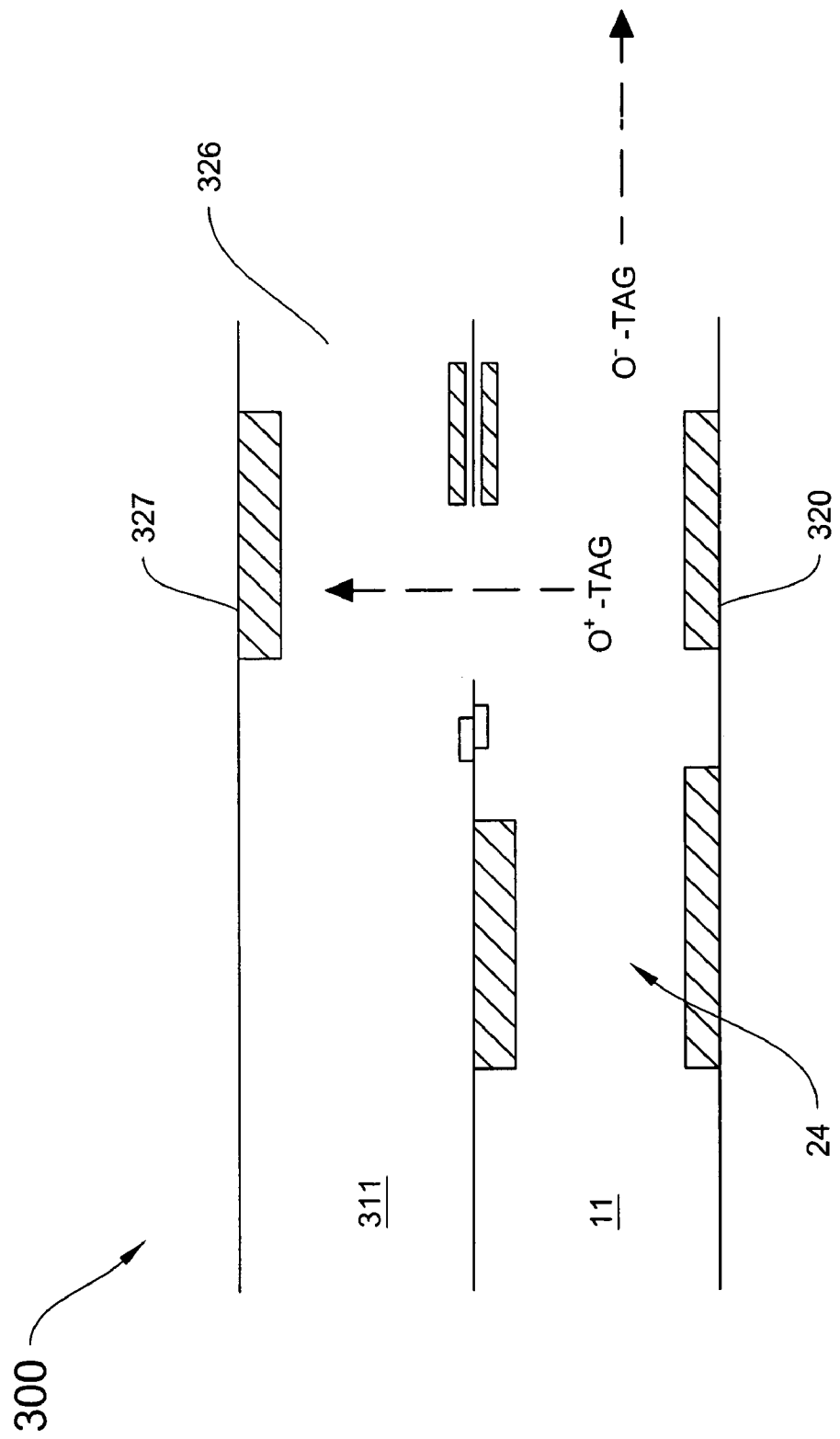
FIG. 6 is a schematic diagram of an alternative separation method of the present invention.
Figure 7:
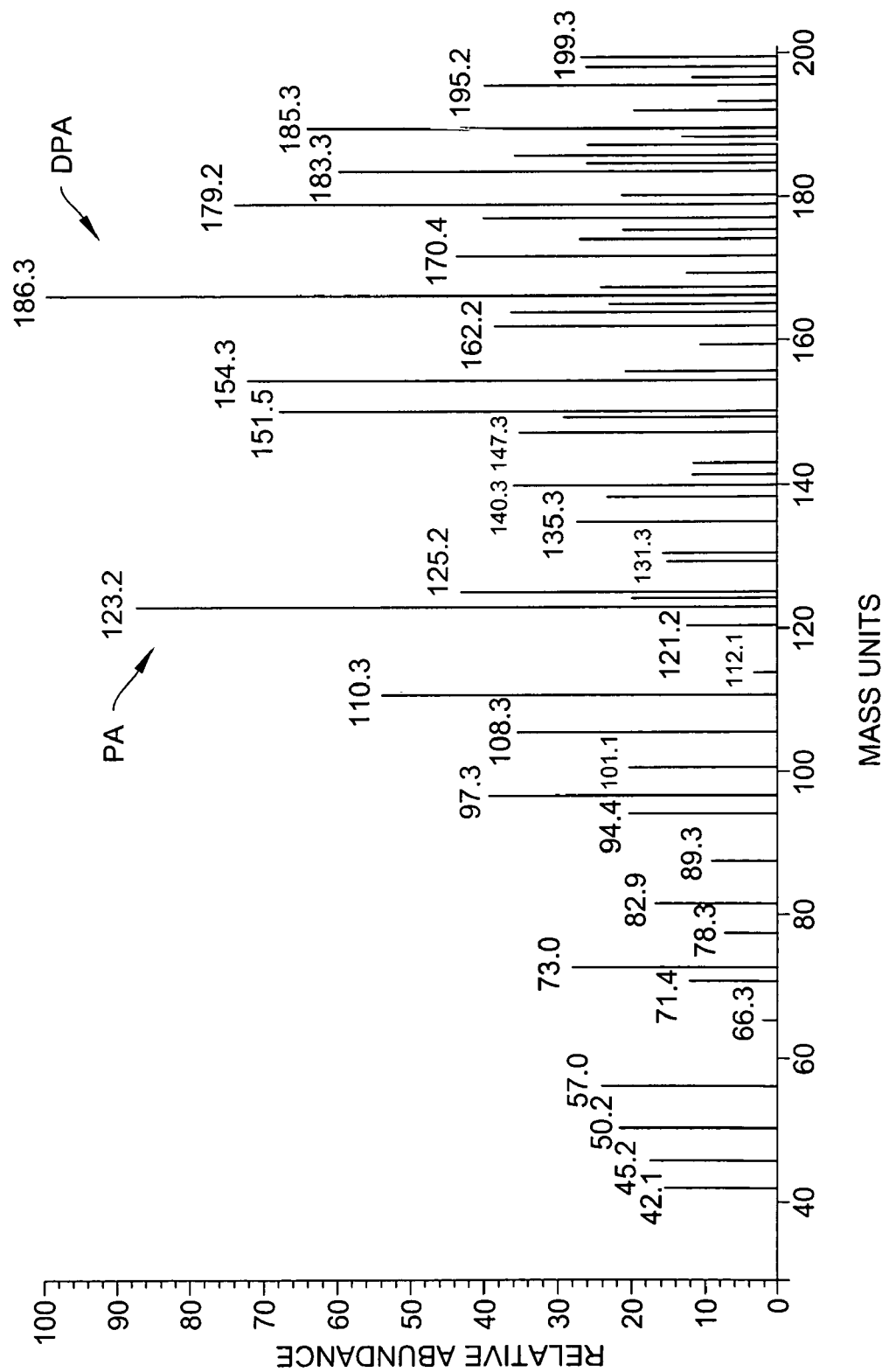
FIG. 7 shows a mass-spectrometric analysis of pyrolysis products of the spores of *B. subtilis*.
Figure 8:
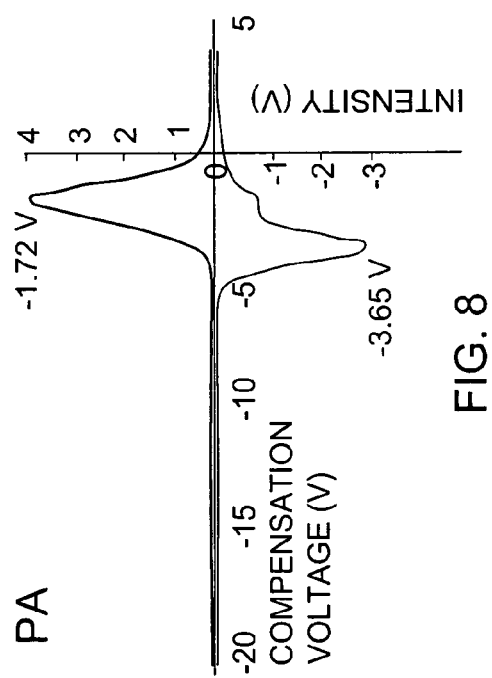
FIG. 8 shows positive and negative ion spectra for picolinic acid in practice of the invention.
Figure 9:
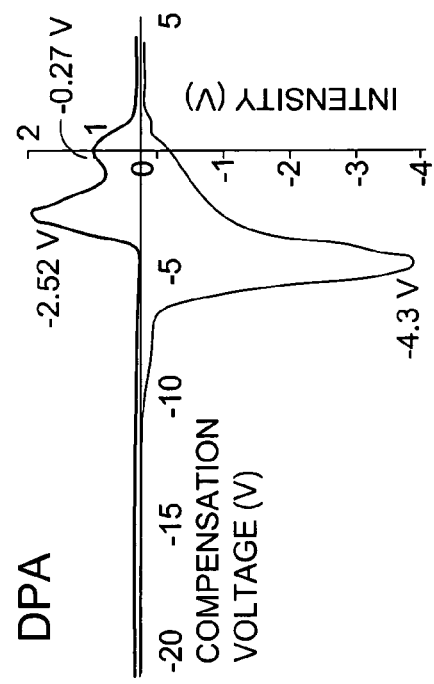
FIG. 9 shows positive and negative ion spectra for dipicolinic in practice of the invention.
Figure 10:
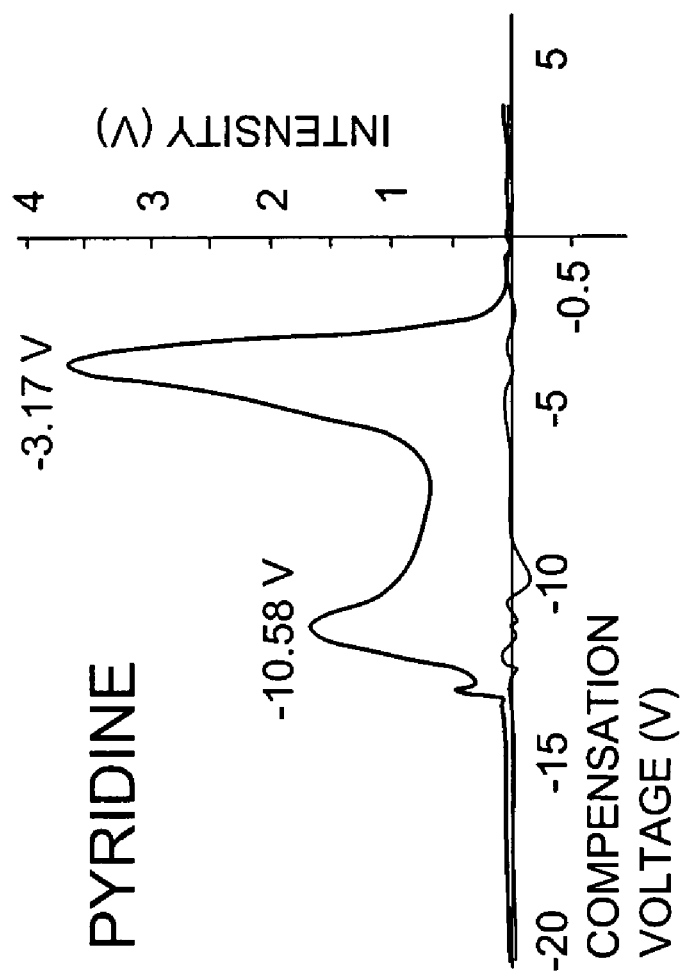
FIG. 10 shows positive and negative ion spectra for pyridine in practice of the invention.

Referring now to FIG. 6, an alternative separation method and apparatus of the invention is shown. In this embodiment, a dual channel system 300 includes a first flow path 11 and a second flow path 311. As the ions are separated by passing through filter 24 in flow path 11, they are deflected by deflector electrode 320 into a detector 326. The deflector electrode 320 is disposed substantially at the output of a flow path (here, a first flow path 11) of a differential mobility spectrometry (DMS) device. Preferably the detector may include a detector electrode 327 which also can be biased to act as an attractor electrode 327 in combination with the deflector 320. In a non-limiting example of the operation of this embodiment, positive ions ($T^+$) will be deflected by a negatively biased deflector 320 and positively biased attractor 327, while a negative ion ($T^-$) will either continue along its original path or will be neutralized on a negatively charged deflector electrode 320. In one embodiment, as the ions strike the detector electrode 327 their charges are registered and generate a detection signal. Now detection spectra can be generated as needed. In the embodiment of FIG. 6, the ions are separated from the rest of the flow out of the filter 24 in flow path 11, and by means of the deflector, a refined set of ion species of interest is detected and/or obtained. As this species is neutralized by contact with the detector electrode they pass out of the detector/collector as a purified set of molecules which may be used as a collected sample, may be re-ionized and reprocessed, or the like.

It will be further appreciated that in embodiments of the invention, detections are made and then the identification process typically involves comparison against a lookup table of stored detection data. Thus a practice of the invention not only results in detection of a marker but also results in indication of the analyte with which the marker is associated. For example, if bacterial spores were in a sample, the above detection results would be obtained and would be compared against a store of related detection data. Upon a positive match, an identification announcement would be made.

Preferably, the apparatus of the invention includes an onboard volatilizer portion and DMS analyzer, wherein collected samples are volatilized and then resulting gas sample is automatically transported to the analyzer and then detected for evaluation of presence of analytes in the sample based on ion mobility signatures. In a further embodiment, the volatilizer and DMS device may be made in a single package. The sample collector may also be on-board.

In a further embodiment of the present invention, a sample is identified by a multi-stage analysis, wherein a first stage filters a sample by particle size and defines a narrowed sample set, and in a second stage this sample is pyrolyzed and then analyzed based on high field ion mobility as discussed. Results of the first and second stage are correlated with known standards to identify the compounds in the sample.

Multichannel (Array) Detection

Devices suitable for practicing the methods of the present invention, are described in U.S. Pat. No. 6,495,823 and U.S. Pat. No. 6,651,224, and include teaching an array of DMS filters. An illustrative device comprises a housing defining at least one flow path between a sample inlet and an outlet, a plurality of ion filters disposed within the housing, each ion filter including a pair spaced filter electrodes, and an electrical controller for applying a bias voltage and an asymmetric periodic voltage across each pair of ion filter electrodes for controlling the path of ions through each filter. In one embodiment, the device provides an array of filters, each filter associated with a different bias voltage, the filter may be used to detect multiple selected ions without sweeping the bias voltage or, in an alternative embodiment, by simultaneously and independently sweeping the bias voltage in different ranges and at different fields. Filters may be in parallel or in series with one chemical sample processing through multiple ion filters.

The teaching of the above-referenced disclosures are incorporated herein by reference in their entirety.

EXEMPLIFICATION

Example 1

Figures 11A, 11B:
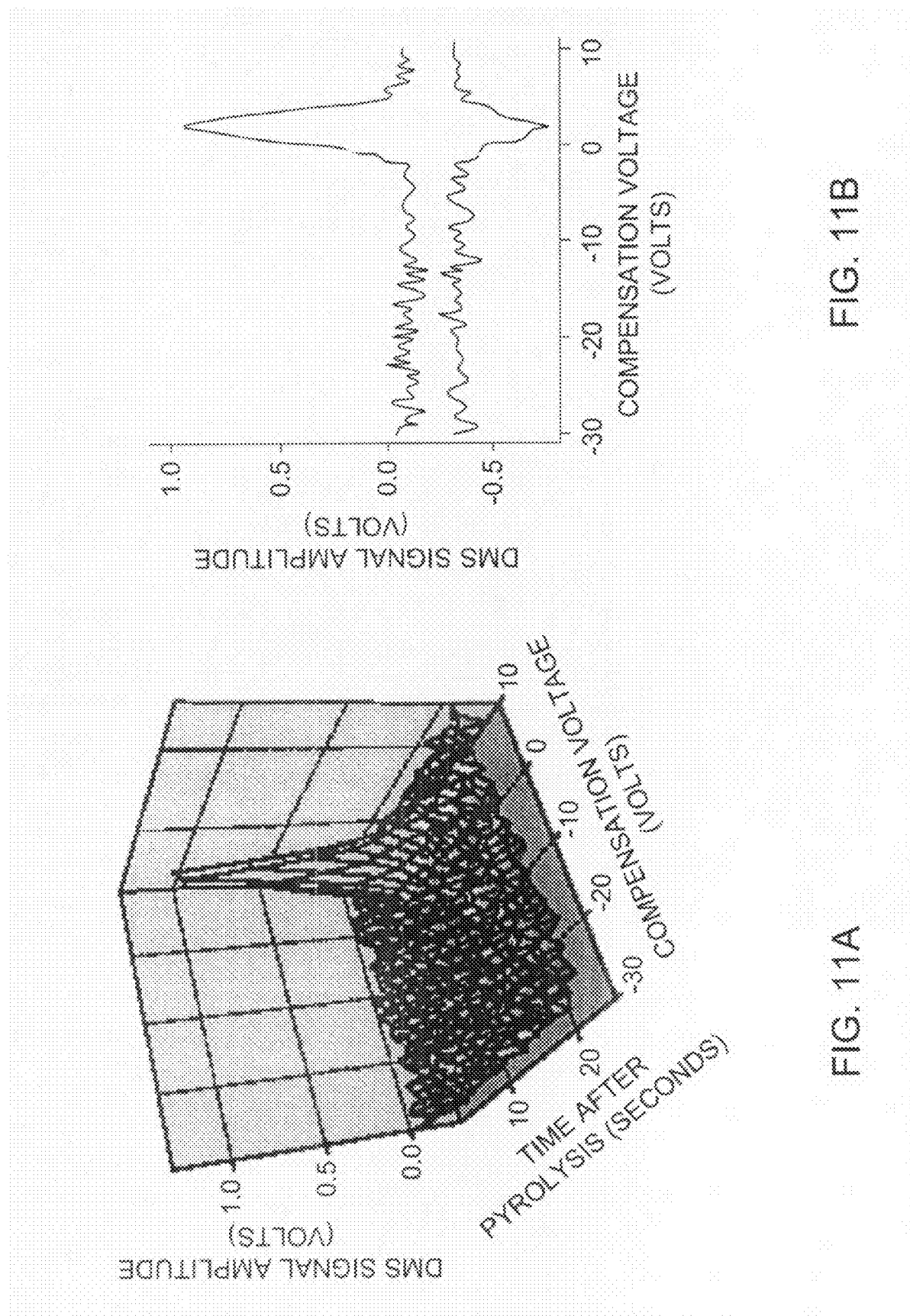
FIG. 11A shows the full time-dependent DMS spectrum of pyrolyzed *B. subtilis* spores as a simulant for *B. anthracis*.
FIG. 11B shows the individual positive and negative ion spectra at 10 seconds after pyrolysis.

Endospore Biomarker 2,6-Pyridine-Dicarboxylic Acid (Dipicolinic Acid) is Detected by a DMS Device and *Bacillus* Spore Biomarkers are Detected by a DMS Device after Pyrolysis Pyrolysis of bacterial spores from species such as *Bacillus* and *Clostridium* produces large quantities of gaseous, 2,6-pyridine-dicarboxylic acid (dipicolinic acid or DPA) as unique marker, which may then be detected by a gas chromatography/DMS device. Typical spores contain roughly 5-15% dry weight of DPA (MW=167), which is speculated to provide the spore with heat resistance. While the presence of DPA does not signify with certainty that an infectious agent is present in the environment, a sudden increase in its concentration can serve as a trigger for initiation of a target-specific search.

The commercially available pyrolyzer PyroProbe 1000 was acquired from CDS Analytical with the necessary functions to handle the introduction of liquid and solid samples into the DMS detector. The pyrolyzer is capable of heating samples from room temperature to 1400° C. at rates from 1 to 20° C./s. The controlled temperature ramping enables selective desorption of compounds from the probe, therefore enhancing resolution and signal-to-noise of the DMS. A drying function evaporates and vents the solvent out a purge vent resulting in sample concentration and prevention of the solvent from entering the DMS filter. A probe cleaning function, flash heats and desorbs left-over sample between analyses. The pyrolate is transferred to the DMS through a sealed and heated interface. During sample loading on the probe, the pyrolysis chamber is purged while a stream of clean $N_2$ is diverted into the DMS. During pyrolysis, the flows are diverted through a 6-port valve into the DMS for introduction of the pyrolate into the DMS.

In order to provide a control result for comparison with data obtained using the DMS unit, a *B. subtilis* sample was analyzed using pyrolysis-ion trap mass spectrometry. The concentration of the *B. subtilis* sample was 10' organisms/ml. This experiment (FIG. 7) showed that the expected biomarkers and both DPA and picolinic acid (PA) were evident in the endospore spectra. Other unidentified biomarkers were also measured using this technique as shown in the background spectral peaks. We further tested the ability of the DMS to detect endospore biomarkers by using both DPA and PA standard solutions.

FIGS. 8 (dual mode), 9 (dual mode) and 10 (single mode) provides spectra for PA and DPA obtained from solid samples pyrolyzed sequentially and detected in a DMS system of the invention. Picolinic acid was pyrolyzed through a temperature excursion of 130 to 300° C. at a rate of 20,000° C./s, the interface temperature was held at 130° C. Dipicolinic acid was pyrolyzed from 145 to 400° C. at 20,000° C./s, the interface temperature was held at 145° C. Both PA (100 ppm) and DPA (100 ppm) produce positive and negative ion peaks that can be used for identification. In addition, pure DPA produces a secondary positive ion peak, further differentiating its fingerprint pattern. The peak width at half height averages 1.4 V. It is known that pyrolysis is capable of fully decarboxylating DPA to pyridine. Ideally, controlled and more gradual pyrolysis conditions will lead to loss of only one carboxylic acid group to group to generate PA, enabling specific identification of the DPA source as bacterial spores. Due to the volatility of pyridine, pyrolysis was not necessary for introduction, and the interface temperature was held at 130° C. As seen in the DMS spectra, pyridine does not produce negative ions. The absence of a negative ion peak enables one to conclude that the pyrolysis conditions employed are mild enough to prevent full decarboxylation and that pyridine can be differentially detected.

FIG. 11A shows the full DMS spectrum of pyrolyzed *B. subtilis* spores as a simulant for *B. anthracis*. The spores were suspended in dH2O at a concentration of 2.4 ×109 spores/ml. The spores were diluted to 100,000 spores in 1 μl, and the sample was dried and pyrolyzed through a temperature excursion from 250° C. to 400° C. at 20,000° C./sec with the interface temperature at 250° C. FIG. 11A shows the time course of the DMS spectra after pyrolysis is initiated. The signal is complex and changes over time, indicating a large number of potential biomarker targets. There is a large prominent peak as well as low amplitude clusters of "noise" in the spectra. The prominent peak may be a complexed form of DPA or PA released during pyrolysis, although exact chemical identification is not possible. The DMS signal may also contain two components in the low amplitude signal: electronic noise, and trace levels of organic volatile compounds. FIG. 11B shows a time course of both the positive and negative DMS spectra at 10 seconds after the onset of pyrolysis. Both spectra show biomarkers are detected. These results show the DMS is capable of detection of known endospore biomarkers.

Example 2

Monitoring Food Quality

Chemical changes in the living system or degradation processes of cells after death are accompanied by the formation of molecular byproducts. These processes include the breaking down of peptides and DNA strands to smaller components, and changes in amino acids that lead to the formation of amines. One of the processes of particular interest is the breakdown of amino acids and the production of diamines and polyamines.

Furthermore it is known that bacterial decarboxylation of ornithine and lysine produces putrescine and cadaverine respectively. An atmospheric pressure ionization method of the invention is particularly suited for the detection of these markers, such as biogenic amines, since they tend to have either high proton affinity and form stable positive ions or high electro-negativity and readily form negative ions that are detected in a DMS system of the invention.

Figure 12:
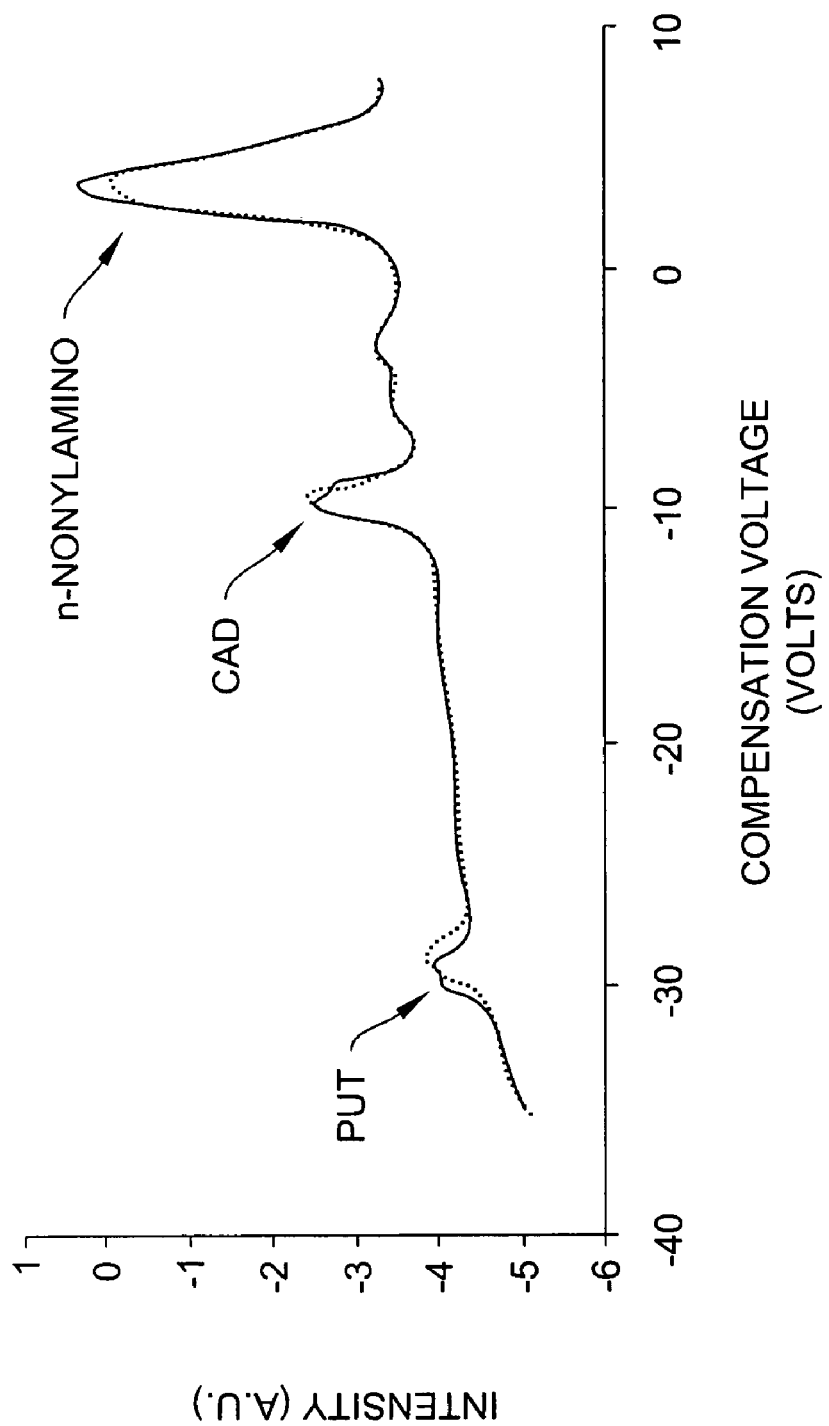
FIG. 12 shows spectra with putrescine and cadaverine resolved from one another in practice of the invention.

FIG. 12 shows DMS spectra detected according to a food-quality embodiment of the invention for a mixture containing both putrescine and cadaverine. The putrescine peak at about −30 volt compensation is well separated from the cadaverine peak at −29 volts, and which are separate from the detected n-Nonylamine. Based on these results, it will be appreciated that a food-quality detector of the invention can be used to evaluate the quality of a food sample, such as meat, based on the detected presence and intensity of these bio-markers.

Example 3

Breath Analysis

Another application of the invention is in breath analysis. The human breath contains over 400 organic compounds at concentrations typically in the parts-per-million (ppm) to parts-per-billion (ppb) range. Only a slender barrier, the pulmonary alveolar membrane, separates the air in the alveoli of the lung from the blood flowing in the capillaries. This membrane allows volatile organic compounds to easily diffuse from the blood into the breath. Moreover, the concentration of these compounds in the breath can be correlated to their concentration in the blood, as noted through the widespread use and acceptance of a breath analyzer to determine alcohol consumption.

Through systematic studies, concentrations of particular compounds have been correlated with specific diseases or impairments in metabolic pathways. However, while these studies are encouraging, there are still a number of complicating factors which have limited wide spread adoption of breath analysis for medical diagnosis. These include: the complexity of current breath analysis systems, their high cost, amount of correlation between the data and disease, and the complexity of data analysis due to interferences and moisture.

In practice of the present invention, a non-invasive DMS breath analysis system is provided. In one set of experiments, sample collection involved collecting a breath sample directly onto a solid phase micro-extraction (SPME) fiber assembly. The SPME fiber was placed in proximity to the mouth of the subject and the sample collected for two minutes. The SPME assembly was coupled to a GC injector port which was held at 120 C and desorbed the sample from the fiber into the GC column. The present wide-spectrum DMS was attached at the detector port of the GC for DMS filtering and species identification of the GC elute.

Figure 14:
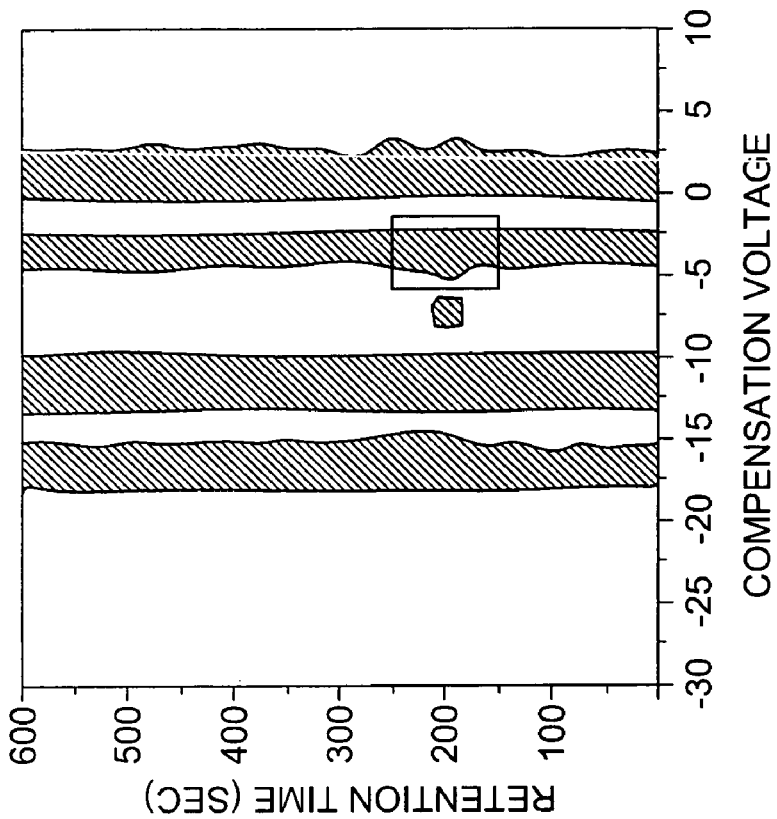
FIG. 14 shows spectra obtained from subject #1.
Figure 13:
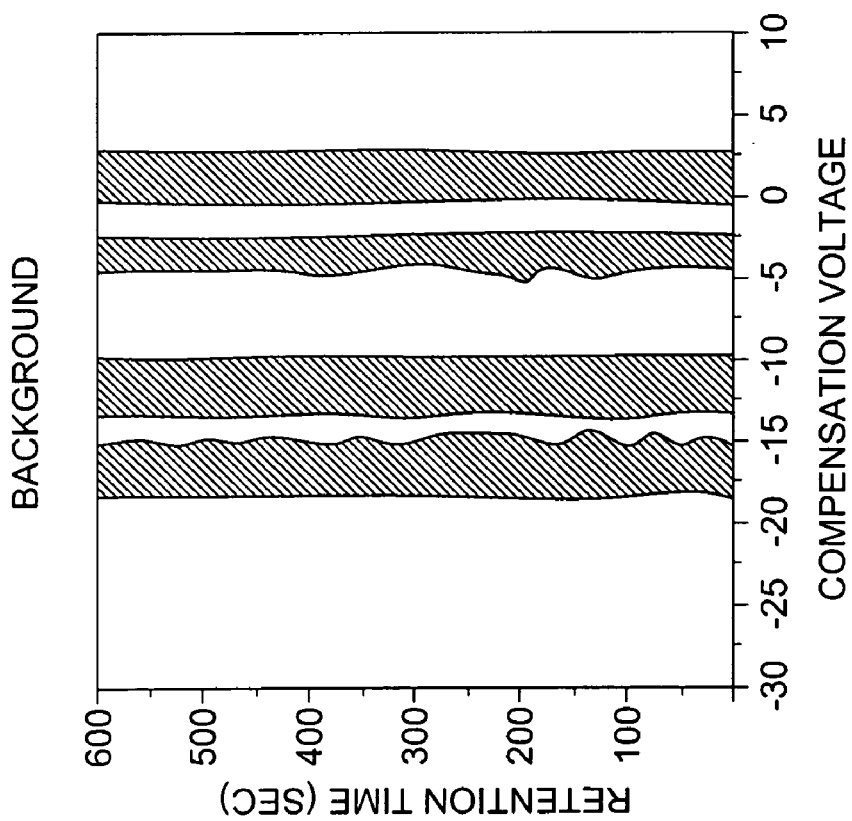
FIG. 13 shows background spectra with no sample present on a SPME fiber.
Figure 15:
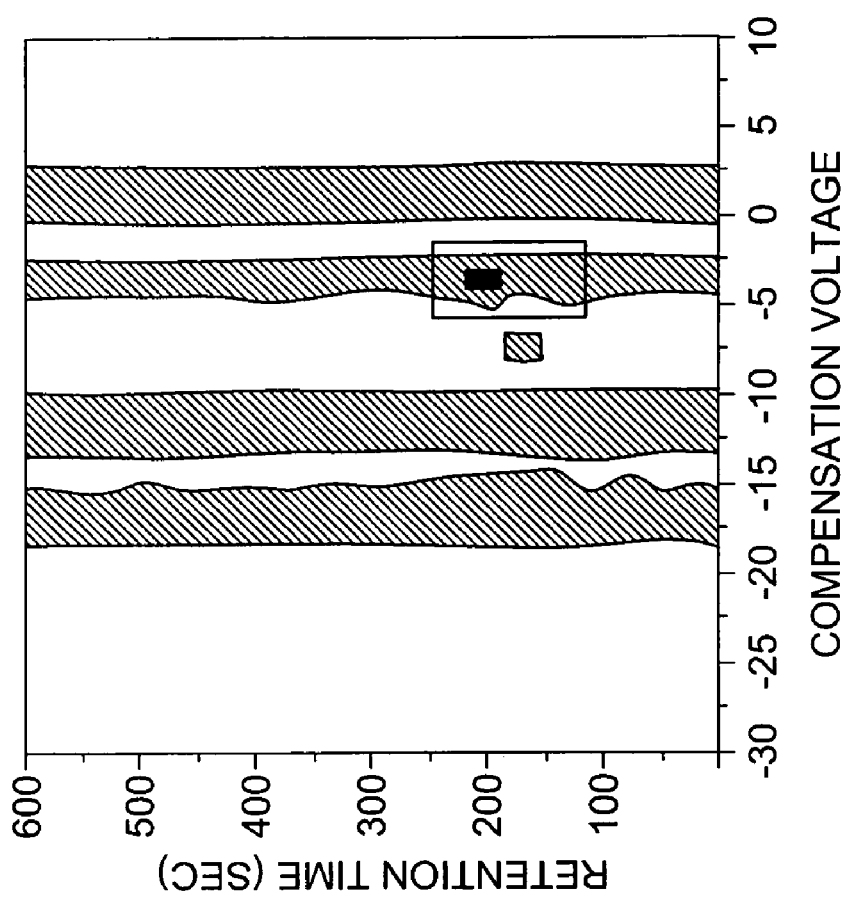
FIG. 15 shows spectra obtained from subject #2.

A background baseline spectra without sample on the SPME fiber is shown in FIG. 13. Spectra from subject #1, FIG. 14, and subject #2, FIG. 15, are very similar except for the peak at a compensation of about −3 volts for specimen #2. Using the GC alone, without the benefit of the present invention, the presence of these different compounds would not be evident. The resultant GC-DMS plots shows the chromatographic retention time on the y-axis and the compensation voltage plotted on the x-axis and shows the value of the detector in providing additional information to simplify and assist in the analysis of a human breath sample, as a viable practice of the present invention. However it also should be noted that in practices of the invention direct sampling and analysis by DMS can be practiced without SPME.

Example 4

B. subtilis Spores Detection

Figure 16:
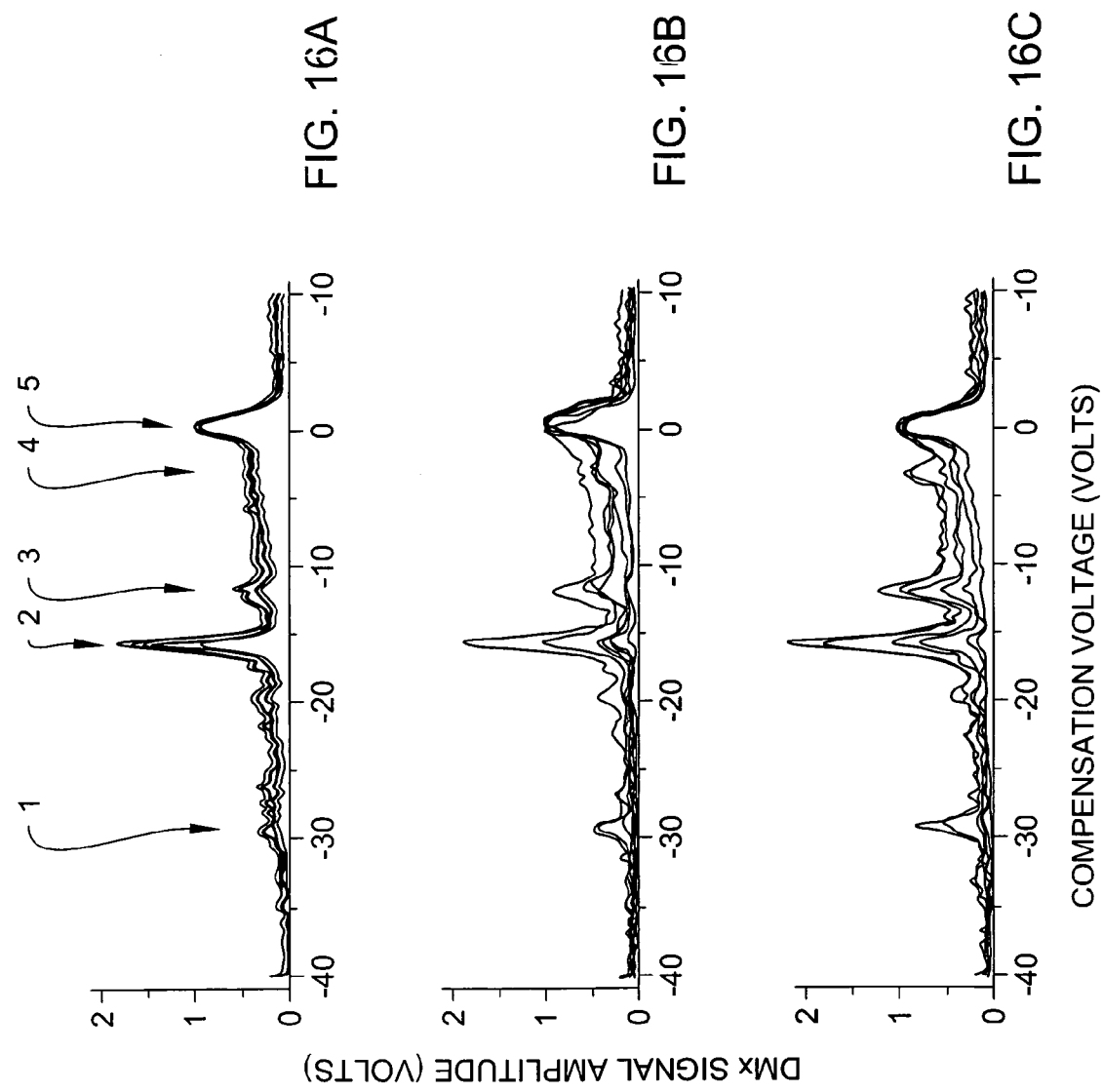
FIGS. 16A-C show spectra generated for markers for *bacillus* spore pyrolysis in practice of the invention.

As shown in FIGS. 16A-C, spectra for markers from pyrolyzed B. subtilis were identified. Spectral DMS scans for pyrolyzed water sample are shown in A, 40,000 spores pyrolyzed are shown in B, and 120,000 spores pyrolyzed are shown in C. A person skilled in the art will recognize from this data that markers at 1, 3 and 4 correlate with the presence of spores, with amplitude corresponding to concentration.

Example 5

Analysis of Murine Urine Samples

Figure 17:
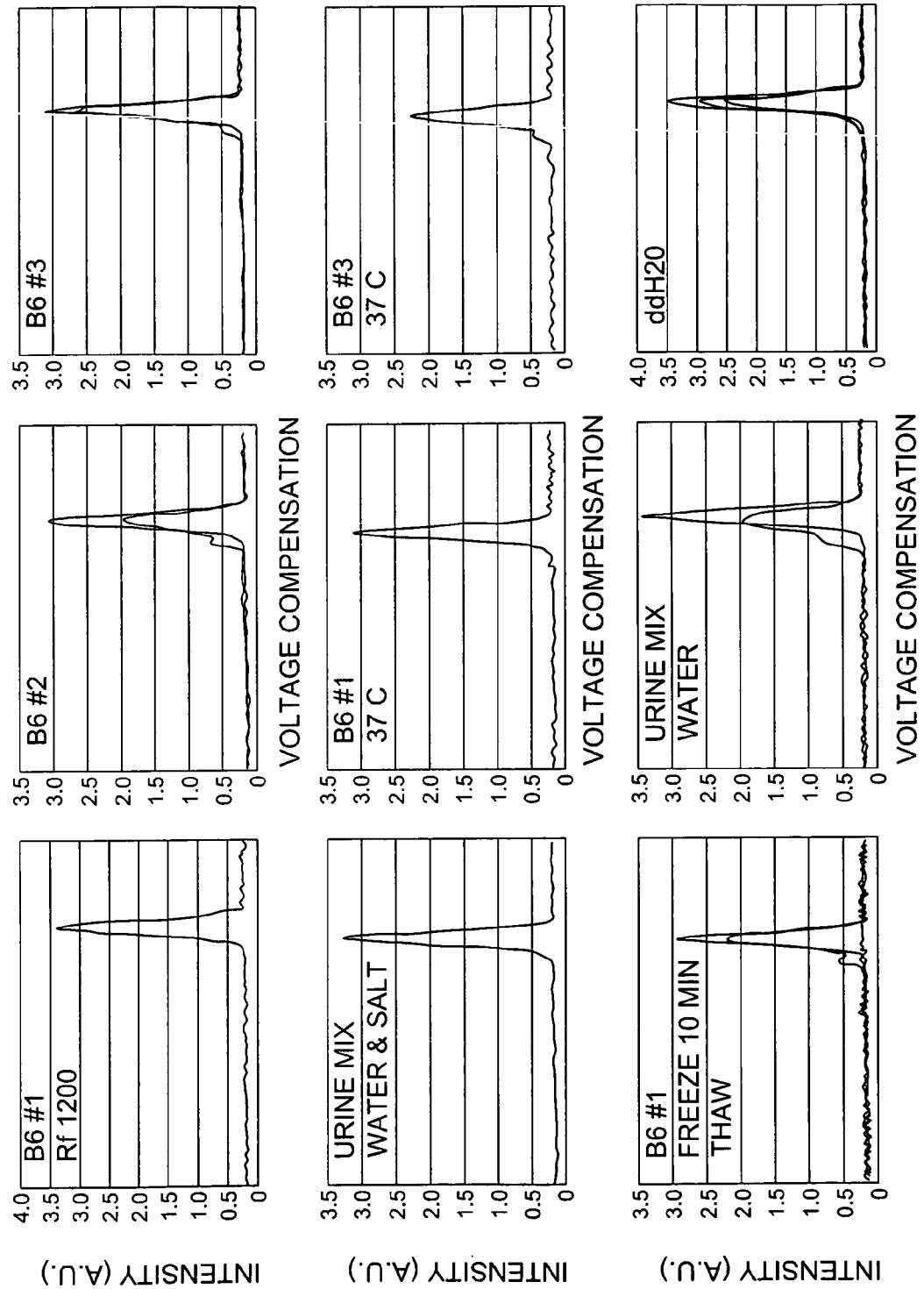
FIG. 17 shows positive ion spectra for urine headspace detected in practice of the invention.

In one experiment mouse urine samples were tested using DMS as shown in FIG. 17 showing positive DMS spectra. In the figure, a large carrier gas (N2) peak (~3 a.u.) is seen at 0 Voltage Compensation (Vc), while urine headspace (vapor) detection spectra is seen just to the left (<0 Vc).

In this demonstration, urine sample headspace vapor from three different individual B6-H-2b male mice was analyzed. The DMS spectra indicated the urine samples were similar to each other but different from two control monomolecular odorants (isovaleric acid and isoamylacetate). A small number of sample preparation permutations were tested to identify conditions that yielded the most volatiles as indicated by intensity in the DMS spectra. Addition of: (1) water (to increase volume of urine sample), (2) salt (0.2 mg/μl), and (3) heat (37 C), all yielded more volatiles.

It was possible to demonstrate use of DMS as a biological evaluation tool for medical diagnostics, such as for urinalysis. It is also noted that such testing does not require fresh liquid samples. While freezing and thawing of such samples reduces the amount of volatiles, still detection can proceed. In practice of the invention, a data base of urine and analyte samples can be determined and stored.

Further, a lookup function of a device of the present invention enables identification of ion species detected in urine. This experiment is illustrative of establishing baseline upon which a specific detector can be established. For example, detection of such analytes as pronase, $(NH_4)_2SO_4$, $KH_2PO_4$—$H_2O$, CK2O3, $K_2CO_3$ or NaCl can be detected.

Example 6

Use of a DMS Device of the Present Invention as a Chromatographic Detector

A DMS device suitable for practice of the present invention was interfaced to a GC and used as a chromatographic detector. The system performance was compared with the Flame Ionization Detector (FID). The average FID detection limit was 2E-10 g, while a preferred DMS system of the invention had a detection limit of 2E-11 g. Furthermore, the DMS is flame-free.

Figure 18:
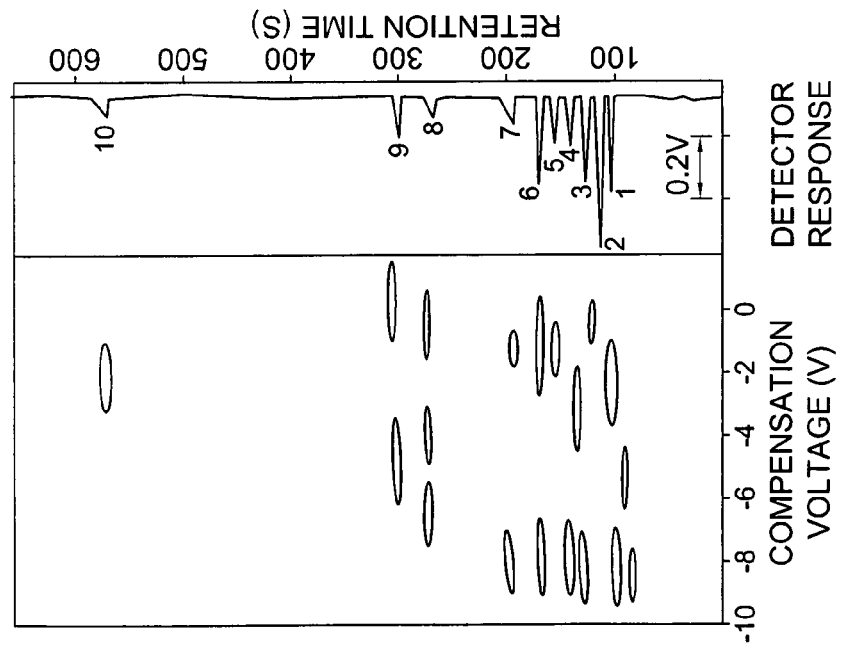
FIG. 18 shows spectra for a DMS embodiment of the invention with a GC front-end.

Similarly to a mass spectrometer, the ion information provided by the invention offers a second dimension of information to a GC chromatogram and the ability to enhance compound identification. FIG. 18 shows spectra according to a GC-DMS embodiment of the invention, with the part shown as a chromatogram (right frame) being typical of what is seen from a FID. In practice of the invention, the chromatogram is the sum of the peak intensities for the product ions created. The associated two-dimensional plot (left frame) of ion intensity (indicated by gradient) versus scanned compensation voltage provides a means of fingerprinting the compounds eluted from the GC. Therefore practice of the invention provides three levels of information: retention time, compensation voltage, and ion intensity, all shown on the spectra of FIG. 18. Furthermore, in a preferred in-line DMS system of the invention such as taught in U.S. Pat. No. 6,495,823, spectra may be obtained simultaneously for positive and negative ions, i.e., dual mode, augmenting or eliminating the need of serial analysis under possibly changing instrumental conditions, as required with other equipment.

Figure 19:
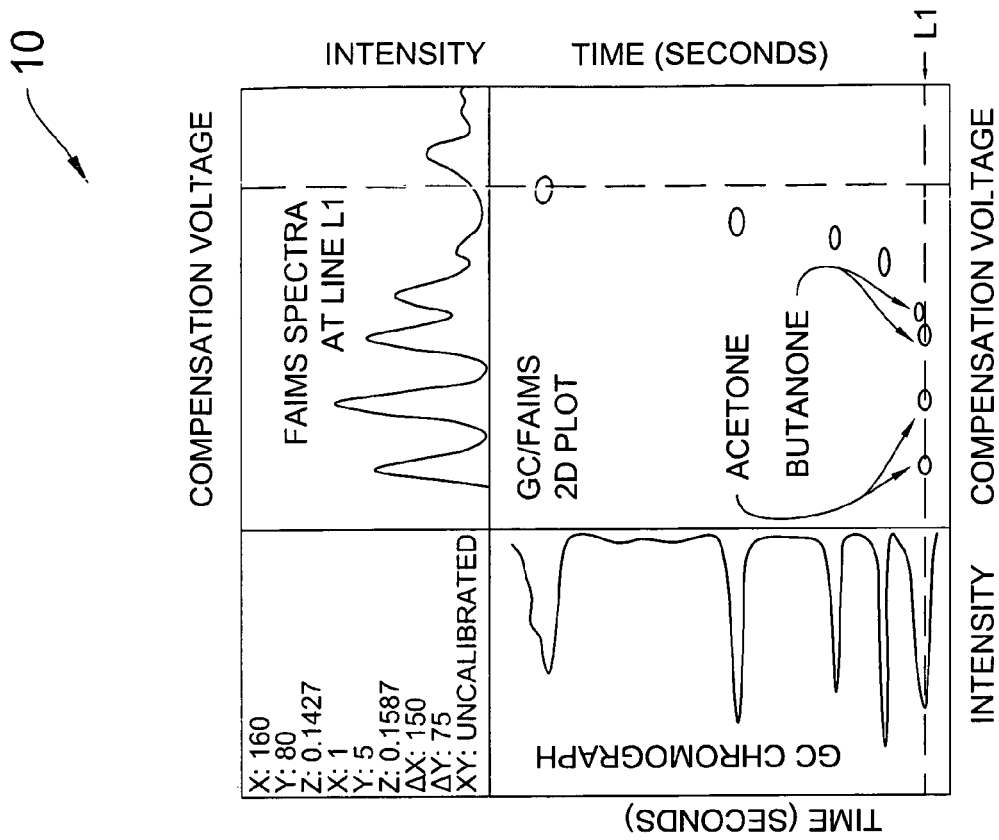
FIG. 19 shows spectra for the GC-DMS where the chromatographic runtime has been decreased leading to co-eluting species and showing that a practice of the invention is able to resolve the co-eluted species.

As shown in FIG. 19, decreased GC runtime produced co-eluting species that were subsequently resolved in the DMS spectra. In this way, a fast GC can be used while maintaining the required compound resolution. Furthermore, the reproducibility of the present invention compares very well to that of the FID as shown in FIG. 20. FIG. 20 shows a comparison of FID and DMS reproducibility for a homologous alcohol mixture.

Example 7

Parallel Analysis of Bacterial Samples Using Pyrolysis/Gas Chromatography and a DMS, Flame Ionization and Mass Spectrometry Detection Devices The py-GC/DMS analysis of bacteria showed a broad range of volatile and semi-volatile organic compounds spanning molecular weights from 50 to over 250 amu. Information contained in the patterns of retention time versus compensation voltage prove analytical value of the differential mobility spectrometer. Products from the pyrolysis of bacteria were matched to known chemicals. The findings were also supported by parallel studies using pyGC/FID and py-GC/MS.

Material and Methods

Detection Devices

Three gas chromatographs (Hewlett-Packard Co., Avondale, Pa.) were equipped with a splitless injector, 15 m SPB-5 capillary column (ID 0.25 mm, 0.25 µm film thickness, Supelco, Bellefonte, Pa.) and different detectors. Each of two HP model 5890A gas chromatographs was equipped with a flame ionization detector or an HP model 5871 mass selective detector (MS). An HP model 5880A was equipped with a DMS analyzer as detector. Experimental parameters for all gas chromatographs were identical and included: initial temperature, 50° C.; initial time, 2 min; program rate, 8° C./min; final temperature, 250° C.; and final time, 5.50 min. Pressure on the injector ports was nominally 5 psig with a split ratio of 50:1 and was adjusted individually so retention times between instruments matched. Split flow was −30 mL/min and septum purge was 3 mL/min. Bottled nitrogen (99.99%) was used as carrier gas for the GC/FID and GC/DMS. Helium (99.99%) was scrubbed over a Hydrox Purifier Model 8301 catalytic reactor (Matheson Gas Products, Montgomeryville, Pa., USA) and used as carrier gas for the GC/MS. Parameters for the FID with integrating recorder were: threshold, 3; area reject, 100; and attenuation, 2. Parameters for the MS were: mass range, 50 to 550 amu; threshold, 500; scan rate, 1.5 scans/s; and electron multiplier voltage, 1600 V according to the automated calibration routine.

The differential mobility spectrometer contained a planar micro-scale drift tube made from ceramic plates with gold plate copper base electrodes. The separating electrodes were 4 mm wide×6 mm long and a width of 0.52 mm was used for the gap between the electrodes. Electrodes were fixed in a metal body to which a −1 mCi $^{63}$Ni ion source was attached. The ion source was connected to a transfer line into the GC oven. Air at 0.5 L/min was heated and passed into the transfer line for gas flow through the DMS analyzer. The transfer line and DMS analyzer were maintained at the same temperature. Air was provided using a pure air generator (Mode 737, Addeo Corp, Miami, Fla.) and was further purified through beds of 13× molecular sieve. Moisture in the carrier gas was monitored using a model MIS-2 meter (Panametrics, Inc., Waltham, Mass.) and was 30 ppm or below. The drift tube was operated using in-house built electronics containing an RF waveform generator, a sweeping voltage generator, and an electrometer. The waveform generator was based on a soft-switched, semi-resonant circuit that incorporated a fly-back transformer and allowed variable peak-to-peak amplitudes of the asymmetric waveform from 200 V to 1600 V without altering the waveform shape. The operating frequency of the RF generator was 1.3 MHz. A compensation voltage ramp was synchronized with the data collection system and provided a scan of compensation voltage from −10 V (or −5 V) to +30 V (or 24 V) at a frequency of 1 scan every 3.8 (or 2.8) s. Signals were processed using a model 6024E National Instruments (Austin, Tex.) board; spectra were digitized and stored for every scan using software derived from Labview (National Instruments).

The pyrolysis apparatus was model 150 Pyroprobe (CDS, Inc., Avondale, Pa.) pyrolyzer with a platinum ribbon probe. The probe was housed during analysis in a glass chamber, with a gas flow inlet and needled outlet. Dimensions of the glass chamber were: inner diameter, 7.2 mm; outer diameter, 9.2 mm; and length, 15 cm. The chamber was attached to the pyrolyzer through a ¾" tube union (Swagelock Company, Solon, Ohio) and the needle attached to the end of glass chamber via ¼-1/16" Swagelok reducing unit. The total volume of the chamber exclusive of the probe was 3.6 mL. Nitrogen was provided to the chamber at 44 mL/min during the run, so the gas volume of the chamber was replaced every 5 s. The chamber was wrapped with a resistive wire heater and insulated with glass pack to maintain temperature at 250° C. during transfer of the pyrolysate to the GC injection port.

Bacterial Cultures and Growth Condition

*Escherichia coli* K-12 (strain #25), *Micrococcus luteus* (strain #52) and *Bacillus megaterium* (strain #61) were obtained from the New Mexico State University Culture Collection. The three cultures were grown for 17 hrs in nutrient broth (Difco, Detroit, Mich.) in an orbital shaker (150 RPM) maintained at 30° C. The cultures were harvested by centrifugation (10,000 RPM, 2 min.), re-suspended in sterile water, spun again, and then re-suspended in sterile water. The cells were quantified by sequentially diluting the cells and plating sub-samples onto nutrient agar plates, and counting resultant duplicate samples. Under these growth conditions, 66% of the *B. megaterium* cells had sporulated as measured by staining with Brilliant Green and microscopic examination. The cells were pyrolyzed and analyzed on the day of preparation, or were stored at 4° C. and analyzed within one week. Biomarkers included Lipid A (Calbiochem Novabiochem Co., La Jolla, Calif.); Lipoteichoic Acid (from BIOTREND Chemikalien Germany); and dipicolinic acid (Aldrich Chemical Co, St. Louis, Mo.) and were used as received without further treatment.

Procedures

Several procedures were used throughout the whole of this study and included handling and injection of the sample from the pyroprobe apparatus to the GC, data collection using the GC/DMS, data reduction to spreadsheets, and analysis of the data.

Before each measurement, the pyroprobe containing the Pt ribbon was heated to 800-900° C. or inserted into the flame of a Bunsen burner to remove residues of previous measurements. Sample volumes of approximately 20 mL were applied by micropipette onto the surface of the Pt ribbon and dried at −75° C. in air for 1 to 1.5 minutes. The temperature of the glass chamber of the pyroprobe was 250° C.

A 10 μL of bacterial sample was placed on the pyroprobe ribbon. Directly before the GC analysis, the pyrolysis apparatus with the pyroprobe containing bacteria was purged with nitrogen at a gas flow of ∼44 mL/min for ∼6 s (one replacement volume of the pyrolysis chamber). The nitrogen flow was stopped and the needle of the apparatus was inserted through the septum of the injection port of the gas chromatograph. Nitrogen was again applied to the pyrolysis apparatus and the sample was pyrolyzed at 650° C. for 10 s. The gas chromatographic analysis was started simultaneously with the start of pyrolysis and the DMS analyzer was operated continuously with mobility scans obtained every 2.8 s (cf. above). After 30 s, the pyrolysis gas flow was stopped and the pyroprobe was removed from the injection port. Since the widths of individual GC peaks were 5 to 7.5 s at the baseline during an elution profile, two to three differential mobility spectra were recorded for each peak eluted in the chromatogram.

The positive and negative spectra of each py-GC/DMS run were saved as ASC 11 files (file size 1.3-1.5 MB). These files were imported into Origin 6.1 and plotted into graphs. Quantitative determinations were made using chromatograms through Peakfit 4.0 (Jandel Scientific, San Rafael, Calif.). Plots of ion intensity versus retention time were deconvoluted with these PeakFit parameters: for automatic baseline subtraction, Linear, 2%; peak smoothing, FFT Filtering in levels from 10 to 24%; Auto Place and fit peaks, Linear two point baseline; FFT Filter, 28 to 54.17 smoothing, options, Chromatography; and Gauss area, 1.5% amplifier.

Results

Profiles from Pyrolysis of Bacteria with GC/DMS

Figure 21:
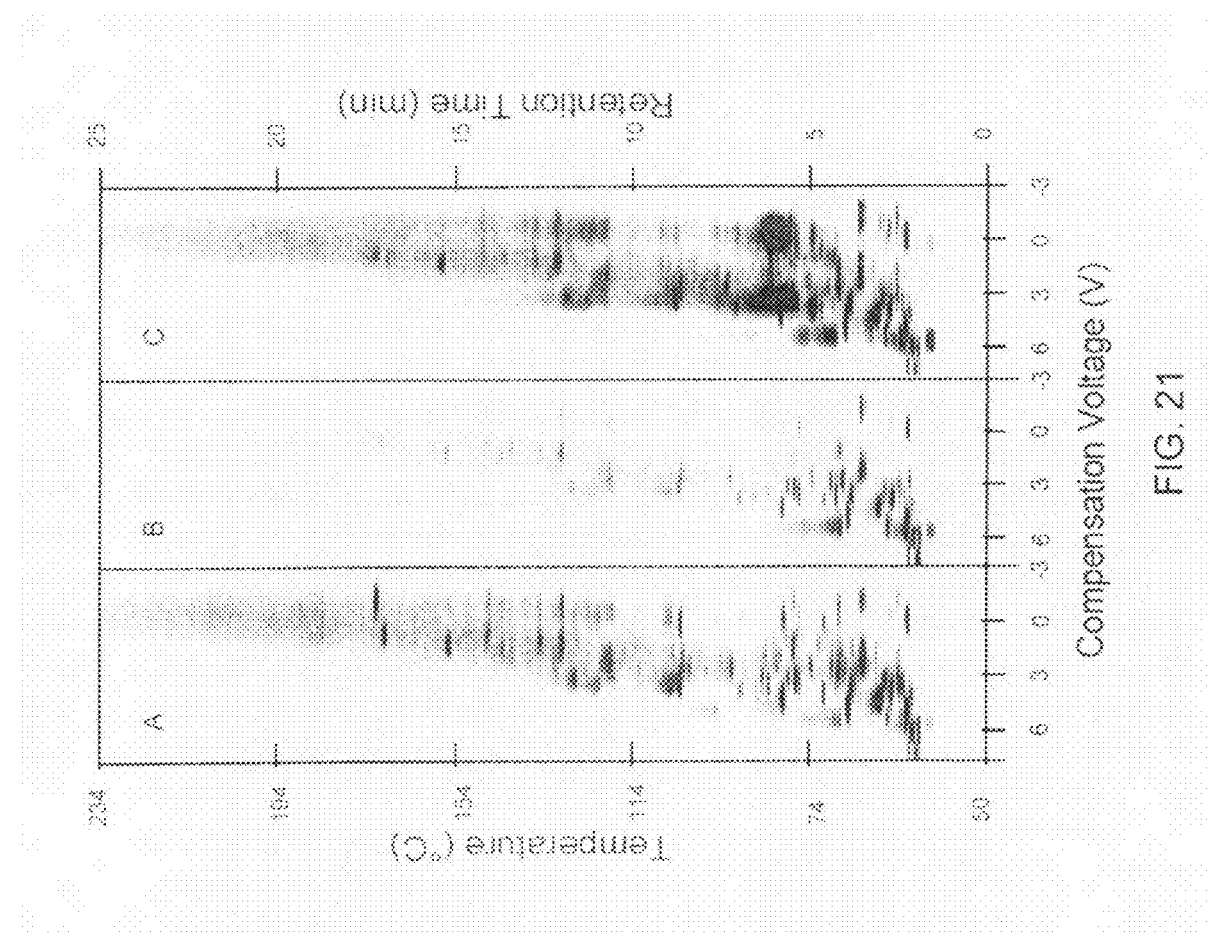
Figure 22:
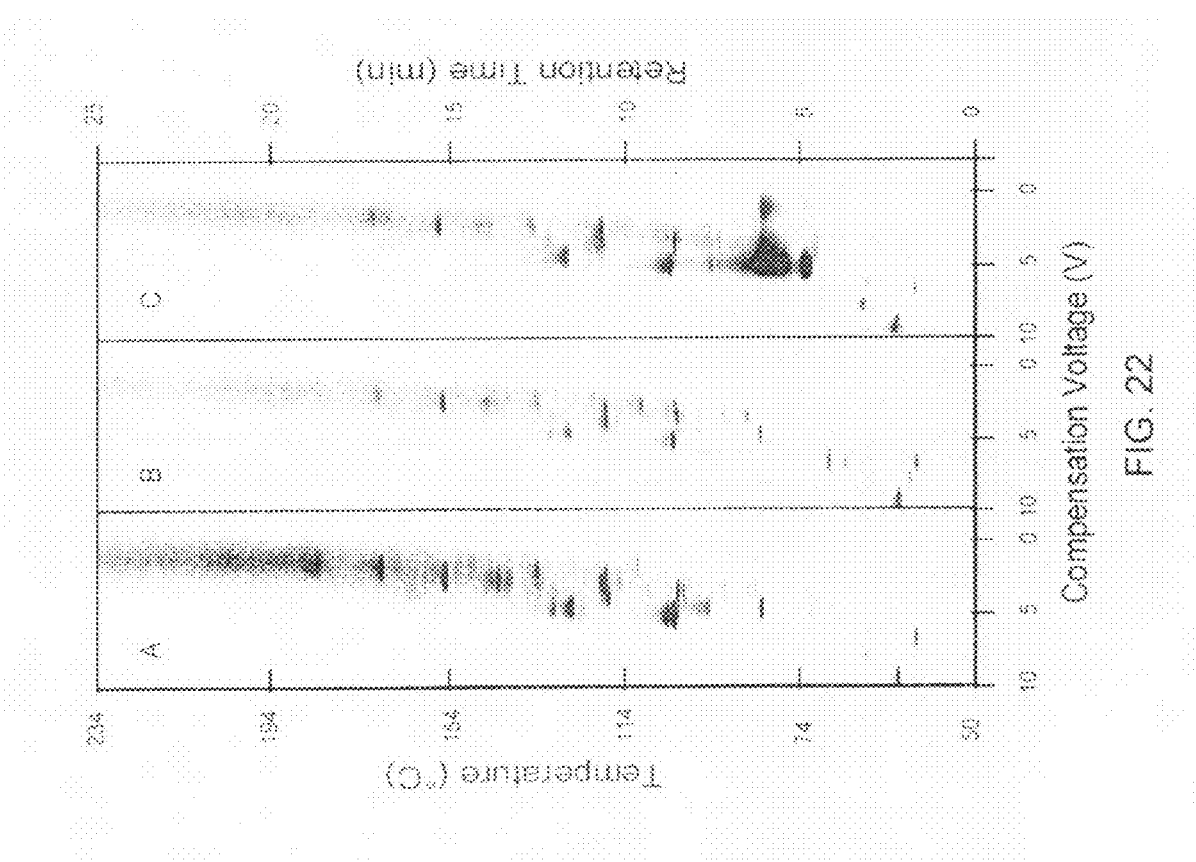

Results from the pyrolysis of three bacteria with GC/DMS analysis are shown as plots of ion intensity, retention time, and compensation voltage in FIG. 21 and FIG. 22. In FIG. 21, plots for positive ions are shown from the pyrolysis of *E. coli*,

*M. luteus*, and *B. megaterium* in frame A, B, and C, respectively. Constituents were seen above background throughout a column temperature range from 50 to −190° C. (retention times of 0 to 20 min) and between compensation voltages of −2 V to 8 V. The peaks in FIG. 21 arise from reactions (Eq. 1) between substances in the GC effluent and a reactant ion ($H^+(H_2O)_n$) seen at a compensation voltage of −14 V (not shown).

$$M + H^+(H_2O)_n \longrightarrow MH + (H_2O)_n^- + H_2O \quad (1)$$
Molecule    Reactant ions           Production In the differential mobility spectra, the more offset peaks (such as at higher values of compensation voltage) will be of lower molecular weight than those at 0 V and are consistent with molecular masses of −50 to −120 amu. Peaks with compensation voltages of 0 to −3 V are found with ions off high mass which exhibit negative dependence of mobility on electric field strength (approximately 150 amu and higher). Thus, the compensation voltage axis can be viewed as a measure of low (at 8 V) to high (at −3 V) mass spanning a range from approximately −50 to 250 amu.

Each bacterium produced a pyrolysate with a complex mixture of volatile compounds and this was observed in results from the GC/DMS, GC/FID and GC/MS. In FIG. 21, a general trend can be seen in the plots for increases in molecular weight with increases in retention time. However, some differential mobility spectra can be seen with two peaks at differing compensation voltages. Commonly in IMS, a protonated monomer will form a cluster with a sample neutral to form a proton bound dimer, $M2H+(H2O)_n$, when sample vapor concentration is increased. The proton-bound dimer will appear at the same retention time as the protonated monomer though compensation voltage will be displaced in the direction of zero that for the protonated monomer. This can be an additional component in the orthogonal differential mobility spectrum as a measure of concentration or abundance. An example of this is evident in FIG. 21C with a component at a retention time of 6 min. where two peaks are seen at 3.4 V and −1 V in the differential mobility spectrum. These peaks arose from the same substance, crotonic acid, and were the protonated monomer and proton bound dimer. In the corresponding GC/MS data set, a single chromatographic peak was observed with the mass spectrum of crotonic acid orthogonal to retention time. This can be seen through the plots for other substances. The complexity of the plots from py-GC/DMS is consistent with findings with py-GC/FID and py-GC/MS analyses made using the same samples under identical conditions of pyrolysis. The chromatograms could be matched among all three instruments within each of the three bacteria samples. The number of constituents, resolved and detected, was 50 to 70 using py-GC/FID, py-GC/DMS or py-GC/MS for the total ion chromatograms.

The reproducibility of the py-GC/DMS plots was determined for compensation voltage, peak intensity and retention time and average values for these were ±0.2 V, 10% relative standard deviation (RSD), and ±0.05 min, respectively. The GC/DMS alone with chemical standards injected by syringe yielded reproducibility of ±0.1 V, 10% relative standard deviation (RSD), and ±0.02 min for compensation voltage, peak intensity and retention time, respectively. This demonstrated that the contribution to variance from sample handling by pyrolysis was negligible when compared to the same for a syringe injection, noted above. Moreover, comparable quantitative variance was obtained from py-GC/FID analyses suggesting that the DMS as detector was not introducing significant variance into the analyses versus the FID. Consequently, any differences seen in the patterns of FIG. 21 are not variability of the DMS but can be associated with chemical differences of the bacteria as discussed below.

In a micro-fabricated DMS analyzer, vapors ionized in the source region are swept into the analyzer region where positive and negative ions are pushed through the drift tube and characterized simultaneously. Results for negative ions are shown in FIG. 22 and came from the same data set shown in FIG. 21. The chemistry of ionization is based upon reactions between substances in the GC effluent and negative reactant ions, here, O2 (H20)$_n$. which was evident at 11.3 V (off scale in FIG. 22), (see Eq. (2)).

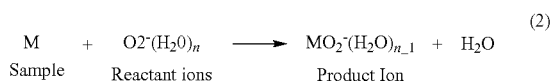

$$M + O2^-(H_2O)_n \longrightarrow MO_2^-(H_2O)_{n\_1} + H_2O \quad (2)$$
Sample     Reactant ions     Product Ion Ionization chemistry with negative ions is generally more selective than that for positive ions and based upon O2$^-$ (H$_2$0)$_n$ attachment to a neutral. This occurs with molecules containing acidic protons or electronegative groups. In some instances, the product or adduct ion (MO$_2^-$(H$_2$0)$_{n-1}$) may dissociate to form M$^-$ or M–H$^-$. The plots of retention time versus compensation voltage for negative ions also showed a large number of constituents between 0 to 20 min elution times and compensation voltages from 10 to 0 V. However, fewer constituents were observed for negative ions versus that for positive ions with from 31 to 39 peaks detected and resolved. This is consistent with the anticipated increase in selectivity for negative ionization chemistry. Crotonic acid was noticeable in the negative ion py-GC/DMS plots and was expected since carboxylic acids exhibit favorable ionization chemistry with O$_2^-$(H$_2$0)$_n$.

The availability of information for negative product ions is an additional and separate measure of chemical identity over positive ion response and is available conveniently with a py-GC/DMS measurement. Such chemical information might be correlated to the response with positive ion chemistry. Alternatively, the capability for response with negative ions is an opportunity to employ derivatizing agents that are particularly well suited for negative ions (fluoro or halo derivatizing agents that have been used with ECDs).

The results in FIG. 21 and FIG. 22 were compared favorably to results by py-GC/FID and py-GC/MS with the same sample. The results in FIG. 21 and FIG. 22 demonstrate that a DMS analyzer shows response with detail for molecules spanning a range of molecular weights from 50 to 250 amu (gauged from retention time or temperature) and that the existing DMS analyzer provided resolution of chemical information orthogonal to retention.

Py-GC/DMS Analyses of Biopolymers

Figure 23:
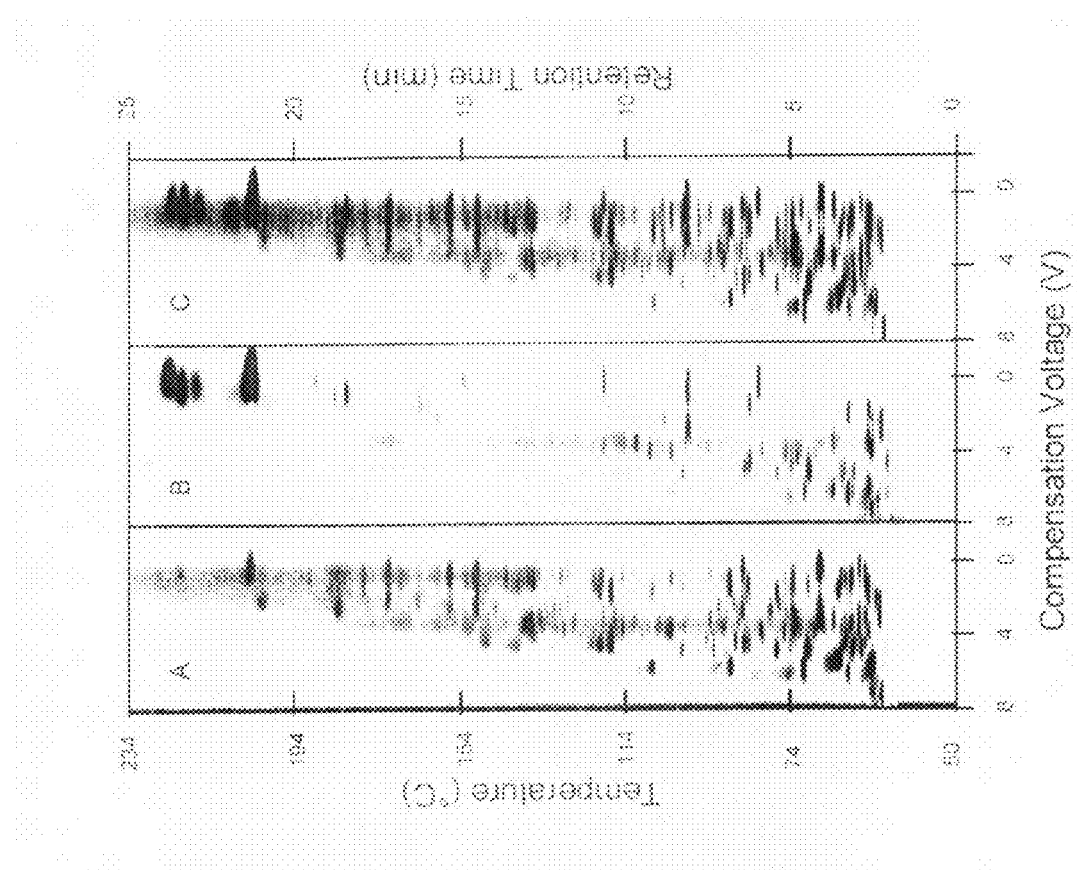

Biopolymers for some major constituents in bacteria are available as purified substances though the choice of materials is limited by genus and species. Lipid A and lipoteichoic acid were obtained commercially and were characterized by py-GC/DMS in order to compare these prospective sources of bacterial chemical information to actual results from bacteria samples. Studies were made of the biopolymers alone and of biopolymers as mixtures with bacteria. Negative controls were made by mixing biopolymers with bacteria missing the biopolymer. Results from these studies are shown in part in FIG. 23A to C from py-GC/DMS determinations of the Gram-negative bacterium *E. coli*, Lipid A, and a mixture of *E. coli* with Lipid A, respectively. The findings show that some of the peaks from *E. coli* can be matched to peaks from Lipid A using retention time and compensation voltage. However, peaks can be seen in the plot for *E. coli* which are not associated with and in plots from analysis of Lipid A and peaks can be seen from Lipid A that are not evident in *E. coli*. The positive control with a mixture showed that differences were not due to matrix effects of any chromatographic uncertainties such as adsorption at active sites. Rather, the profiles were additive as shown in FIG. 23C and the differences cannot be attributed to pyrolysis, GC separation, or ionization chemistry in DMS analysis. These differences are likely due to the origin and composition of Lipid A which came from *Salmonella minnesota* and not from the genus *Escherichia*. Thus, the patterns seen in the plots for *E. coli* may be understood to arise from pyrolysis of biopolymers other than Lipid A. Results from py-GC/DMS analysis of *M. luteus*, lipoteichoic acid, and a mixture of *M. luteus* with lipoteichoic acid showed different patterns from those in FIG. 23, though the virtually identical conclusions as that with Lipid A. In this instance, the lipoteichoic acid was isolated from *Streptococcus pyrogenes*. Consequently, associations between peaks in bacteria with pyrolysis products from biopolymers were unsuccessful. Instead, chemicals known as pyrolysis products from bacteria were obtained as authentic chemical standards and were used to evaluate results from py-GC/DMS and py-GC/MS.

Figure 24:
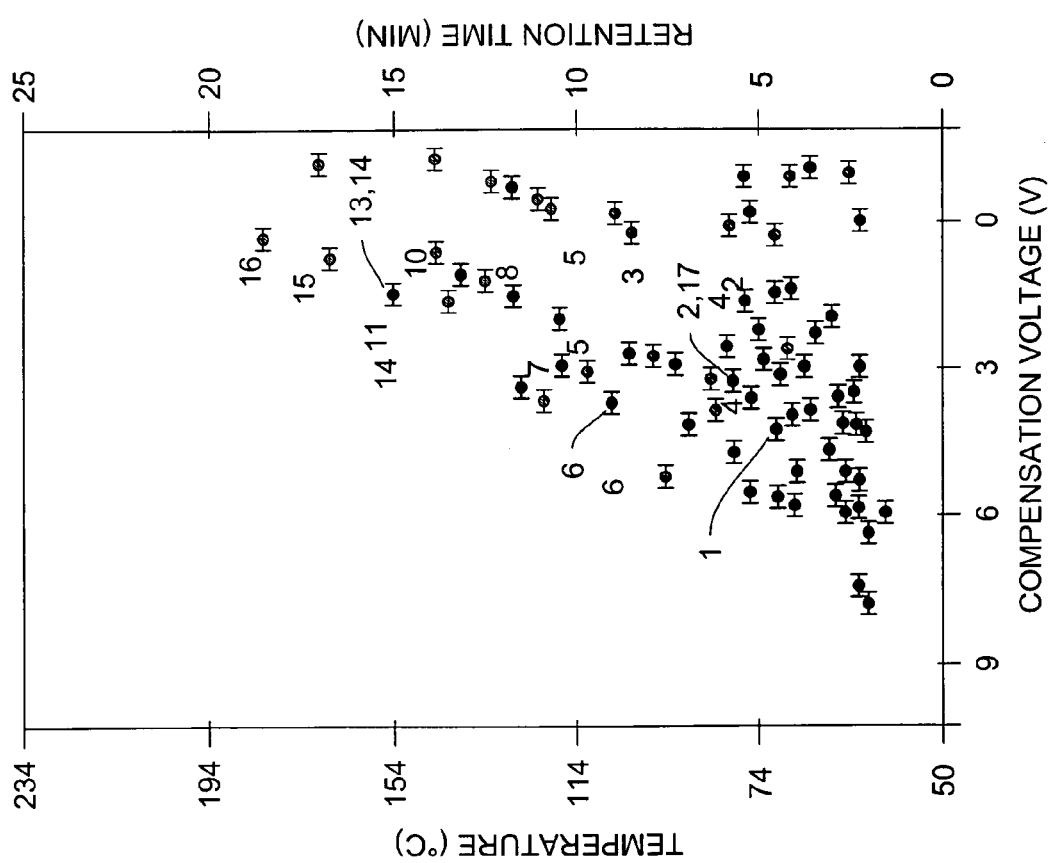
Figure 25:
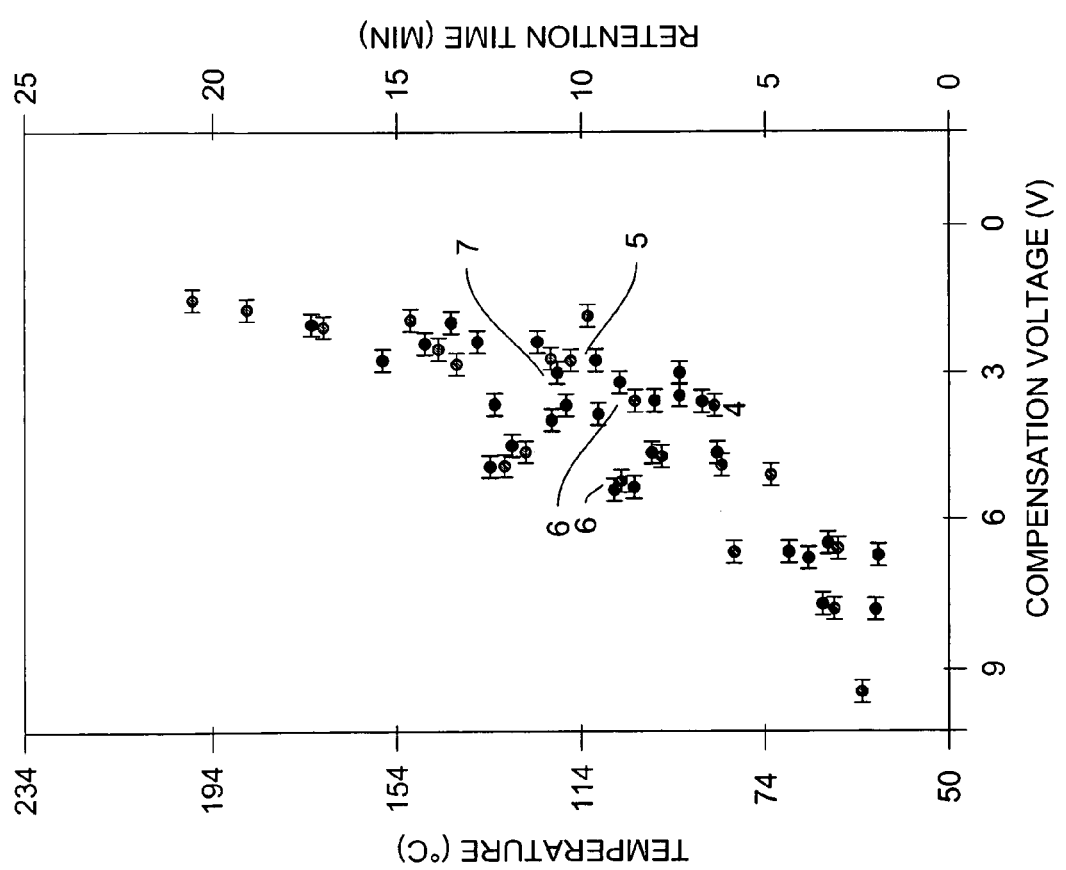

GC/DMS Characterization of Authentic Standards for Chemicals from Pyrolysis of Bacteria Volatile and semi-volatile organic compounds are produced from the pyrolysis of bacteria and these have been recently described by Snyder et al. Samples of most of these chemicals were obtained commercially as authentic standards and were characterized for retention time (t$_r$) and compensation voltage (C$_v$) by GC/DMS, and for retention time and mass spectra by GC/MS. All chemicals except some carboxylic acids exhibited distinct chromatographic retention, distinctive compensation voltages, and mass spectra which matched reference spectra (exceptions included carboxylic acids which, apart from a few exceptions, were either adsorbed on active sites in the injector port or showed poor chromatographic efficiency on the non-polar stationary phase). The location of these chemical standards in plots of retention time versus compensation voltage are shown in FIG. 24 and FIG. 25 with numbers overlaying points for abundant peaks from py-GC/DMS analysis of *E. coli* (70 peaks) and *M. luteus* (50 peaks). Numbers, referenced to the caption in FIG. 24, are placed at the intersection of t$_r$ and C, so comparisons can be made, within the error of measurement, between authentic chemical standard values to values of peaks created from pyrolysis.

Results of both chemical standards and two representatives of Gram-positive and Gram-negative bacteria seen in FIG. 24 where comparisons shows that not all chemicals reported by Snyder could be found in plots for positive ions. However, 8 of 16 chemicals possible were observed as matches in both requirements, i.e., retention time and compensation voltage, and improvement are expected as chromatographic conditions are optimized. This favorable comparison was confirmed and supported by GC/MS analysis which demonstrated that the GC/DMS provided chemical information consistent with the reference method (GC/MS) and consistent with known pyrolysis chemistry described by others. The results also demonstrate that more than 75% of the most abundance chemicals in the py-GC/DMS analyses are unknown. The importance of these other peaks in disclosing chemical information about bacteria is not known and must be established in further studies.

Matches between authentic chemical standards and py-GC/DMS of bacteria (30 peaks for each bacterium) with negative product ions were also evident in a few instances. As seen in FIG. 25, three of the chemicals gave favorable matches with bacterial plots and the remaining peaks were of unknown identity. These three chemicals were also the only authentic standards to give negative ion response. These findings demonstrated that py-GC/DMS analyses provided some chemical information that should be expected from bacteria.

Discrimination Between Bacteria Using Results from py-GC-DMS.

The central question in these studies was the suitability for py-GC/DMS to provide analytical information to allow the discrimination between bacteria as Gram-negative, Gram-positive, and spore forms. A particular interest was if useful information was encoded in peaks of strong intensity and hence ease of comparison. Results with spores were dramatic as seen in FIGS. 21 and 22 where a distinguishing and reproducible peak or substance was formed uniquely with spores. This chemical was identified as crotonic acid using mass spectra, retention time and compensation voltage with an authentic standard. Though crotonic acid has not been used previously as a biomarker for spores and is regarded as a chemical for Gram-positive bacteria in general, crotonic acid was not seen above detectable levels in analyses by py-GC/MS or py-GC/DMS of $M.$ $luteus$. Rather, $B.$ $megaterium$ with high spore content only produced crotonic acid here. In prior studies, spores were distinguished by the presence of picolinic acid and pyridine or methyl derivatives of picolinic acid. Unfortunately, picolinic acid was absorbed on active sites of the injection port when solutions of 10-100 ng/µl were analyzed. Discrimination between Gram-negative and Gram-positive bacteria required detailed attention to plots in FIG. 24 and FIG. 25 and the identification of peaks unique to each bacterium type.

Of the 70 peaks seen in FIG. 24 from $E.$ $coli$, the majority were found in locations of retention time and compensation voltage distinct from $M.$ $luteus$. Which of these peaks might be useful, alone or in combination, as biomarkers for Gram-negative bacteria and which will be too dependent upon cell history to be analytically useful has not been determined. The large number and separation for other peaks is promising. Less promising is the distinctiveness of analytical data for Gram-positive representative, $M.$ $luteus$. Few intense peaks were observed for py-GC/DMS analysis of $M.$ $luteus$ and most of these are coincident with peaks from $E.$ $coli$ as seen in FIG. 24. Only four peaks in the present instrumentation and pyrolysis methods can be distinguished from Grain-negative bacteria and these are seen at retention times of 5, 5.2 and 13.5 min. However, the unpromising condition is substantially altered with chemical information is introduced from negative ions. Plots for negative ions are shown in FIG. 25 and provide another dimension of chemical information ($t_r$, $C_n$ and ion polarity) and in this instance, nearly nine peaks were observed for Gram-positive $M.$ $luteus$ and were thought to be characteristic markers for $M.$ $luteus$. These are seen at retention times (min) of 2, 3.6, 4, 6.5, 9.5, 11, and 12.5. This demonstrates an advantage of DMS over traditional IMS with the simultaneous characterization of positive and negative ions.

Figure 26:
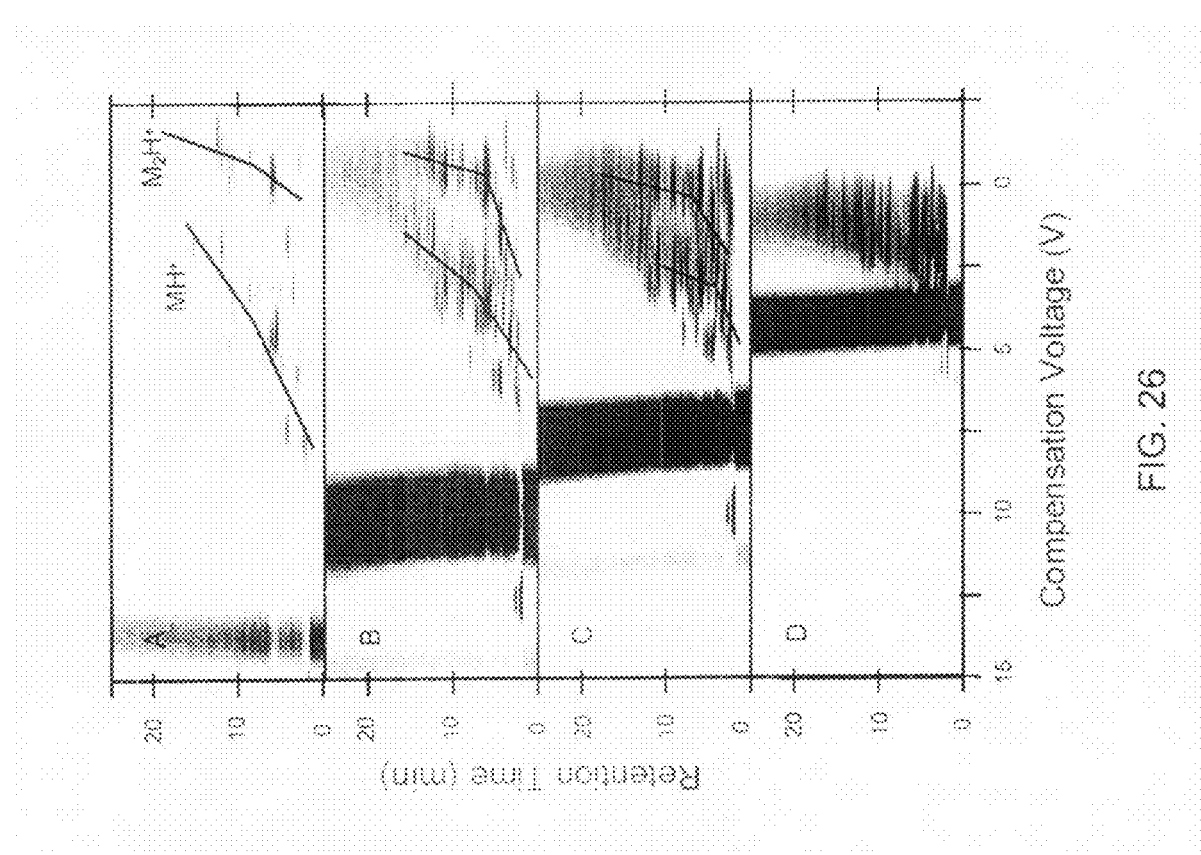

Resolution and Sensitivity with Separation Field and Temperature of the DMS Analyzer In one practice of the invention, the separation voltage was varied to explore effect on resolution between peaks on the compensation voltage axis. Results are shown in FIG. 26 from py-GC/DMS characterization of $B.$ $megaterium$ for positive ions from four settings of the separation voltage (low to high, bottom to top). In FIG. 26D, the reactant ion peak (Equation 1) is evident at compensation voltages from 3 V to 5 V with a center at 4 V. Throughout this analysis, this peak is visible and exhibits a small drift in compensation voltage. This is attributed to a small increase in temperature of the drift tube during the GC column temperature program caused by poor thermal control of the drift tube. At low separation voltage, product ions appear throughout the chromatogram at compensation voltages between 2.5 to 0 V, a small band for distribution of analytical information. As voltage is increased from 688 V to 860 V (FIG. 26C), the reactant ion peak is shifted from −4 V to −7.5 V consistent with a positive alpha function known for hydrated protons. Product ions in positive polarity also show changes in compensation voltage as the separation field is increased and some ions have been shifted to compensation voltages higher than those in FIG. 26A. These are known to occur through changes in AK and are characteristic of ions with masses below 150-200 amu, namely protonated monomers of small molecules as marked in FIG. 26. Other peaks were shifted toward a zero or negative voltage as the separation voltage is increased and such ions have negative dependence of mobility on electric field. In prior studies, these ions exhibited masses larger than 250 amu and have been associated with proton bound dimers. Thus, the presence of two peaks of differing compensation voltage at the same retention time can arise from distribution of charge between protonated monomer and proton bound dimer as governed by vapor concentration as found in conventional mobility spectrometers. The advantage of this is that concentration information is available directed in the differential mobility spectra and the range of separation voltages allows control of resolution within boundaries.

Further increases in separation voltage to 944 V (FIG. 26B) and to 1032 V (FIG. 26A) lead to exaggeration of the patterns seen in FIG. 26D and FIG. 26C. The reactant ion peak is displaced to 14 V and a dramatic decrease in peak intensity was observed. This loss in intensity is observed in general with this DMS design and the cause is not fully described. A similar shift in compensation voltage and loss in peak intensity is also evident with product ions. The shift in compensation voltage means that resolution within the differential mobility spectra increases considerably with each increase in separation voltage; this is expected from plots of mobility dependence with electric field. Nonetheless, a compromise between resolution and peak intensity was found at 944 V and was used throughout all the studies presented above.

Measurements for negative ions paralleled the trends seen with positive ions. Product ions were seen between −4 to 2 V at low separation voltage and resolution of peaks improved on the compensation voltage axis as the separation field was increased. Unlike positive ions, negative ion clusters such as $M_2O_2^-$ are not commonly observed at these vapor levels and the pattern with increased separation voltage was comparatively simple with single ions for each chromatographic peak. Nonetheless, product ions were shifted toward greater AK and larger compensation voltages with increased separation voltage. Loss in peak abundance was observed also with negative ions with greatest loss occurring between 944 and 1032 V, consistent with the product ion behavior.

Figure 27:
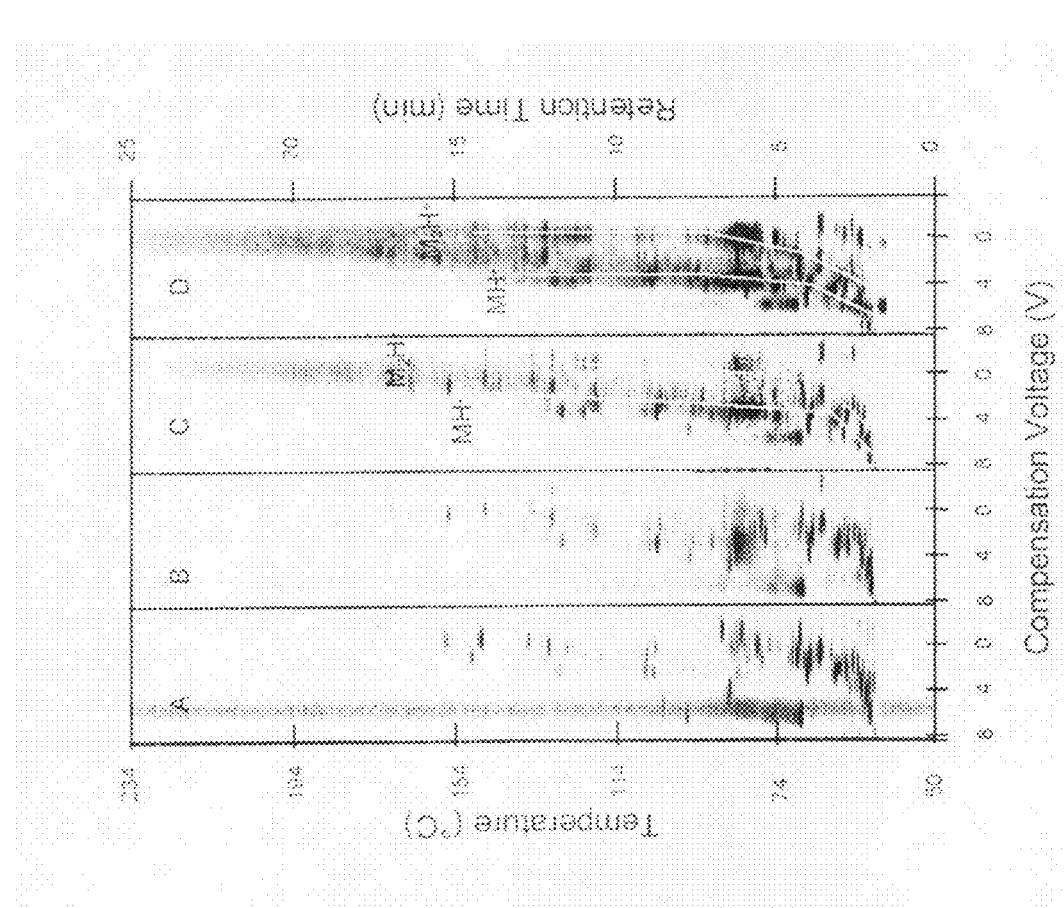

Detectors in gas chromatography are operated generally at temperatures 50° C. or higher above the maximum temperature applied to the column and these guidelines are intended to prevent sample condensation in the detector. However, temperature has secondary effects in IMS analyzers including ion declustering, dissociation, or decomposition. Thus, a concern was the compromise between sample condensation in the detector and distortion of analytical information through changes in ion stability with temperature increases. Results from py-GC/DMS screening of *B. megaterium* with four temperatures of the DMS drift tube are shown in FIG. 27; gas temperature was determined in the flow vented from the drift tube. The pattern of peaks at two or more compensation voltages seen at 55° C. (FIG. 27D) are characteristic of the presence of protonated monomers and proton-bound dimers routinely observed in mobility spectrometers including DMS at low temperatures. An example of this is the pattern at 6 min. where peaks appear at compensation voltages of 3.5 V and 0 V for protonated monomer and proton bound dimer, respectively. However, as temperature is increased in steps, intensity for the peak of the proton bound dimer declines and is missing at 115° C. (FIG. 27A). Though a slight decline in intensity for all peaks was observed with this temperature change, the peaks at compensation voltages of 1 to −1 V, understood to be cluster ions, were lost from the DMS scans uniformly at all retention times.

Though decreases in temperature may be expected to alter the chromatographic pattern through losses of sample by condensation for substances that elute at high column temperatures, there is no apparent loss of chromatographic detail above retention times of 10 min (115° C.) or 15 min (150° C.) when the DMS is low temperature of 55° C. At temperatures up to 110° C., there was no observable increase in number of peaks eluted from the column though apparent sensitivity of the DMS decreased with increased temperature. After some weeks of py-GC/DMS measurements with the DMS at 55° C., decreased intensity in response was observed uniformly for all substances throughout the retention time scale and was attributed to a gradual accumulation of sample as condensate in the drift tube. This diminished response was reversed by heating the drift tube to 110° C. or higher; heating was accompanied by loss of reactant ion peaks which were replaced by a single peak near 0 V. This was understood as excessive vapor levels of the source region produced from off gassing of condensed sample in the source region. After some hours the analyzer was restored in clean response as seen in the differential mobility spectrum.

Comparable trends noted above for *B. megaterium* in resolution, spectral profiles and contamination at various temperatures were obtained also for *E. coli* and *M. luteus*. A temperature for the DMS was a compromise between eventual loss of response at low temperature through accumulation or condensation of impurities and the loss of detail in differential mobility spectra from ion declustering at high temperature. A temperature of −90° C. was chosen in further studies and provided a balance between stable sensitivity over long periods and differential mobility spectra with multiple peaks or bands.

Quantitative Py-GC/DMS of Bacteria

Figure 28:
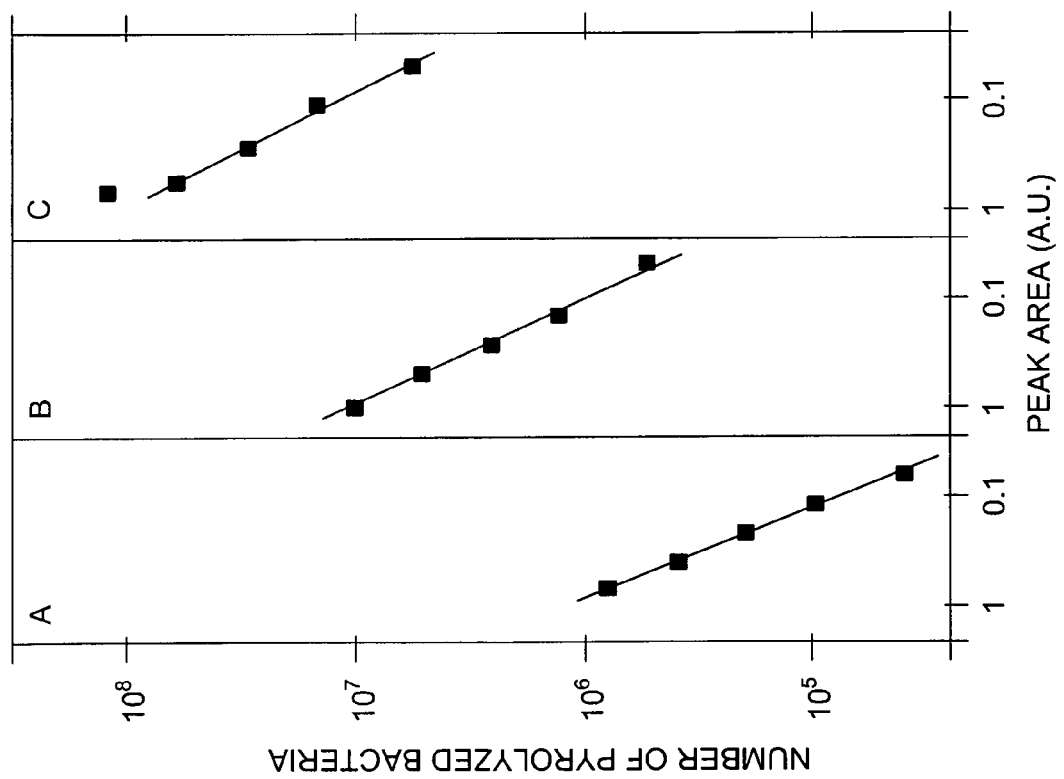

Mobility spectrometers equipped with radioactive ionization sources such as $^{63}$Ni exhibit proportional and quantitative response toward vapor concentrations for peak intensities in mobility spectra though linear ranges may be only 10-100. Differential mobility spectrometers show detection limits from 10-100 pg for volatile organic compounds and linear ranges of 100-1000. Response from py-GC/DMS analysis of bacteria is shown in FIG. 28 for integrated peak area versus number of bacteria applied to the pyrolysis probe. The plots were made using only the area for a single biomarker and the DMS was operated for maximum ion resolution (a large separation voltage). Consequently, the plots in FIG. 28 do not represent optimum conditions of temperature, separation field, or data processing to establish a limit of detection. Rather, these studies were made to establish if a quantitative basis existed between the pyrolysis step and the observed response. The plots suggest that the sum of all parts of the measurement including pyrolysis and DMS analysis are linear in the range explored. No additional efforts were given to processing the data through sum of all product ion intensity. Presumably, additional dynamic range or improved detection limit should be possible if the signal was processed and integrated or if only several biomarkers were integrated and summed.

The minimum number of bacteria seen in this early studies was $10^n$ bacteria where each bacteria showed characteristic response where n for bacteria were 4.6, *B. megaterium;* 5.8, *M. luteus*, and 6.8 *E. coli*. The detection limits will be governed by the DMS through the balance between resolution and ion yield, which are inversely related and controlled primarily by separation field. That is, increased resolution attained through increased separation field results in this generation of DMS with increased ion losses. In limited studies to confirm these expectations, separation fields were decreased and 6000 bacteria were detected for *E. coli* using a single biomarker.

Example 8

Comparison of IMS-TOF to DMS: Resolution of Meta- and Para Xylenes

To illustrate the advantages of the method and apparatus of the invention, compounds that are extremely difficult to resolve in time-of-flight ion mobility spectrometry (TOF-IMS) are shown to be easily resolved in DMS practices of the invention herein. TOF-IMS is a highly sensitive, quantitative method for organic compound detection. It has been used for detection of chemical warfare agents, illicit drugs and explosives, and unlike mass spectrometry, it operates like the present invention at atmospheric pressure, eliminating the need for vacuum tight seals and power consuming vacuum pumps.

However, the TOF-IMS operates with low strength electric fields where the mobility of an ion is essentially constant with electric field strength, while the present invention operates in periodic high fields and filters based on the non-linear mobility dependence of ions on the high strength fields. Thus the invention can provide more and different structural information about ion species that further enables accurate species detection and identification. Further comparison with TOF-IMS is instructive.

It will be understood that mixed xylenes are the second-most-important aromatic product for chemical manufacturing around the world, ranking behind benzene and ahead of toluene. Of the three isomers (ortho-, meta- and para-xylene) p-xylene is the most widely used isomer in the manufacture of polymeric materials. Separation of these isomers is generally challenging with most analytical instruments. Since these isomers have the same molecular weight they cannot be resolved in a mass spectrometer.

Figure 30:
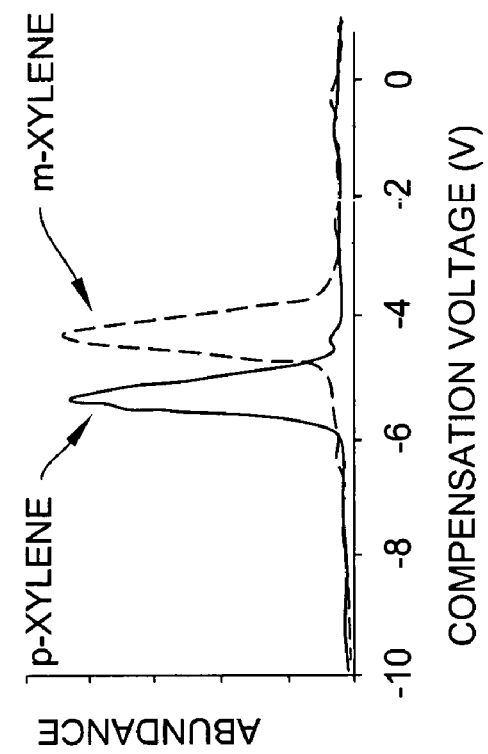
Figure 29:
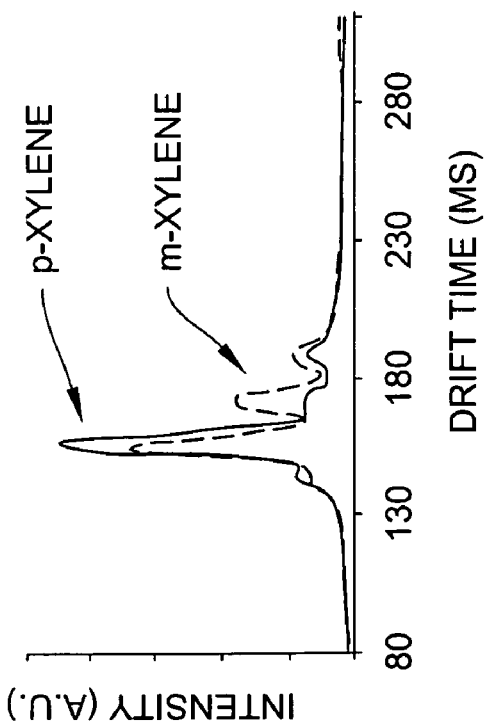

In conventional TOF-IMS these compounds have virtually overlapping peaks, as shown in FIG. 29. While these compounds can be resolved in a gas chromatograph (GC), this typically takes more than 20 minutes. Meanwhile devices in practice of the invention enable excellent resolution of the para and meta xylenes in under one second. FIG. 30 shows these compounds clearly resolved in practice of the invention, notwithstanding such surprisingly rapid performance.

Example 9

High Sensitivity of DMS in Detection of Methyl Salicilate

Figure 31:
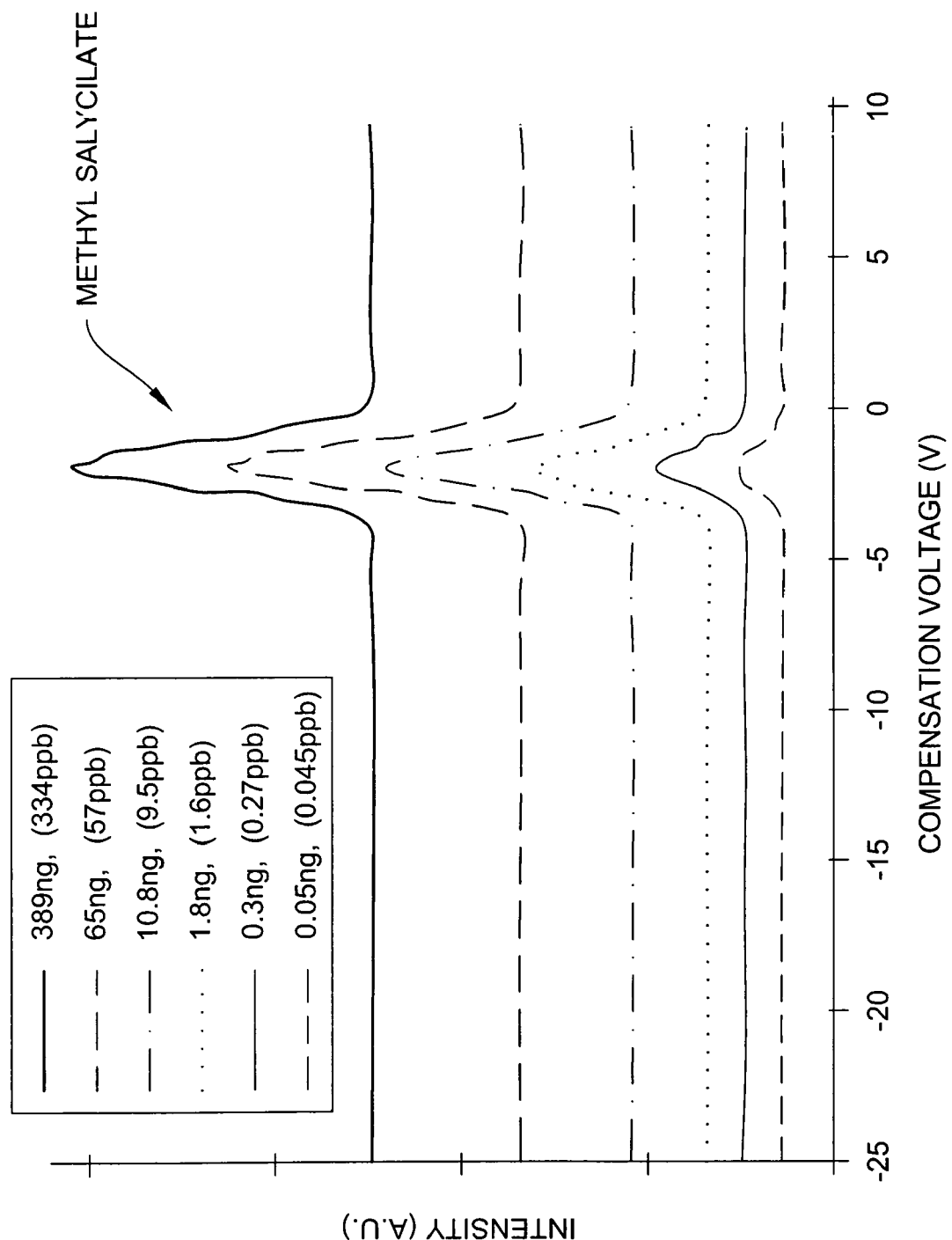
Figure 32:
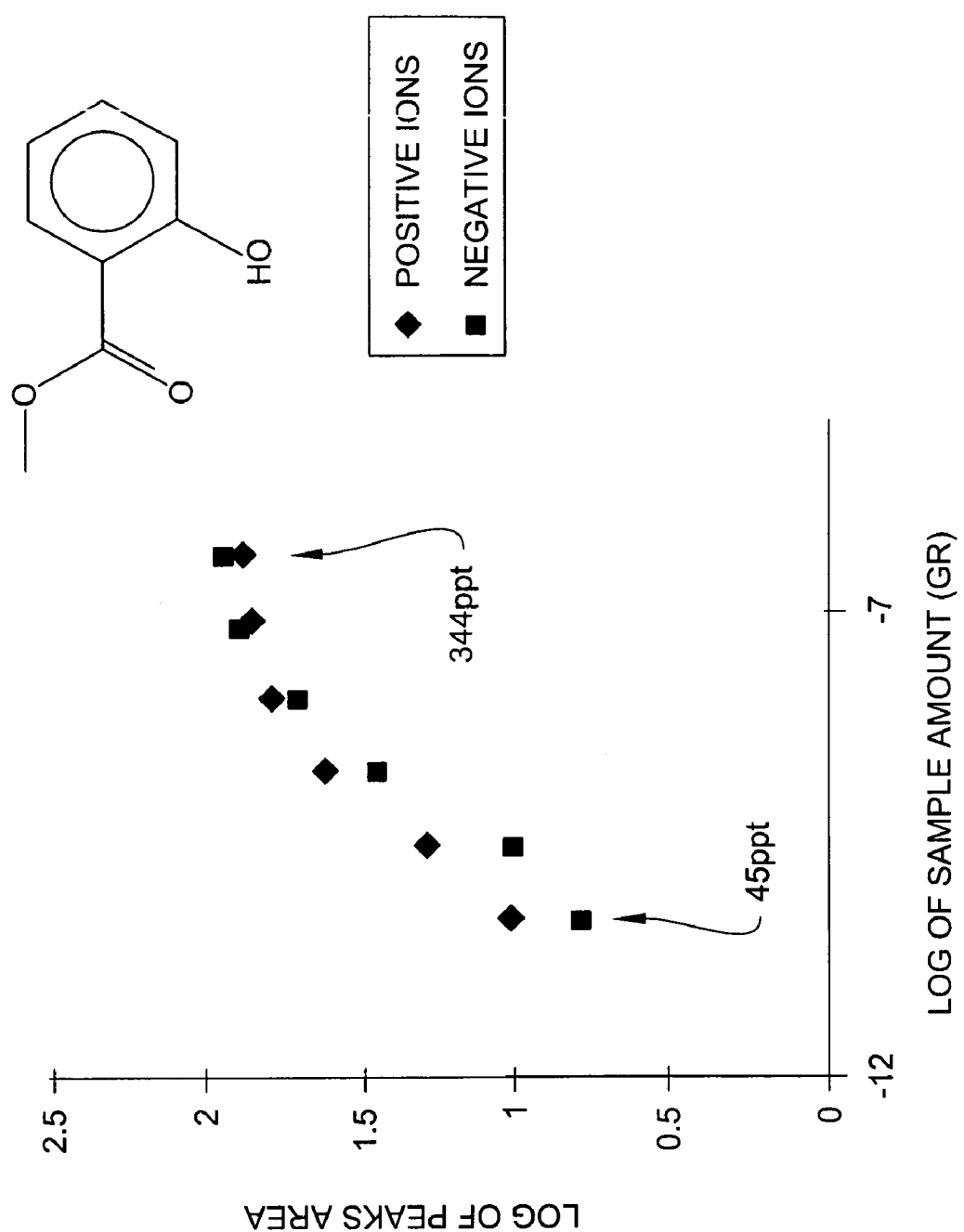

FIGS. 31 and 32 show the response and concentration dependence in DMS practice of the invention for methyl salycilate, a chemical warfare agent simulant. FIG. 31 shows positive ion spectra for different concentrations of methyl salycilate. FIG. 32 shows concentration dependence of the system to methyl salycilate for both positive and negative ions. Samples with concentrations of methyl salycilate down to about 45 parts-per-trillion are readily detectable in this device. The methyl salycilate compound produces both positively and negatively charged ions which exhibit similar concentration dependences. The apparatus of the invention is able to simultaneously detect both ion responses within the same analytical run. Producing simultaneous positive and negative ion species information improves compound identification at reduced detection times.

Example 10

Smoke Analysis from the Combustion of Cotton, Paper, Grass, Tobacco and Gasoline Samples Using GC-DMS Materials and Methods Smoke from combustion of cotton, paper, grass, tobacco and gasoline (in an internal combustion engine) were sampled by SPME and the samples were screened using a GC-DMS. As a control, a measure of the chemical vapor composition of several materials using GC-MS was performed, as well as discrimination of vapor profiles between the tested analytes (including several cellulose materials) by GC-DMS, and then identification of chemical markers specific to the burning of a particular material.

In one demonstration of the invention, model 5880 gas chromatograph (Hewlett-Packard Co., Avondale Pa.) was equipped with a HP splitless injector, 25 m SP 2300 capillary column (Supelco, Bellefonte, Pa.), a flame ionization detector, and a DMS detector. A model 5880 gas chromatograph (GC)(Hewlett-Packard Co., Avondale Pa.) was equipped with a HP splitless injector, 25 m SP 2300 capillary column (Supelco, Bellefonte, Pa.), a flame ionization detector.

The carrier gas was nitrogen (99.99%) scrubbed over a molecular sieve bed and pressure on the splitless injector was 10 psig with a split ratio was 50:1. Other experimental parameters for the GC included: initial temperature, 30° C.; initial time, 5 min; program rate 15° C. min-1; final temperature, 200° C.; final time, 1 min.

The DMS detector was equipped with ~0.6-1 mCi of 63Ni. The drift gas was air at 1 to 21 min-1 from a model 737 Addco Pure Air generator (Miami, Fla.). The drift gas was further purified over a 5 Å molecular sieve bed (10 cm diameter×0.6 m long) and passed through heated stainless steel tubing to warm the drift tube to 70° C.

The analytical column was attached to the DMS drift tube through a 30 cm length of aluminum-clad column and column effluent was carried by drift gas through the ion source region for sample ionization. The drift gas also carried product ions through the gap (0.5 mm) between two flat separating electrodes (5×25 mm). Two electric fields were applied to the drift tube: a non symmetric waveform high frequency (1.3 MHz) with strong electric field (20 kV cm-1 peak to peak amplitude) and a weak DC field (−360 V cm-1 to +80 V cm-1) of compensation voltage (−18 to +4V). Signal was processed using a National Instruments board (Model 6024E), digitized and stored. Excel 97 (Microsoft Corp) and Origin v 5.0 were used to display the results as spectra in topographic plots and graphs of ion intensity versus time.

The gas chromatograph-mass spectrometer was a model 5890 A gas chromatograph and Model 5971A mass selective detector (Hewlett-Packard Co., Palo Alto, Calif.) and was equipped with a 25 m SP 2300 capillary column (Supelco, Bellefonte, Pa.). The operating parameters of the gas chromatograph/mass spectrometer (GC/MS) were identical to those for GC-DMS listed above. Conditions for the mass spectrometer were: mass range, 45-550 amu; threshold, 500; scan rate, ~200 amu s−1; and electron multiplier voltage, 2100-2500 according to the automated calibration routine.

Solid phase micro-extraction (SPME) fibers and injector were obtained from Supelco (Bellefonte, Pa.). A mixture of hydrocarbons (hexane to hexadecane) was prepared in methlyene chloride solvent at 100 ng/ul per alkane. The alkanes were obtained from various manufacturers and were used as a standard for calibration of chromatographic retention. Materials were all obtained locally and included paper as shredded newspaper; cotton; tobacco as cigarettes; and grass as dried Bermuda grass.

Procedure

In one demonstration, a wad of ~9 cm3 of loosely held material (cigarette excepted) was placed in the end of a borosilicate glass tube (2.54 cm OD×6 cm long) which was held level and a flame from a butane lighter was used to ignite the sample. The apparatus was placed in a fume hood where flow of air created air flow through the tube and allowed a sustained but low level burn of the sample over 3-8 minutes. Hot vapor and particulate emissions from the sample were released in a plume from the sample and the SPME fiber was held in this plume simulating field sampling of ambient air.

The time of sampling was 4 s for cotton, 6 s for cigarettes, 8 s for paper and 10 s for grass. Samples of engine exhaust from a forklift truck were taken by holding the SPME fiber in the exhaust stream approximately 0.5 meter from the end of the tailpipe. The samples were freshly analyzed by GC-MS or GC-DMS. In an injection, the SPME was placed in the injection port under splitless mode and held for 30 seconds until the inlet was switched to split mode. The SPME fibers were conditioned between runs for 10 minutes at 220° C. in nitrogen. Repeatability was obtained by four replicate measurements of cotton burns with 4 s sampling of the smoke plumes. The alkane standard was used to calibrate retention on the GC-MS and the GC-DMS.

Figure 33:
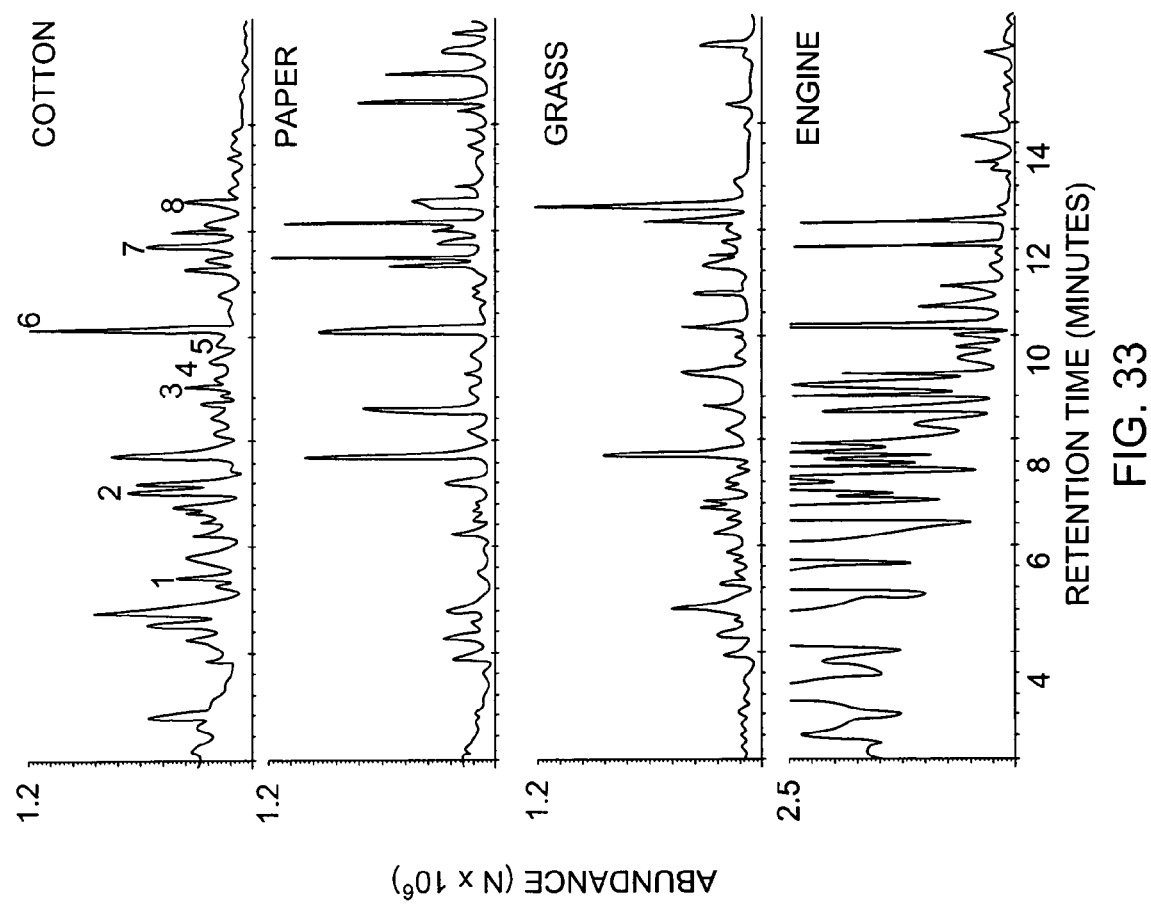

Detection of VOC from Combustion of Fuel Sources by GC-MS A preliminary requirement in this study was to determine if smoke samples taken by SPME methods and analyzed by capillary GC-MS would provide chromatographic profiles for VOCs sufficiently distinct to be attributed to specific fuel sources. Results from GC-MS analysis of SPME samples from four of the five combustion sources (cotton, paper, grass and engine exhaust) are shown in FIG. 33 as total ion chromatograms. These VOCs spanned the range of carbon numbers from 10 to 18 as shown in retention times for the alkane standard under identical conditions. Time (in minutes) for the alkanes (not shown) were: decane, 4.27; undecane, 5.54; dodecane, 7.00; tridecane, 8.40; tetradecane, 9.81; pentadecane, 11.17; hexadecane, 12.47, and octradecane, 15.79 (alkanes with carbon numbers below 10 were lost in the solvent delay). The traces in FIG. 33 spanning 2 to 20 minutes retention illustrate that all samples exhibited a complex mixture of VOCs from adsorbed aerosols (desorbed in the injection port) and molecular weights for these compounds can be estimated as ~150 to 250 amu. Additional chemical information for compounds with molar masses below 150 amu was not sought as such compounds were regarded as too volatile to be collected by SPME sampling methods. Also, no particular effort was made to measure constituents above 250 amu. The emphasis in these measurements was a comparison of emission composition available by SPME sampling without requirements for cryogenic options or ultra high temperatures. Thus, these findings are not a comprehensive chemical characterization of vapors and the measurements were made in anticipation of practical, field-portable instruments which would be engineered for operation under simple conditions according to embodiments of the invention.

In the range of molecular weights screened in FIG. 33, clear differences existed in the qualitative and quantitative distributions of peaks in the chromatographic profiles. While the profiles of total ion chromatograms appear distinctive in FIG. 33, peaks in cotton, paper and grass were shared in common by these cellulose based materials though differences could be found in relative abundances. An inspection of the chromatograms showed that there were 10 constituents in cotton that were distinctive over all other constituents in other samples and these distinctive components are shown in Table 1. In summary, these findings demonstrated that the chemical composition of emissions from burning materials of interest exhibited measurable chemical differences through analysis by high resolution GC-MS. Thus, there is a chemical basis for an advanced smoke detector to discriminate between source materials of fires. Naturally, exhaustive studies on the composition of smoke and reproducibility of sampling and analysis would be needed to further refine these observations. However, precision (discussed below) demonstrated that the differences were not random, encouraging further study.

Ion mobility spectrometers are equipped with an atmospheric pressure chemical ionization (APCI) source and an intermediate step was to determine if the pre-separation could be eliminated from the method. Direct sampling of emissions using an APCI mass spectrometer was made to determine the APCI response to effluent constituents and to measure the resolution possible with a mass spectrometer alone.

Figure 34:
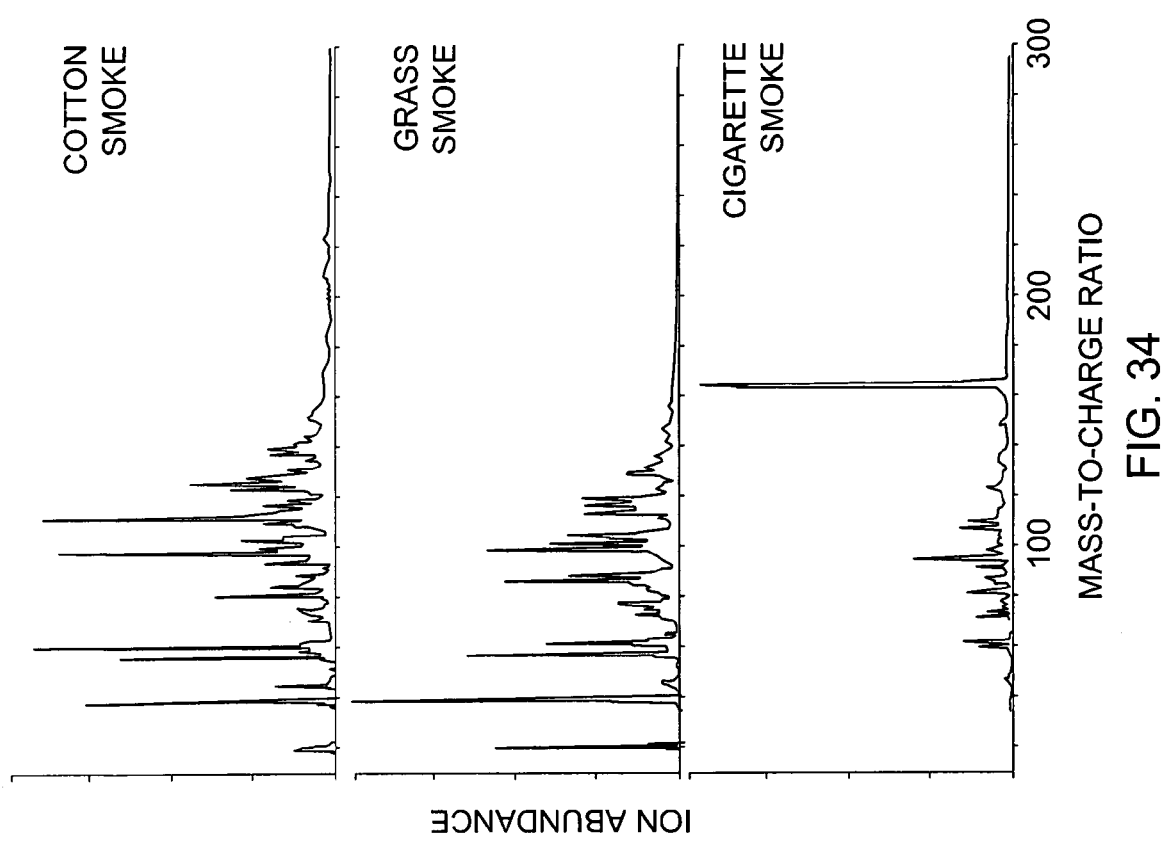

The mass spectra from direct sampling of vapors with a corona discharge ion source for grass, cotton and cigarettes are shown for positive ions in FIG. 34 and Table 2. In the background air, the reactant ions were ions with m/z 19, 35, 55, 73 amu corresponding to ions of H3O+(H2O)n with n=0, 1, 2, 3, respectively. Distinctive among these spectra for direct sampling of combustion emissions is that for cigarette smoke where nicotine is evident at m/z 163 amu. Nicotine has a large proton affinity and has been known for decades to yield protonated monomers through reactions as shown in Equation 3:

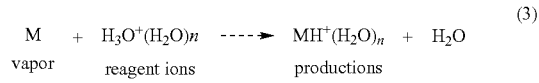

(3)

Consequently, nicotine preferentially acquired charge from the reactant ions over other sample vapors and became the dominant ion through competitive charge exchange. Other constituents are present (as shown in FIG. 34, cigarette smoke) but the nicotine protonated monomer towers above all other peaks in the APCI mass spectrum.

In the other samples, the distribution of vapor concentrations and proton affinities of the VOCs yielded complex mass spectra with masses between 60-200 amu for grass and cotton. There were complex with ions common to each owing to gas phase ionization reactions at ambient pressure. Though multivariate methods might be employed to categorize the sources responsible for the mass spectra in FIG. 34 (cotton smoke and grass smoke), the peaks were separated by unit mass generally in the mass spectrometer (Table 2). The resolution of a mobility spectrometer is inadequate to provide satisfactory separation of such complex ion mixtures. Therefore, pre-separation, such as by capillary GC, was regarded as essential for highly reliable separation and identification.

GC-DMS Analysis of VOC from Combustion of Various Materials

Figure 35:
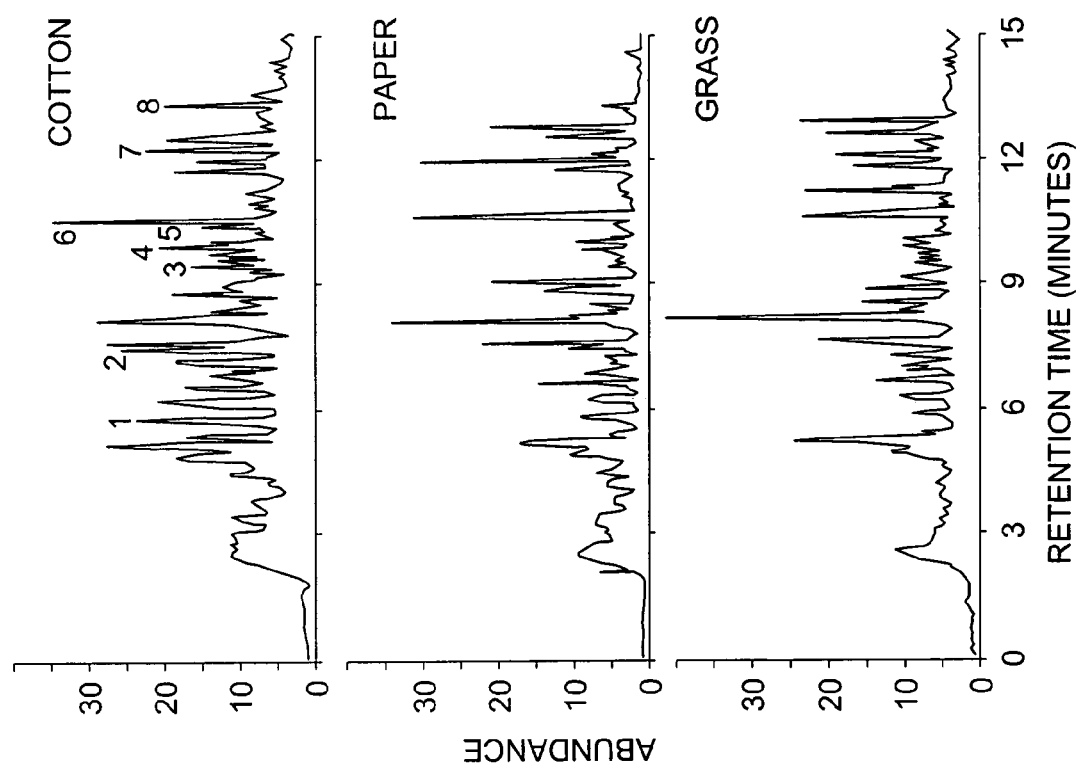
Figure 36:
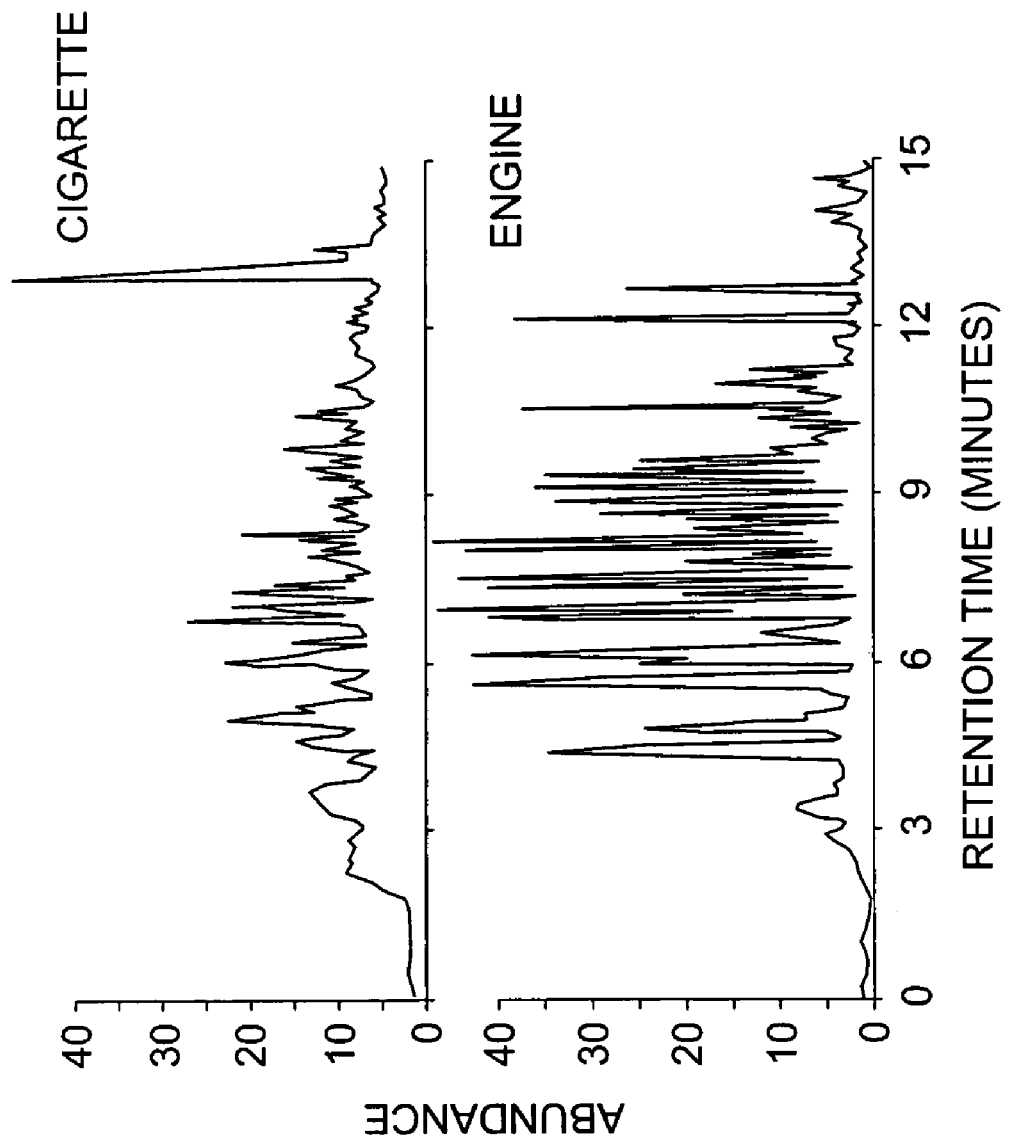

While samples may be drawn directly from the ambient environment into the first separation stage S-A in embodiments of the invention, we now discuss GC-DMS analysis of SPME-collected samples of combustion emissions, as shown in FIGS. 35 and 36 as chromatograms of total intensity of product ions from the mobility scans in comparable format to total ion chromatograms from GC-MS (see FIG. 33). Plots are shown for cotton, paper grass, cigarette and gasoline engine smoke and the findings reflect the same level of complexity (i.e., number of resolved constituents) as seen above in the GC-MS plots. Here also, as expected, the VOCs spanned the range of carbon numbers from 10 to 18 as shown in retention times spanning 3 to 15 minutes. For the alkane standard (not shown) under identical conditions times (in minutes) were: nonane, 3.54; decane, 4.52; undecane, 5.81; dodecane, 7.24; tridecane, 8.77; tetradecane, 10.27; pentadecane, 11.78; and hexadecane, 13.43. The run was ended before octadecane eluted; alkanes with carbon numbers below nine appeared in a large unresolved peak from 2 to 3.5 minutes.

Differences were observed in relative abundances of constituents within the chromatograms between FIG. 34 and those in FIGS. 35 and 36. This is associated with differences in response factors between mass spectrometry and ion mobility spectrometry or differences between vacuum based ion formation and ionization at atmospheric pressure. In the later, response is roughly approximated by proton affinities of molecules. Thus, what appear as minor constituents in emissions from cotton between 8 to 10 minutes (FIG. 33) appear as significant constituents at the same retention time in FIG. 35. On the one hand, cigarette smoke nicotine dominated the DMS chromatographic response (FIG. 36) as it did the MS trace (FIG. 34). On the other hand, the response to small molecules from C10 to C14 by DMS (FIG. 36) was clearly more pronounced than that from MS (FIG. 34).

Reproducibility was determined using the peak heights on the production plots of FIGS. 35 and 36 and results are shown in Table 3 for several peaks from throughout the elution program. The relative standard deviation of the measurement was ranged across a comparatively narrow gap from 17 to 30% RSD. This variation included all aspects of sample preparation, sampling, measurement, and automated data reduction. As a consequence, results from this method exhibited actual differences that could not be attributed to variance or random error even though sampling was made with comparatively casual attention to the limitations of SPME.

The peaks unique to cotton were labeled in FIGS. 33 and 35 and summaries of the mass spectral properties for these are shown in Table 1. The GC-DMS results could be compared directly to the findings from GC-MS and certain peaks were found in the cotton to be unique or special to cotton combustion. These are labeled in FIG. 35 and mass spectral properties are listed in Table 2. The 2D plots are particularly good for quantitative measures but do not disclose the analytical value of orthogonal information available in the mobility scan. This can be seen in the topographic plots of FIGS. 37 and 38.

Figure 37:
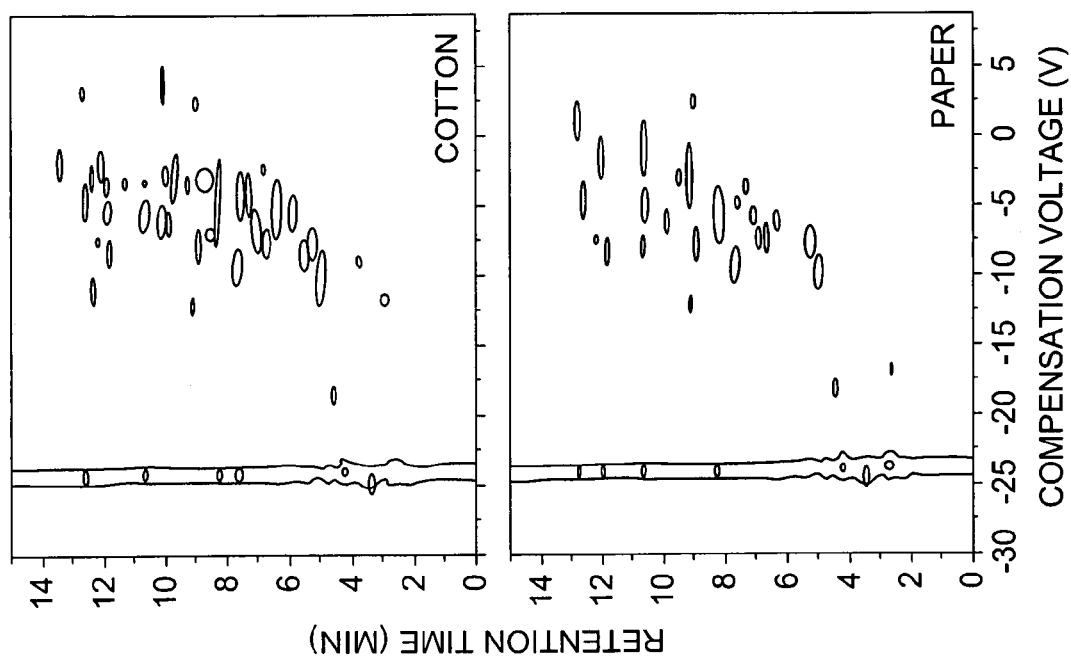
Figure 38:
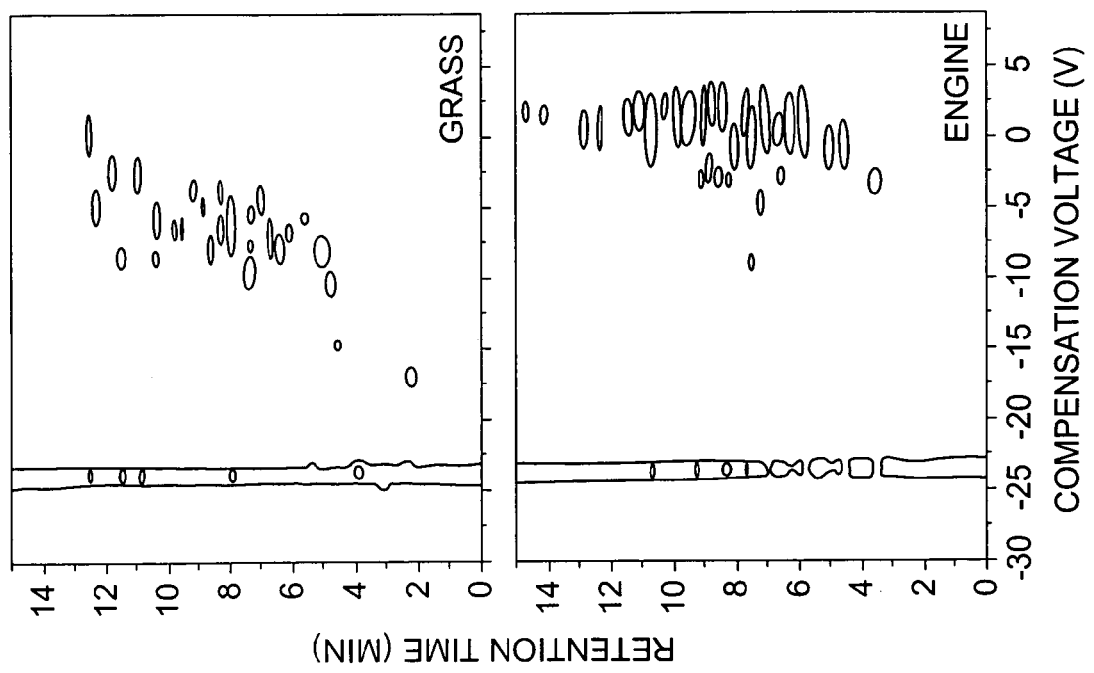

Topographic plots from GC-DMS analysis of all samples demonstrated that information in the mobility scan provides distinctiveness for each sample. The most distinctive of the plots, shown in FIGS. 37 and 38, is that from the internal combustion engine where incompletely combusted hydrocarbons appear in a narrow band of compensation voltage from −2 to 2 V. This was consistent with mass spectra and with the alkane standard with peaks of similar compensation voltage. Plots for the cellulose materials (cotton, paper, and grass) exhibited some common features with peaks from 5 to 14 minutes evenly distributed and compensation voltages that spanned −10 to +5V. In general, the compensation voltage trended from −10V toward 0V with increased retention time. These results were promising as an examination of the concept of GC-DMS as an advanced smoke detector. As well, it is further noted that cotton exhibited unique or characteristic peaks in the 3-D plots as labeled in FIG. 37 (cotton) and FIG. 33 (cotton).

All of these results had been obtained using comparatively slow GC temperature ramps. The 15 minutes might be reduced substantially with a fast GC. An essential question is what information is available in the plots and to what degree can this information be compressed without losing measurement resolution beyond a usable condition. In mass spectrometry, selected ion monitoring is used to improve detection limits and can add selectivity through ion ratio measurements. This same concept can be applied to DMS to monitor certain ions. This approach to measurement provided a reliable route to fast chromatography (FIGS. 39 and 40).

Figure 39:
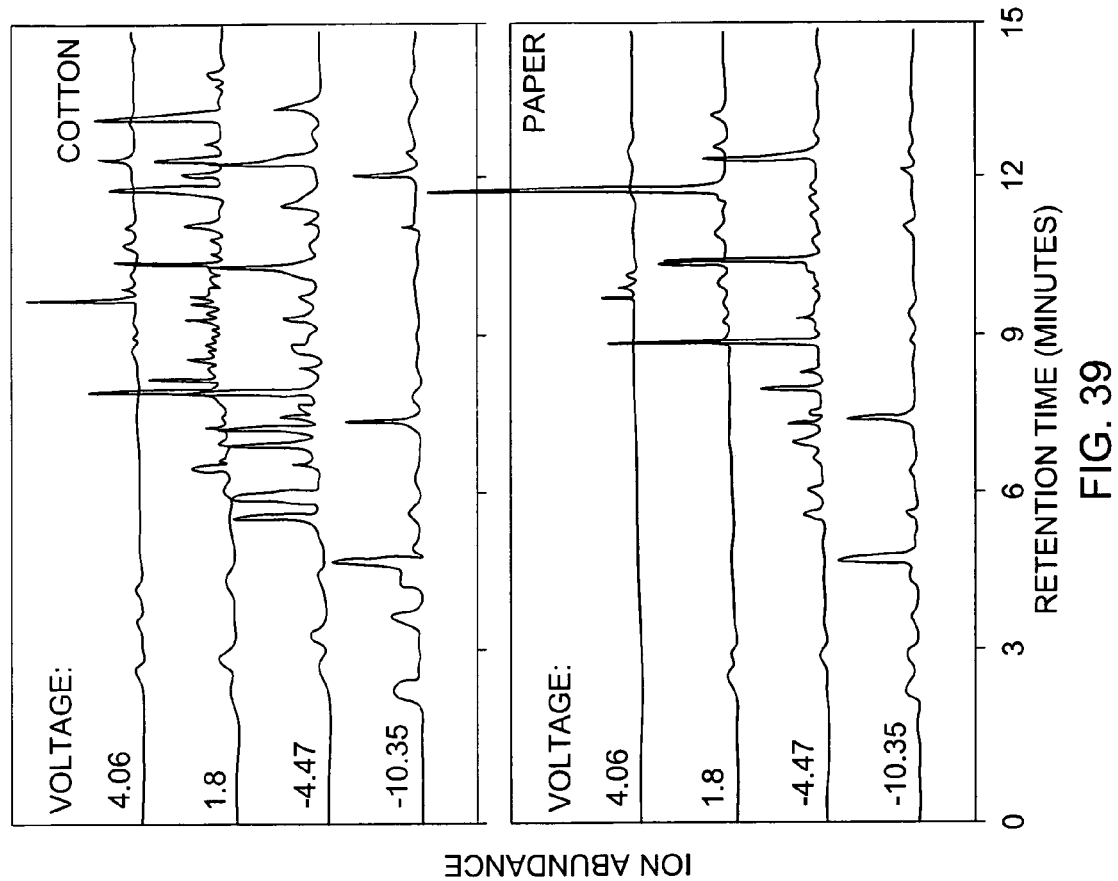
Figure 40:
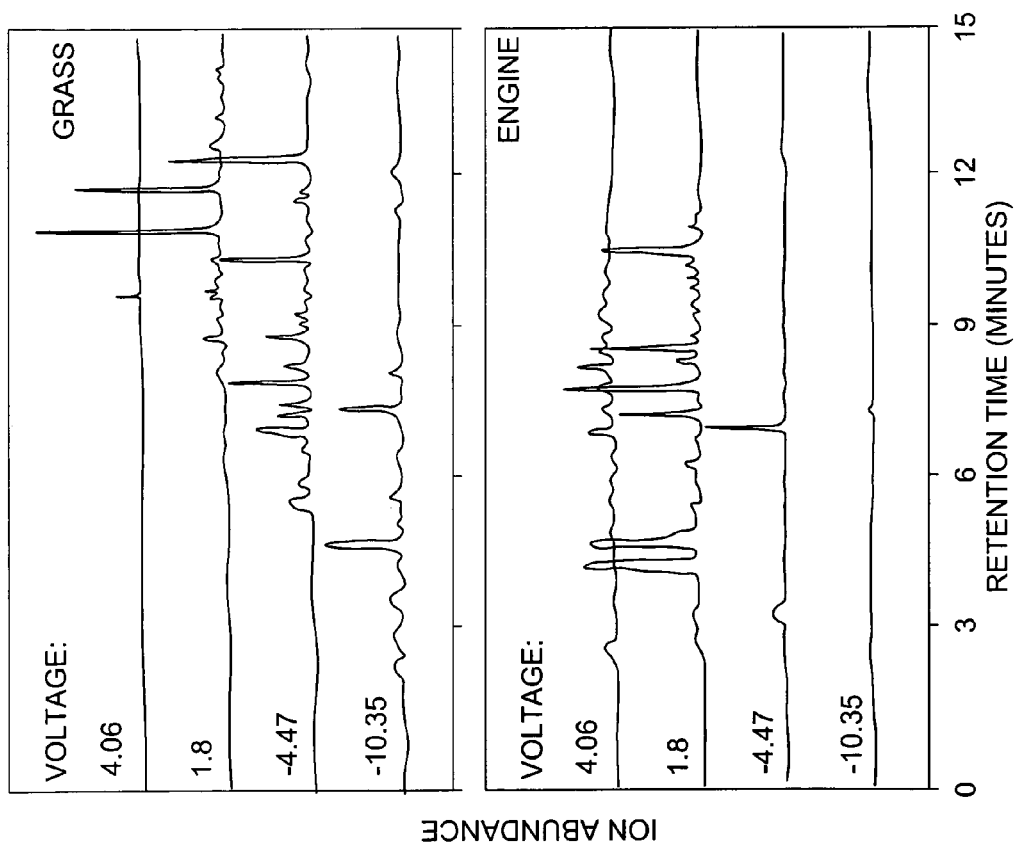

In FIGS. 39 and 40, plots of ion intensity at four compensation voltages (4.06V, −1.8V, −4.47V, and −10.35V) are shown top to bottom in each frame for cotton, paper, grass and gasoline engine exhaust. With this approach which is analogous to ion chromatograms in GC/MS measurements, certain regions of compensation voltage were graphically extracted from the matrix of retention time, compensation voltage and ion intensity. A measure of the amount of chemical information in the selected ion mobility plots from GC-DMS can be seen in these figures where differences in samples are further accentuated. These patterns are distinct and show that selected ion plots allow a route to chemical identification where information can be compressed through fast chromatography. A further embodiment includes forming ratios of two or more extracted ion chromatograms.

The findings in FIGS. 39 and 40 demonstrate that adequate resolution of peaks is available in these complex patterns to compress the chromatographic time scale. At present the scan time of 1 s may be too slow for below 3 minutes. Since ion residence in the drift tube is 1-2 ms, ion hopping could occur for a set of ions in 40 ms, (4 ions for 10 ms each). Thus, high speed GC where the complete separation occurs in 60 seconds is preferred to allow high cycles (e.g., 1000) throughout the measurement. The time resolution of 1 part in 1500 would be comparable to the current value of 1 in 960. Thus, should all other facets of separation be scalable, the drift tube with ion hoping enables high speed GC-DMS as a realistic smoke detector to distinguish sources of smoke.

TABLE 1

Retention times and ions in mass spectra from peaks that appear distinctive to cotton emissions.

| Peak No* | Retention Time (min) | Prominent Ions in order of abundance (base peak abundance) |
|---|---|---|
| 1 | 5.51 | 43 (190,000) 72, 55, 83, 98 |
| 2 | 7.13 | 42 (180,000), 41, 55, 86, 96 |
| 3 | 9.09 | 55 (24,000), 126, 41, 42, 43, 53, 69 |
| 4 | 9.55 | 42 (42,000), 41, 57, 56, 100 |
| 5 | 9.94 | 43 (19,500), 41, 55, 57, 70, 69, 83 |
| 6 | 10.19 | 44 (390,000), 57, 43, 41, 128 |
| 7 | 11.78 | 69 (110,000), 57, 41, 42, 70, 43, 144 |
| 8 | 12.61 | 102 (54,000), 132, 101, 78, 77, 51, 50 |

*Refer to FIG. 33.

TABLE 2

Ion masses from direct sampling of smoke from cigarettes, grass, and cotton with analysis by atmospheric pressure ionization mass spectrometry

| Mass | Cigarettes Intensity | Grass Intensity | Cotton Intensity |
|---|---|---|---|
| 37 | | 10,064,000 | 5,420,000 |
| 44 | | 1,210,000 | |
| 55 | | 6,562,000 | 4,558,000 |
| 60 | 1,070,000 | 4,050,000 | 6,978,000 |
| 70 | 732,000 | | |
| 71 | | 1,290,000 | |
| 73 | | 1,054,000 | |
| 74 | | | 866,000 |
| 75 | | 1,812,000 | |
| 80 | 1,020,000 | | 2,532,000 |
| 81 | | 1,010,000 | |
| 83 | | 1,546,000 | 1,340,000 |
| 85 | | 5,398,000 | 1,276,000 |
| 87 | | 3,416,000 | |
| 88 | | | 728,000 |
| 90 | 782,000 | | |
| 94 | 2,144,000 | | 1,528,000 |
| 97 | | 5,890,000 | 5,960,000 |
| 99 | | 3,986,000 | 1,630,000 |
| 101 | | 2,104,000 | |
| 102 | | | 2,020,000 |
| 103 | | 3,338,000 | |
| 104 | | | 1,102,000 |
| 106 | 1,134,000 | | |
| 108 | 930,000 | | |
| 109 | | | 1,548,000 |
| 111 | | 2,874,000 | 6,284,000 |
| 113 | | 2,010,000 | 2,042,000 |
| 115 | | 2,860,000 | |
| 116 | | | 1,558,000 |
| 117 | | 2,960,000 | |
| 118 | | | 996,000 |
| 123 | | | 2,244,000 |
| 125 | | | 3,160,000 |
| 127 | | 1,694,000 | 1,912,000 |
| 129 | | 1,068,000 | |
| 130 | | | 990,000 |
| 137 | | | 1,430,000 |
| 139 | | | 1,424,000 |
| 142 | | | 866,000 |
| 164 | 7,034,000 | | |

TABLE 3

Reproducibility of combustion experiments including sampling, GC-MS determination and data reduction. Measurements were made using 4 s burns of cotton with four complete replicate experiments.

| Retention Time (min) | Area | Standard Deviation | % Relative Standard Deviation (% RSD) |
|---|---|---|---|
| 2.9 | 20696587 | 5188474 | 25.07 |
| 5 | 26439681 | 5973165 | 22.59 |
| 8 | 19698838 | 6011899 | 30.52 |
| 11.8 | 12360466 | 3020822 | 24.44 |
| 12.7 | 10095391 | 1749393 | 17.33 |
| 14.02 | 3873334 | 1167082 | 30.13 |

Example 11

Detection of Chemical Warfare Agent Simulants

With the continuing threat from chemical and biological weapons, the need for more effective and reliable detectors continues to be an issue for both the military and homeland security. Most, if not all, of today's deployed detection devices were developed to address the relatively narrow range of classic warfare agents (CWAs) of the cold war era. However, with the escalation of world terrorism there comes the need to deal with a broader range of threats that include a substantial list of toxics, including so-called toxic industrial chemicals and toxic industrial materials (a.k.a. TICs and TIMs). This places an even greater burden on detector technologies which must offer even higher selectivity without compromising sensitivity. The requirement is for fast response times with significantly lower false positives. Most of the currently deployed detectors are based on IMS technology, developed to maturity over the last several decades and now struggling to adapt to these increasing/changing requirements. Meanwhile, practices of the present invention overcome these difficulties.

There are a variety of different interferences present in real world conditions such as: Aqueous Fire Fighting Foam (AFFF), diesel fuel, gasoline, pesticides, paints and floor waxes that lead to a high rate of false positives in the currently deployed conventional IMS detectors. Frequent false alarms are often experienced in the dusty, smoke-ridden, environments. These lead to a loss of confidence in detection equipment. These false positives can be caused in IMS equipment by the fact that many ion species can have the same, or very similar, low field mobility coefficients. Practices of the present invention overcome these difficulties as well.

In one practice of the invention, trace compounds were detected after ionization with a $^{63}$Ni radioactive source. To demonstrate the invention, experiments were performed with calibrated standards of the CWA simulants: Dimethyl methylphosphonate (DMMP), Diisopropylmethylphosphonate (DIMP) and Methyl Salicylate (MS). Three independent vapor generator systems (Vici Metronics Inc, Model 190) were used to generate controlled air mixtures of the simulants at different concentrations. Permeation sources were purchased from KIN-TEK with calibrated emission rates of 160 ng/min DMMP at T=80 C, 301 ng/min DIMP at 100 C, and 5240 ng/min MS at 100 C. Gas flow rates in all three systems were the same 100 cc/min. The maximum sample concentrations that could be provided was 1.6 mg/m$^3$ for DMMP, 3.01 mg/m$^3$ for DIMP, and 52.4 mg/m$^3$ for MS.

The DMS filter was operated in one aspect where it sampled effectively 100% of an incoming trace gas sample. In a 100% duty cycle aspect of the invention, the compensation voltage is fixed such that a particular ion species, identified by its differential mobility, is permitted to reach the detector. This is in contrast to conventional IMS which typically uses a gate which is pulsed "open" for approximately 1% of a measurement cycle resulting in only about 1% of the ions being sampled. The DMS filter of this embodiment did not contain an ion-gate as in IMS devices, and is therefore more sensitive than gated approaches (where large portions of the sample signal are discarded). In addition to the absence of a gate, in the present invention it is possible to improve sensitivity wherein the signal can be integrated over a relatively long period of time.

The DMS was also operated in a second aspect in order to produce a spectroscopic output by scanning a range of compensation voltages. This reduces the "effective" duty cycle, but since the range of compensation voltages that is scanned can be selected by the operator, the "effective" duty cycle for any type of ion species is significantly higher than in conventional IMS. The sensitivity of the system is higher than conventional IMS with the ability to detect compounds in the ppt range.

Increased sensitivity is invaluable, especially in applications requiring miosis level detection. However, a detector which has high sensitivity without selectivity leads to an even higher rate of unwanted false positives. As previously mentioned, enhanced selectivity in the DMS systems of the invention are provided by changing the electric field strength applied to the ionized molecules. In practice, this translates to changing the field strength of the asymmetric oscillating RF field (Vrf). Changing the RF field results in a corresponding shift in the spectral peak position, as measured by the compensation voltage. Changing the RF field leads to tunable resolution accessed by changing the RF filtering amplitude and thus changing the operating point on the mobility vs. electric field curve. In the system the various RF field values can all generated under the automatic control of the microprocessor. The tunable resolution makes it possible to separate monomers from dimers and other clusters and to use these cluster peaks to aid in the identification of compounds, for example, at FIG. 41 (top curves).

Tunable resolution also enables the RIP (reactant ion peak) to be displaced away from the peaks of interest. The RIP is a background peak that frequently interferes with the detection of targeted compounds in conventional IMS. This property of the invention enables the detection of trace compounds in backgrounds that produce interfering signals, or in some situations where the RIP or other compounds would otherwise interfere with successful detection. Tracking how the spectral peak position shifts with RF field provides a great deal of information unique to that ion species, peaks for other ion species will shift very differently. These are species-specific signatures which can be used to identify detected species in practice of the invention. As earlier described, embodiments of the present invention can simultaneously detect both positive and negative ion peaks, modes, which further helps to improve selectivity. The absence or the presence of peaks, and their size and location, in the positive ion channel versus the negative channel provides more information on the specific compound identity. The ratios between intensities of positive ions and negative ions for a given sample also provides additional information which enhances confidence of the detection.

Figure 42A:
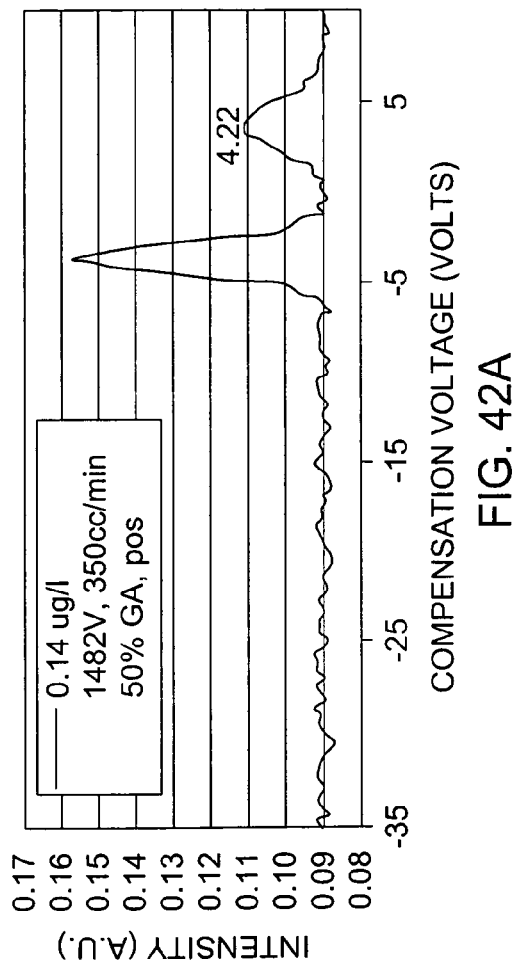
Figure 42B:
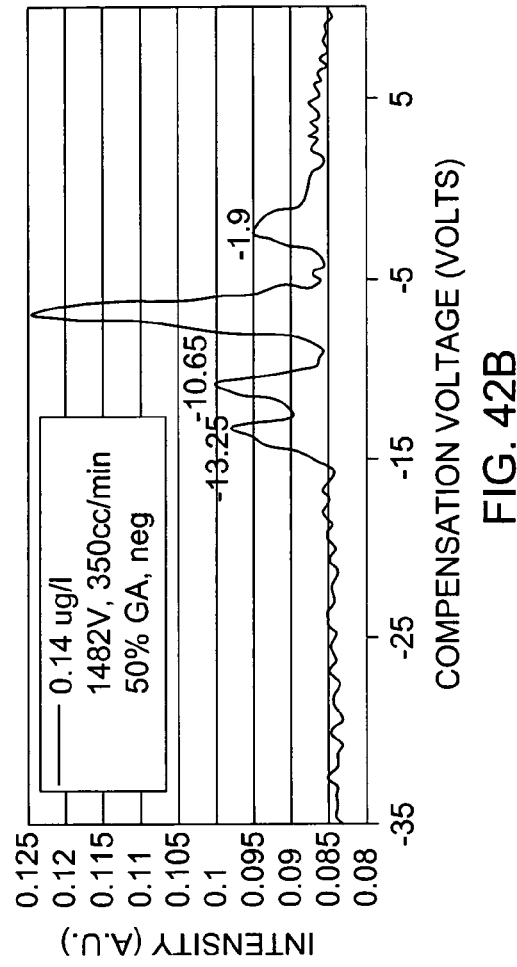

FIG. 42A and FIG. 42B illustrate this for the nerve agent GA. These spectral plots were measured at a Vrf of 1,482 v which corresponds to a field strength of 29,640 v/cm. The characteristic spectrum for the positive ions is very different from the negative ion spectrum.

The combination of the positive and negative ion channel information, together with the information provided by monitoring the spectral peak shifts as a function of the applied RF field, results in a powerful tool for chemical identification in practice of the present invention.

In some cases it is desired to achieve narrower peaks and better peak resolution, such as for discriminating between peaks for similar or interfering analytes in a sample. An additional embodiment of the present invention addresses this concern by operating the system at slightly reduced pressures relative to atmosphere. Under these reduced pressure conditions, down to 0.5 atmospheres, the resolution according to the invention is significantly increased.

Figure 43:
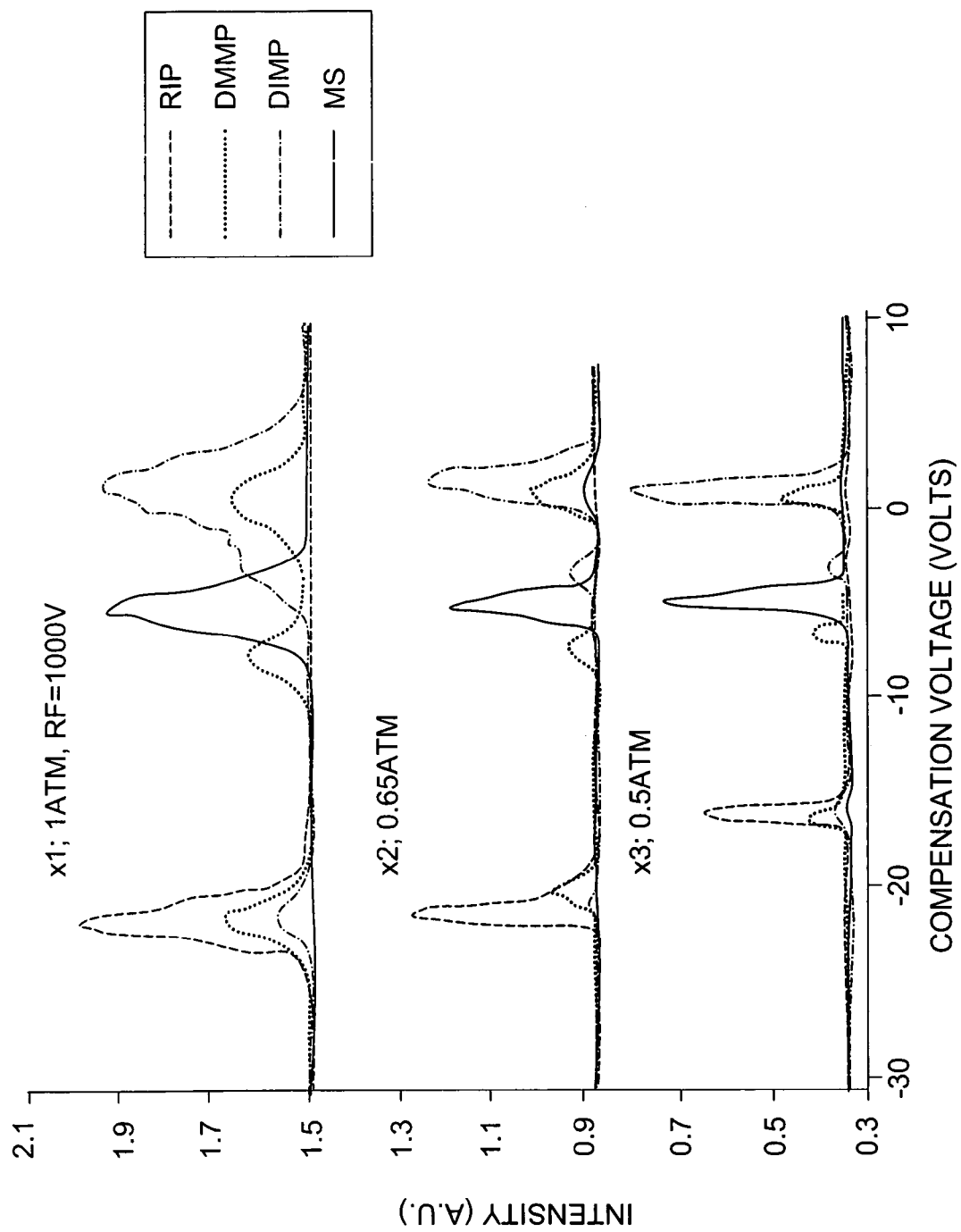

The effect of reduced pressure is illustrated in FIG. 43 for three CWA simulants, DMMP, DIMP, and MS. The top spectra show the results obtained at atmospheric pressure, RF=1000V, while the next spectra was obtained at 0.65 atm, RF=800V, and the bottom spectra was obtained at 0.5 atm, RF=650V. It will be appreciated that the top scan discriminates between the three simulants with some spectral overlapping but which may be adequate in some cases. However the next lower scan has better resolution (narrower peaks) and the lowest scan has even better resolution. Thus it is possible to discriminate between such analytes in a sample by reducing operating pressure, according to aspects of the invention.

A further advantage of reducing pressure in the system is that the amplitude of RF voltages required to filter the ions can be reduced, this results in a lower power requirements which is especially important for field-portable systems of the invention.

Figure 41:
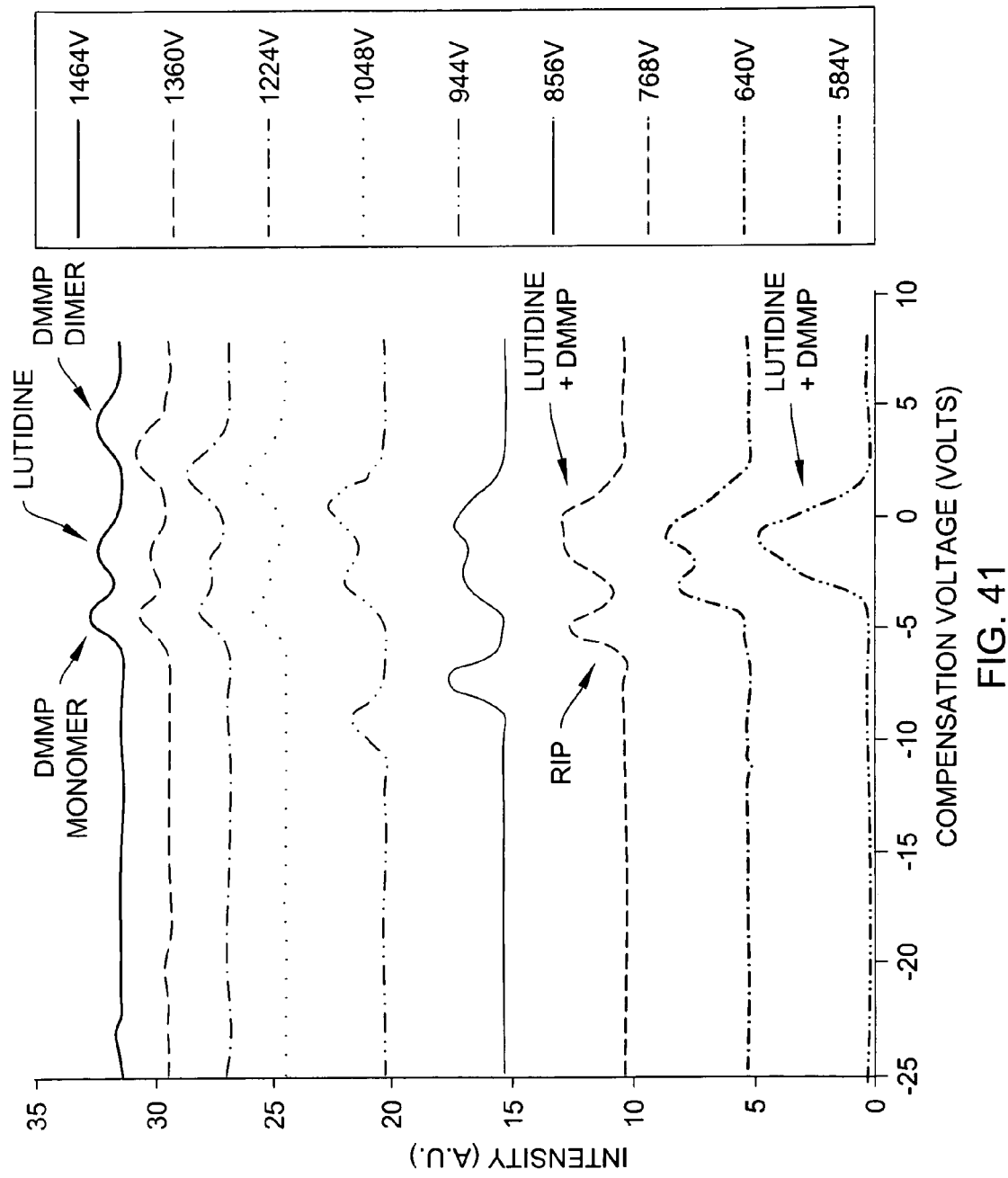

In one embodiment of the invention, direct sampling of volatile chemical agents provides adequate detection results, as was the case with FIG. 41, especially in the upper scans. However it is also possible to use a first stage of separation, such as previously discussed which results in providing a less complex ionized sample to the DMS, resulting in a less complex sample being ionized and filtered in the DMS filter.

In one practice of the invention, a membrane was used at the input of the DMS filter system prior to ionization, such as at separation stage S-A in FIG. 2A. The plots of FIG. 43 were obtained with such a membrane front end. Selection of membrane is guided by the need to selectively pass CWA agent molecules while acting as a barrier to moisture and heavier molecules (whether dirt, dust, hydrocarbon exhausts or the like). Thus a better and more controlled analytical environment can be provided within a detection system of the invention with a less complex sample being ionized and filtered within the DMS filter. The plots of FIG. 43 were taken using a membrane front end as separator that selectively introduced the detected CWA agents as indicated while acting as a barrier to moisture and unwanted heavier molecules. Various membrane materials are known in the art, including partially porous materials. These materials may include Teflon, latex, pdms, dimethyl silicone, or the like, as may be used in membrane practices of the invention.

Figure 44:
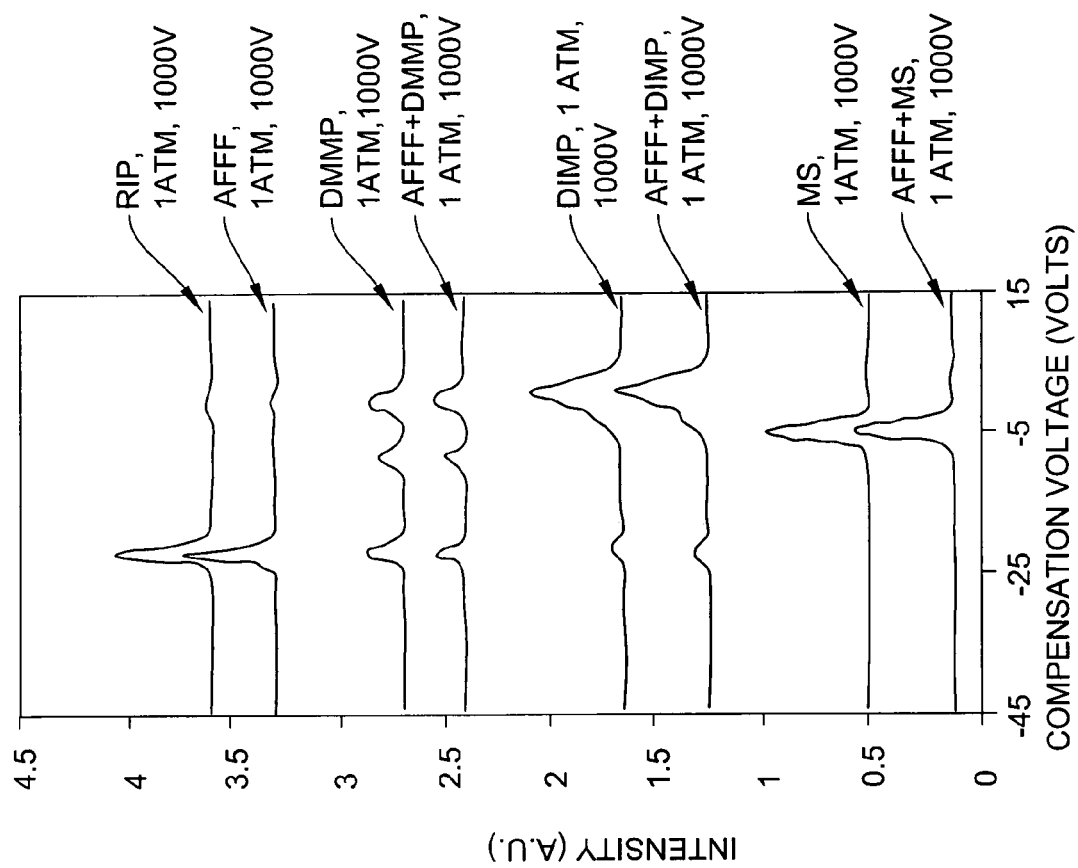

One of the critical aspects of a CWA detector is how well it can reject interferants to prevent false alarms. One particular interferant, Aqueous Fire Fighting Foam (AFFF), has proved extremely challenging for conventional IMS to resolve from CWAs, or CWA simulants. The AFFF peak tends to overlap with that of the agent peak in IMS. FIG. 44 demonstrates a practice of the invention for a series of warfare agent simulants selectively mixed with 1% headspace of AFFF. As can be seen, good DMS peak resolution can be achieved in practice of the invention. There are eight spectral plots in FIG. 44. The top plot shows the RIP for a DMS system with background air but no sample present with the sensor at atmospheric pressure. The next plot shows AFFF interferant added. This results only in a slight shift to the left (more negative compensation voltage) of the RIP peak. The CWA simulant DMMP is then introduced alone into the spectrometer and the typical monomer and dimmer peaks appear together with a corresponding reduction in the RIP peak intensity. When 1% AFFF is added, the DMMP peaks are not effected and only a slight leftward shift of the RIP is observed. The same experiment was repeated with DIMP and the effect of AFFF was negligible. Introducing MS and monitoring the negative ion peaks gave the similar data illustrating the lack of interference with AFFF. The conclusion is that 1% AFFF has virtually no effect on the DMS practices of the invention for CWA simulant spectra. Similar results were obtained with live agents as well. This is an important breakthrough for CWA monitoring.

The present invention enables method and apparatus for high field asymmetric waveform ion mobility spectrometry, which can be favorably augmented with other collection and separation techniques, and packaged in a compact system. Other than planar configurations are possible. DMS configurations which may be practiced according to the invention may include method and apparatus using co-axial, cylindrical, flat, planar, radial, curved and other DMS electrode configurations. Embodiments of the invention may even be practiced augmented with prior art IMS and DMS filtering.

The high sensitivity, rugged design and ease of use and setup of embodiments of the invention are advantageous for many applications that involve chemical detection. A simplified hand-held device of the invention is dedicated to detection of a limited set of data and yet reliably detects and identifies ion species of interest. This practice may be augmented by dual mode detections. The result is added reliability in chemical detection in a simplified device.

It will now be appreciated that in practice of the invention we control the filter field, its electrical properties and its environment, in an ion-mobility-based system, to amplify differences in ion mobility behavior for species separation. Species are then detected and identified based on this function. We can further optimize the process by controlling ionization (such as by selection of sources of lower or higher levels of ionization energy).

It should be appreciated that numerous changes may be made to the disclosed embodiments without departing from the scope of the present invention. While the foregoing examples refer to specific embodiments, this is intended to be by way of example and illustration only, and not by way of limitation. It should be appreciated by a person skilled in the art that other chemicals and molecules may be similarly ionized and detected.

Therefore, while this invention has been particularly shown and described with references to the above embodiments, it will be understood by those skilled in the art that various changes in form and details may be made therein without departing from the scope of the invention encompassed by the appended claims.

What is claimed is:

1. A method for detecting chemical warfare agents comprising:
   ionizing a portion of an airborne sample into ions, and
   filtering a portion of the ions for at least one marker associated with a chemical warfare agent (CWA) within the sample using a differential mobility spectrometer filter to identify ions associated with the at least one marker.

2. The method of claim 1, wherein the filtering includes flowing the sample through an asymmetric field.

3. The method of claim 2 comprising applying a compensation field to the asymmetric field to selectively pass ions through the asymmetric field.

4. The method of claim 3 comprising controlling at least one condition of filtering.

5. The method of claim 4 comprising storing information about conditions of filtering of at least one known marker and adjusting the conditions of filtering to enable the at least one known marker to pass through the asymmetric field.

6. The method of claim 4 comprising storing information about conditions of filtering of a plurality of known markers and scanning at least one condition of filtering to enable the plurality of known markers to pass through the asymmetric field.

7. The method of claim 5 comprising eluting a portion of the sample from a gas chromatograph before one of ionizing and filtering the ions.

8. The method of claim 5 comprising pre-filtering the sample using a membrane.

9. The method of claim 8, wherein the membrane includes at least one polymer.

10. The method of claim 9, wherein the polymer includes one of Teflon®, latex, pdms, and dimethyl silicone.

11. The method of claim 8 wherein the pre-filtering includes acting as a barrier to at least one of moisture, heavier molecules, dirt, dust, and hydrocarbon exhausts.

12. The method of claim 5, wherein the marker includes a CWA simulant of at least one of Dimethyl methylphosphonate (DMMP), Diisopropylmethylphosphonate (DIMP) and Methyl Salicylate (MS).

13. The method of claim 5, wherein the marker includes one or more molecules, or fragments thereof, associated with at least one of a toxic industrial chemical, a toxic industrial material, a nerve agent, and a chemical warfare agent.

14. The method of claim 13 comprising micro-fabricating a portion of the differential mobility spectrometer filter.

15. An ion mobility based chemical warfare agent (CWA) detection system comprising:
- a sample introduction section for collecting an airborne sample, the sample possibly including at least one chemical warfare agent marker,
- an ion source for ionizing a portion of the sample,
- a differential mobility spectrometer filter for filtering out the at least one chemical warfare agent marker, and
- a detector for detecting the at least one chemical warfare agent marker.

16. The system of claim 15, wherein the passing through includes flowing the sample through an asymmetric field.

17. The system of claim 16, wherein the filter is configured to apply a compensation field to the asymmetric field to selectively pass ions through the filter.

18. The system of claim 17 comprising an electronic controller for controlling at least one condition of the filter.

19. The system of claim 18, wherein the controller is configured for storing information about filter conditions associated with filtering at least one known marker and adjusting the filter conditions to enable the at least one known marker to pass through the asymmetric field.

20. The system of claim 18, wherein the controller is configured for storing information about filter conditions associated with filtering a plurality of known markers and scanning the filter conditions to enable the plurality of known markers to pass through the asymmetric field.

21. The system of claim 15 comprising a gas chromatograph from which a portion of the sample is eluted before one of ionizing and pass through the ions.

22. The system of claim 19 comprising a pre-filter for filtering the sample using a membrane.

23. The system of claim 22, wherein the membrane includes at least one polymer.

24. The system of claim 23, wherein the polymer includes one of Teflon®, latex, pdms, and dimethyl silicone.

25. The system of claim 22, wherein the pre-filtering includes acting as a barrier to at least one of moisture, heavier molecules, dirt, dust, and hydrocarbon exhausts.

26. The system of claim 19, wherein the marker includes a CWA simulant of at least one of Dimethyl methylphosphonate (DMMP), Diisopropylmethylphosphonate (DIMP) and Methyl Salicylate (MS).

27. The system of claim 19, wherein the marker includes one or more molecules, or fragments thereof, associated with at least one of a toxic industrial chemical, a toxic industrial material, a nerve agent, and a chemical warfare agent.

28. The system of claim 27, wherein a portion of the differential mobility spectrometer filter is micro-fabricated.

* * * * *